United States Patent
Iida et al.

(10) Patent No.: US 8,022,617 B2
(45) Date of Patent: Sep. 20, 2011

(54) ORGANIC COMPOUND, CHARGE-TRANSPORTING MATERIAL, COMPOSITION FOR CHARGE-TRANSPORTING MATERIAL AND ORGANIC ELECTROLUMINESCENT DEVICE

(75) Inventors: Koichiro Iida, Yokohama (JP); Yuichiro Kawamura, Ichihara (JP); Tomoyuki Ogata, Yokohama (JP); Masayoshi Yabe, Yokohama (JP); Misako Okabe, Yokohama (JP); Masako Takeuchi, Yokohama (JP); Kazuki Okabe, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 441 days.

(21) Appl. No.: 12/095,024

(22) PCT Filed: Nov. 22, 2006

(86) PCT No.: PCT/JP2006/323330
§ 371 (c)(1),
(2), (4) Date: May 27, 2008

(87) PCT Pub. No.: WO2007/063760
PCT Pub. Date: Jun. 7, 2007

(65) Prior Publication Data
US 2009/0284134 A1 Nov. 19, 2009

(30) Foreign Application Priority Data
Nov. 30, 2005 (JP) ................. 2005-346164

(51) Int. Cl.
*H01J 1/62* (2006.01)
*C09K 11/06* (2006.01)
*C07D 235/26* (2006.01)

(52) U.S. Cl. ................. 313/504; 252/301.16; 548/306.4; 548/325.5; 548/440; 546/256

(58) Field of Classification Search ............... 428/690; 313/504; 252/301.16; 548/306.4, 325.5, 548/440; 546/256
See application file for complete search history.

(56) References Cited

U.S. PATENT DOCUMENTS

| | | | |
|---|---|---|---|
| 5,276,049 A | 1/1994 | Himmelsbach et al. | |
| 5,861,420 A | 1/1999 | Reitz et al. | |
| 6,034,248 A | 3/2000 | Itoh et al. | |
| 7,175,922 B2 * | 2/2007 | Jarikov et al. | 428/690 |
| 2005/0064240 A1 * | 3/2005 | Mishima et al. | 428/690 |

FOREIGN PATENT DOCUMENTS

| | | |
|---|---|---|
| DE | 41 23 245 A1 | 1/1993 |
| EP | 1 589 789 A1 | 10/2005 |
| EP | 1 672 961 A1 | 6/2006 |
| JP | 10 246973 | 9/1998 |
| JP | 10-246973 A * | 9/1998 |
| WO | WO 03/097641 A2 | 11/2003 |
| WO | WO 03/097641 A3 | 11/2003 |
| WO | 2004 011438 | 2/2004 |
| WO | WO 2006/014405 A2 | 2/2006 |
| WO | WO 2006/014405 A3 | 2/2006 |
| WO | WO 2006/122806 A2 | 11/2006 |
| WO | WO 2006/122806 A3 | 11/2006 |
| WO | WO 2006/136553 A1 | 12/2006 |

OTHER PUBLICATIONS

Kitazaki, T.; Ichikawa, T.; Tasaka, A.; Hosono, H.; Matsushita, Y.; Hayashi, R.; Okonogi, K.; Itoh, K. Chem. Pharm. Bull. 48(12) 1935-1946 (2000).*
Ward, R. E.; Meyer, T. Y. Macromolecules 2003, 36, 4368-4373.*
Blinne et al. Makromol. Chem. 177, 1687-1693 (1976).*
Kitazaki,[b] Tomoyuki et al., "Optically Active Antifungal Azoles. X.[1]) Synthesis and Antifungal Activity of N-[4-(Azolyl)phenyl]- and N'-[4-(Azolylmethyl)phenyl]-N'-[(1R,2R)-2-(2,4-difluorophenyl)-2-hydroxy-1-methyl-3-(1H-1,2,4-triazol-1-yl)propyl]-azolones", Chemical and Pharmaceutical Bulletin, vol. 48, No. 12, pp. 1935-1946, (2000).
Ward Rachel E. et al., "o,p-Polyaniline: A New Form of a Classic Conducting Polymer", Macromolecules, vol. 36, No. 12, pp. 4368-4373, (2003).
Johannes Reisch, et al., "Photosynthese des 5-Phenyl-5, 10-dihydro-dibenzo [b, e] [1, 4] diazepin-11-ons aus 1, 2- Diphenyl-indazolon" Archiv der Pharmazie, vol. 309, XP-002605483, 1976, pp. 316-319.

Eleftherios Paul Papadopoulos, "Reactions of isocyanates with 1-cyanothioformanilide", Journal of Organic Chemistry, vol. 44, No. 22, XP-002605484, 1979, pp. 3858-3861.

Roger Ketcham, "Heterocyclic ring-closure reactions. 6. Preparation and further cyclisation reactions of 5-imino-1,3-diphenyl-4-thioxo-2-imidazolidinone and 5-Imino-1,3-diphenyl-2,4-imidazolidinedithione", Journal of Organic Chemistry, vol. 45, No. 19, XP-002605485, 1980, pp. 3748-3750.

Dietrich Dopp, et al., "Reaction of N1, N2-Diarylamidines with Chloranil and 2,3-Dichloro-1,4-naphthoquinone", Journal of Heterocyclic Chemistry, vol. 32, XP-002605486, 1995, pp. 603-610.

Jeffrey T. Kuethe, et al., "Synthesis of Disubstituted Imidazo[4,5-b]Pyridin-2-ones", Journal of Organic Chemistry, vol. 69, No. 22, XP-002605487, 2004, pp. 7752-7754.

Extended Search Report issued Oct. 29, 2010 in EP Application No. 06833152.9.

\* cited by examiner

*Primary Examiner* — Angela Ortiz

*Assistant Examiner* — J. L. Yang

(74) *Attorney, Agent, or Firm* — Oblon, Spivak, McClelland, Maier & Neustadt, L.L.P.

(57) ABSTRACT

An organic compound having excellent heat resistance, an excellent amorphous nature, an excellent ability to transport charges, highly excited singlet and triplet states, and excellent solubility in an organic solvent is an organic compound represented by Formula (I):

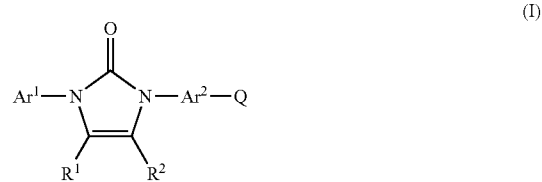

wherein $Ar^1$ represents an optionally-substituted aromatic hydrocarbon group, an optionally-substituted aromatic heterocyclic group, or an optionally-substituted alkyl group; $Ar^2$ represents an optionally-substituted aromatic hydrocarbon group or an optionally-substituted aromatic heterocyclic group; $R^1$ and $R^2$ each represent a hydrogen atom or a substituent, and $R^1$ and $R^2$ may be bonded to each other to form a ring; and Q is represented by Formula (I-1) or (I-2):

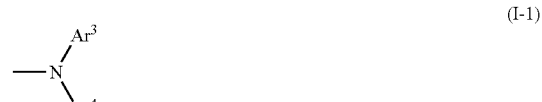

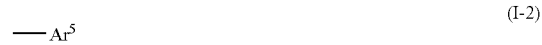

wherein $Ar^3$ to $Ar^5$ each represent an optionally-substituted aromatic hydrocarbon group or an optionally-substituted aromatic heterocyclic group, and $Ar^3$ and $Ar^4$ may be bonded to each other to form a ring.

19 Claims, 4 Drawing Sheets

ORGANIC COMPOUND, CHARGE-TRANSPORTING MATERIAL, COMPOSITION FOR CHARGE-TRANSPORTING MATERIAL AND ORGANIC ELECTROLUMINESCENT DEVICE

This application is a 371 of PCT/JP2006/323330 filed Nov. 22, 2006.

FIELD OF THE INVENTION

The present invention relates to a novel organic compound, a charge-transporting material composed of the organic compound, and a composition for charge-transporting material including the charge-transporting material.

The present invention also relates to a high-brightness high-efficiency long-life organic electroluminescent device including the charge-transporting material composed of the novel organic compound.

BACKGROUND OF THE INVENTION

Electroluminescent devices including organic thin films have been developed. Typically, electroluminescent devices each including an organic thin film, i.e., organic electroluminescent devices, each have an anode, a cathode, and an organic layer including at least a light-emitting layer and provided between the electrodes, on a substrate. The organic layer may include a hole-injection layer, a hole-transport layer, a hole-inhibition layer, an electron-transport layer, an electron-injection layer, and the like in addition to the light-emitting layer. Typically, organic electroluminescent devices each include these layers stacked on top of one another. Hitherto, organic electroluminescent devices have utilized fluorescent emission. To increase light-emission efficiency of devices, attempts have been made to utilize phosphorescent emission instead of fluorescent emission. So far, however, even if phosphorescent emission has been utilized, sufficient light-emission efficiency, luminance, and lifetime have not been obtained.

In order to increase the solubility of polyaniline, which is a conductive polymer, Patent Document 1 discloses Polymer Compound (C-1) shown below.

However, polymer materials such as Compound (C-1) have disadvantages as follows:

it is difficult to control the degree of polymerization and molecular-weight distribution of a polymer materials;

degradation due to terminal residues occurs during continuous driving; and impurities are contained therein because the materials are difficult to purify.

To induce charge transportability in Compound (C-1), it is necessary to dope a protonic acid after oxidation. It is speculated that Compound (C-1) as a charge-transporting material for an organic electroluminescent device has disadvantages because the doped protonic acid and counter anions may diffuse.

Patent Document 1 discloses Compound (C-2) shown below as a model compound of Compound (C-1).

[Chem. 2]

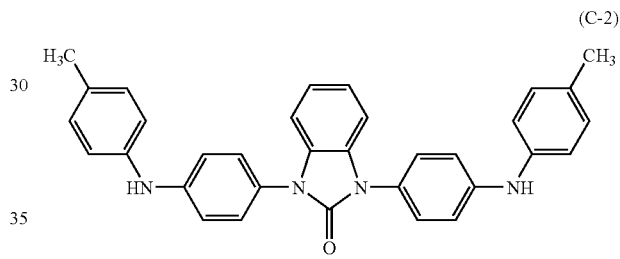

However, Compound (C-2) has secondary amine moieties and thus has inferior heat resistance and a poor amorphous nature. Hence, an organic thin film containing Compound (C-2) has disadvantages in that the film readily deteriorates due to crystallization, aggregation, and the like. Furthermore, Compound (C-2) disadvantageously has inferior charge transportability because the HOMO is localized at the secondary amine moieties.

[Chem. 1]

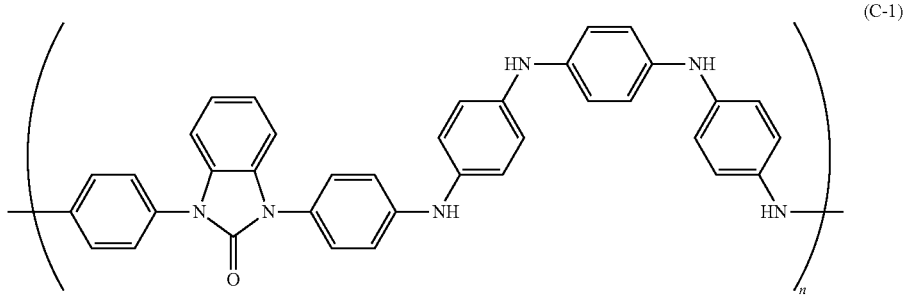

Patent Document 1 proposes that Compound (C-3) be used as a charge-transporting material for an electrophotographic photoreceptor.

[Chem. 3]

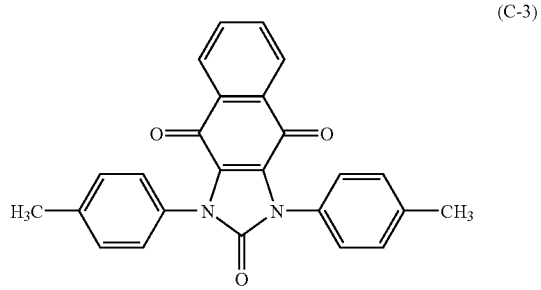

(C-3)

However, compounds such as Compound (C-3) have low heat resistance because each of the groups bonded to the nitrogen atoms of the 1,3-dihydroimidazol-2-one ring has only a single aromatic ring. Thus, compounds such as Compound (C-3) may be disadvantageous when the compounds are used as the charge-transporting materials for organic electroluminescent devices.

Accordingly, it is desirable to provide a material having an excellent ability to transport charges in addition to excellent heat resistance and an excellent amorphous nature.

[Patent Document 1] Japanese Unexamined Patent Application Publication No. 10-246973

[Non-Patent Document 1] Macromolecules 2003, 36, p.p. 4368-4373

DISCLOSURE OF INVENTION

It is an object of the present invention to provide a charge-transporting material having excellent heat resistance, an excellent amorphous nature, and an excellent ability to transport charges, a composition for forming a high-brightness high-efficiency long-life organic electroluminescent device, and an organic electroluminescent device including the composition.

The present invention provides an organic compound represented by Formula (I), a charge-transporting material composed of the compound, a charge-transporting material, represented by Formula (II-2), for an organic electroluminescent device, and a composition for charge-transporting material comprising the material.

The present invention provides an organic electroluminescent device including an anode, a cathode, and a light-emitting layer provided between the electrodes, on a substrate, wherein the organic electroluminescent device includes a layer containing the charge-transporting material.

[Chem. 4]

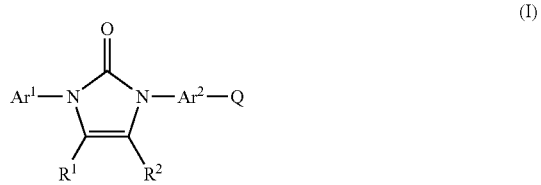

(I)

$Ar^1$ represents an optionally-substituted aromatic hydrocarbon group, an optionally-substituted aromatic heterocyclic group, or an optionally-substituted alkyl group.

$Ar^2$ represents an optionally-substituted aromatic hydrocarbon group or an optionally-substituted aromatic heterocyclic group.

$R^1$ and $R^2$ each independently represent a hydrogen atom or a substituent. $R^1$ and $R^2$ may be bonded to each other to form a ring.

Q is represented by Formula (I-1) or (I-2):

[Chem. 5]

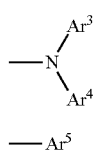

(I-1)

(I-2)

$Ar^3$ to $Ar^5$ each independently represent an optionally-substituted aromatic hydrocarbon group or an optionally-substituted aromatic heterocyclic group. $Ar^3$ and $Ar^4$ may be bonded to each other to form a ring.

[Chem. 6]

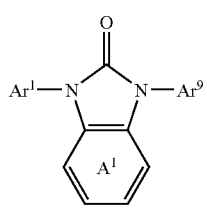

(II-2)

Ring $A^1$ represents an optionally-substituted benzene ring or an optionally-substituted six-membered nitrogen-containing aromatic ring.

$Ar^1$ and $Ar^9$ each independently represent an optionally-substituted aromatic hydrocarbon group or an optionally-substituted aromatic heterocyclic group.

DETAILED DESCRIPTION

Figure 1:
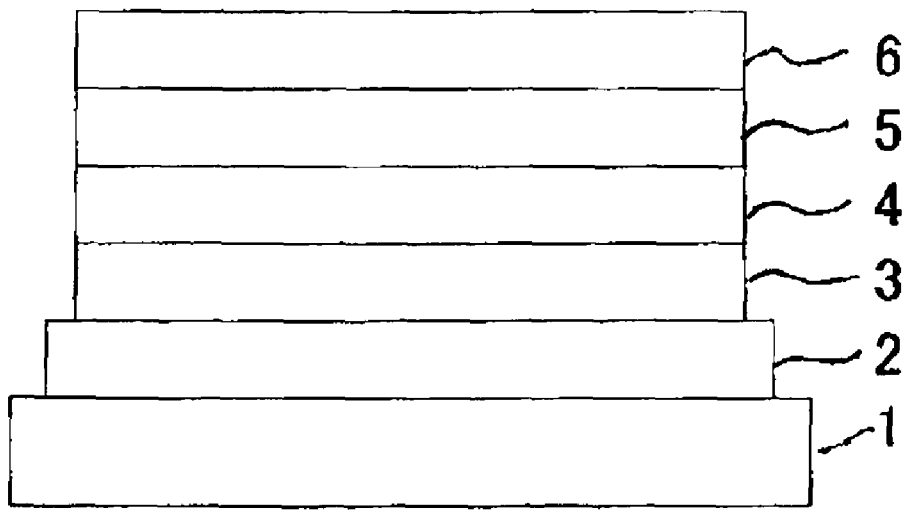
FIG. 1 is a schematic cross-sectional view of an organic electroluminescent device according to an embodiment of the present invention.

The inventors have conducted intensive studies and found the organic compound having the above-described structure. The organic compound has excellent heat resistance, an excellent amorphous nature, an excellent ability to transport charges, highly excited singlet and triplet states, and excellent solubility in an organic solvent.

Thus, an organic electroluminescent device formed by using a charge-transporting material composed of the organic compound and a composition for charge-transporting material including the charge-transporting material composed of the organic compound has high brightness, high efficiency, and long lifetime.

A uniform organic thin film containing a material having an excellent ability to transport charges can be formed by a wet film-forming method with the organic compound of the present invention, the charge-transporting material composed of the compound, and the composition for charge-transporting material containing the material. This facilitates an increase in the area of an organic electroluminescent device. Furthermore, an organic electroluminescent device formed by using the charge-transporting material of the present invention and the composition for charge-transporting material containing the material can emit light at a low voltage and high efficiency.

The charge-transporting material of the present invention can be used in vacuum evaporation and a wet film-forming method because of excellent film formability, an excellent ability to transport charges, excellent luminescence properties, and heat resistance.

Furthermore, the charge-transporting material of the present invention and the composition for the charge-transporting material containing the material can be used as hole-injection materials, hole-transport materials, luminescent materials, host materials, electron-injection materials, electron-transport materials, and the like, in response to the layer structure of a device because of excellent film formability, an excellent ability to transport charges, excellent luminescence properties, and heat resistance.

Accordingly, the organic electroluminescent device of the present invention formed by using the charge-transporting material of the present invention and the composition for charge-transporting material containing the material may be applied to flat-panel displays (e.g., for OA computers and wall-hanging television sets), in-vehicle displays, cellular-phone displays, light sources in which characteristics of a surface illuminant is exploited (e.g., light sources for use in copiers and back light sources for use in liquid crystal displays and instruments), sign boards, and marker lamps. Thus, the organic electroluminescent device has a significant technical value.

The charge-transporting material of the present invention and the composition for charge-transporting material containing the material essentially have excellent redox stability. Thus the material and the composition can be effectively applied not only to the organic electroluminescent device but also to electrophotographic photoreceptors, photoelectric transducers, organic solar cells, organic rectifiers, and the like.

Embodiments of the present invention will be described in detail below. Descriptions of configuration requirements below are examples of embodiments (typical embodiments) of the present invention. The present invention is not limited to these descriptions without departing from the scope of the invention.

[Organic Compound]

An organic compound of the present invention is represented by Formula (I):

[Chem. 7]

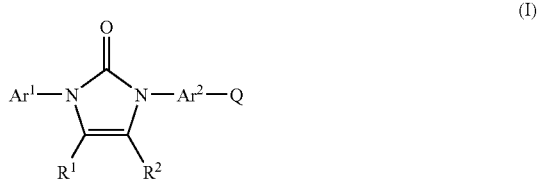

(I)

$Ar^1$ represents an optionally-substituted aromatic hydrocarbon group, an optionally-substituted aromatic heterocyclic group, or an optionally-substituted alkyl group.

$Ar^2$ represents an optionally-substituted aromatic hydrocarbon group or an optionally-substituted aromatic heterocyclic group.

$R^1$ and $R^2$ each independently represent a hydrogen atom or a substituent. $R^1$ and $R^2$ may be bonded to each other to form a ring.

Q is represented by Formula (I-1) or (I-2):

[Chem. 8]

(I-1)

(I-2)

$Ar^3$ to $Ar^5$ each independently represent an optionally-substituted aromatic hydrocarbon group or an optionally-substituted aromatic heterocyclic group. $Ar^3$ and $Ar^4$ may be bonded to each other to form a ring.

[1] Structural Feature

The organic compound of the present invention has a five-membered-ring structure (1,3-dihydroimidazol-2-one) including a urea bond (—NR—CO—NR'—) and thus has proper polarity, a highly amorphous nature, and high heat resistance. Therefore, the organic compound is soluble in various organic solvents. Hence, it is possible to form an organic thin film that is amorphous and is not easily crystallized. The structure is a rigid planar structure. Thus, the organic compound of the present invention has highly excited singlet and triplet states. Furthermore, the organic compound of the present invention has a tertiary amine moiety (—$Ar^2$—N($Ar^3$)—$Ar^4$) or two directly bonded aromatic groups (—$Ar^2$—$Ar^5$) in addition to the structure and thus has a further improved ability to transport charges and further improved heat resistance.

[2] Molecular Weight Range

The molecular weight of the organic compound of the present invention is usually 5,000 or less, preferably 3,000 or less, and more preferably 2,000 or less, and usually 300 or more, preferably 500 or more, and more preferably 600 or more.

A molecular weight exceeding the upper limit described above may result in difficulty in purification due to an increase in the molecular weight of impurities. A molecular weight of less than the lower limit described above may significantly reduce heat resistance due to reductions in glass transition temperature, melting point, vaporization temperature, and the like.

[3] Physical Properties

The organic compound of the present invention usually has a glass transition temperature of 40° C. or higher. From the viewpoint of achieving good heat resistance, the glass transition temperature is preferably 80° C. or higher and more preferably 110° C. or higher.

The organic compound of the present invention usually has a vaporization temperature of 300° C. to 800° C.

The energy difference between the excited triplet state and the ground state of the organic compound of the present invention is usually in the range of 2.0 eV to 4.0 eV. From the viewpoint of increasing the efficiency of an organic electroluminescent device utilizing phosphorescent emission, the energy difference between the excited triplet state and the ground state is preferably 2.3 eV or more, more preferably 2.6 eV or more, and still more preferably 2.9 eV or more.

An example of a method of obtaining the energy difference between the excited triplet state and the ground state (lowest triplet excitation energy) is as follows.

A solution of a sample compound dissolved in a spectroscopically purified solvent (e.g., 2-methyltetrahydrofuran) is charged into a tubular quartz cell, cooling the solution to 77 K with liquid nitrogen. Then photoluminescence is measured. The lowest triplet excitation energy is determined from the phosphorescent emission (0.0 transition peak shape) of the maximum energy. The separation between phosphorescent emission and fluorescent emission is achieved by delaying the photoluminescence measurement start time until after the incidence of excitation light. The photoluminescence is measured by irradiating the sample compound with light, as excitation light, from a $N_2$ laser light source (wavelength 337 nm) in response to the absorption of light by the material.

[4] $R^1$ and $R^2$ $R^1$ and $R^2$ each independently represent a hydrogen atom or any substituent. $R^1$ and $R^2$ may be bonded to each other to form a ring.

Examples of the substituent include organic groups described below. Each of the groups preferably has a molecular weight of 500 or less. Specific examples thereof include:

optionally-substituted alkyl groups (preferably, linear or branched alkyl groups each having 1 to 8 carbon atoms, e.g., methyl, ethyl, n-propyl, 2-propyl, n-butyl, isobutyl, and tert-butyl groups), optionally-substituted alkenyl groups (preferably, alkenyl groups each having 2 to 9 carbon atoms, e.g., vinyl, allyl, and 1-butenyl groups), optionally-substituted alkynyl groups (preferably, alkynyl groups each having 2 to 9 carbon atoms, e.g., ethynyl and propargyl groups), optionally-substituted aralkyl groups (preferably, aralkyl groups each having 7 to 15 carbon atoms, e.g., benzyl groups), optionally-substituted amino groups (preferably, alkylamino groups each having at least one optionally-substituted alkyl group with 1 to 8 carbon atoms (e.g., methylamino, dimethylamino, diethylamino, and dibenzylamino groups), optionally-substituted arylamino groups each having an aromatic hydrocarbon group with 6 to 12 carbon atoms (e.g., phenylamino, diphenylamino, and ditolylamino groups), optionally-substituted heteroarylamino groups each having a 5- or 6-membered aromatic heterocyclic ring (e.g., pyridylamino, thienylamino, and dithienylamino groups), optionally-substituted acylamino groups each having an acyl group with 2 to 10 carbon atoms (e.g., acetylamino and benzoylamino groups)], optionally-substituted alkoxy groups (preferably, optionally-substituted alkoxy groups each having 1 to 8 carbon atoms, e.g., methoxy, ethoxy, and butoxy groups), optionally-substituted aryloxy groups (preferably, aryloxy groups each having an aromatic hydrocarbon group with 6 to 12 carbon atoms, e.g., phenyloxy, 1-naphthyloxy, and 2-naphthyloxy groups), optionally-substituted heteroaryloxy groups (preferably, heteroaryloxy groups each having a 5- or 6-membered aromatic heterocyclic group, e.g., pyridyloxy and thienyloxy groups), optionally-substituted acyl groups (preferably, optionally-substituted acyl groups each having 2 to 10 carbon atoms, e.g., formyl, acetyl, and benzoyl groups), optionally-substituted alkoxycarbonyl groups (preferably, optionally-substituted alkoxycarbonyl groups each having 2 to 10 carbon atoms, e.g., methoxycarbonyl and ethoxycarbonyl groups), optionally-substituted aryloxycarbonyl groups (preferably, optionally-substituted aryloxycarbonyl groups each having 7 to 13 carbon atoms, e.g., a phenoxycarbonyl group), optionally-substituted alkylcarbonyloxy groups (preferably, optionally-substituted alkylcarbonyloxy groups each having 2 to 10 carbon atoms, e.g., an acetoxy group), halogen atoms (in particular, a fluorine atom and a chlorine atom), carboxyl groups, cyano groups, hydroxyl groups, mercapto groups, optionally-substituted alkylthio groups (preferably, alkylthio groups each having 1 to 8 carbon atoms, e.g., a methylthio group and an ethylthio group), optionally-substituted arylthio groups (preferably, arylthio groups each having 6 to 12 carbon atoms, e.g., a phenylthio group and 1-naphthylthio group), optionally-substituted sulfonyl groups (e.g., a mesyl group and a tosyl group), optionally-substituted silyl groups (e.g., a trimethylsilyl group and a triphenylsilyl group), optionally-substituted boryl groups (e.g., a dimesitylboryl group), optionally-substituted phosphino groups (e.g., a diphenylphosphino group), optionally-substituted aromatic hydrocarbon groups (such as monovalent groups derived from 5- or 6-membered monocycles or 2- to 5-fused rings, for example, a benzene ring, a naphthalene ring, an anthracene ring, a phenanthrene ring, a perylene ring, a tetracene ring, a pyrene ring, a benzpyrene ring, a chrysene ring, a triphenylene ring, and a fluoranthene ring), and optionally-substituted heterocyclic groups (such as monovalent groups derived from 5- or 6-membered monocycles or 2- to 4-fused rings, for example, a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofurane ring, a thienofuran ring, a benzoisoxazole ring, a benzoisothiazole ring, a benzoimidazole ring, a pyridine ring, a pyrazine ring, a pyridazine ring, a pyrimidine ring, a triazine ring, a quinoline ring, an isoquinoline ring, a cinnoline ring, a quinoxaline ring, a benzimidazole ring, a perimidine ring, a quinazoline ring, an imidazolinone ring, and a benzoimidazolinone ring).

In the case where the above-described substituent further has a substituent, examples of the substituent include the substituents exemplified above.

From the viewpoint of improving electrochemical durability and heat resistance, each of $R^1$ and $R^2$ preferably represents an optionally-substituted aromatic hydrocarbon group, more preferably an optionally-substituted phenyl group, and still more preferably an unsubstituted phenyl group or a mono- or di-substituted phenyl group.

From the viewpoint of further improving solubility and amorphous nature, each of $R^1$ and $R^2$ preferably represents an optionally-substituted alkyl group, more preferably an alkyl group having 1 to 4 carbon atoms, e.g., a methyl group, an ethyl group, a n-propyl group, a 2-propyl group, a n-butyl group, an isobutyl group, or a tert-butyl group, and still more preferably a methyl group, an ethyl group, or a n-propyl group.

From the viewpoint of preventing a reduction in triplet excited level, each of $R^1$ and $R^2$ preferably represents a hydrogen atom.

From the viewpoint of further improving heat resistance, preferably, $R^1$ and $R^2$ are bonded to each other to form a ring. Examples of the organic compound represented by Formula (I) when $R^1$ and $R^2$ are bonded to each other to form a ring are shown below. The present invention is not limited thereto. Hereinafter, examples of R include the substituents exemplified as $R^1$ and $R^2$. Alternatively, R represents a hydrogen atom.

[Chem. 9]

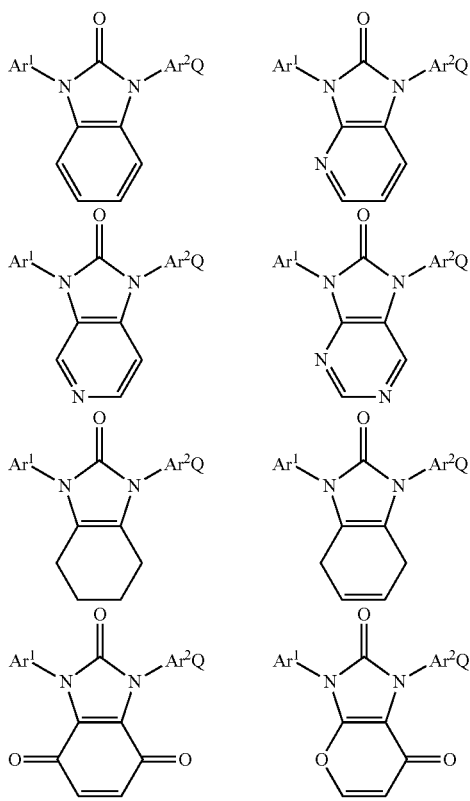

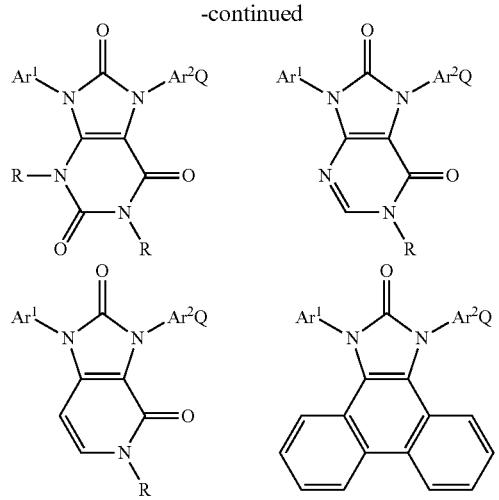

From the viewpoint of improving electrochemical durability and the prevention of a reduction in triplet excited level, preferably, $R^1$ and $R^2$ are bonded to each other to form a benzene ring or a six-membered nitrogen-containing aromatic ring. That is, the organic compound of the present invention is preferably represented by Formula (II) shown below.

[Chem. 10]

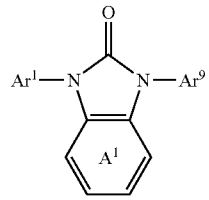

(II)

$Ar^1$, $Ar^2$, and Q are defined the same as in Formula (I).

Ring $A^1$ represents an optionally-substituted benzene ring or an optionally-substituted six-membered nitrogen-containing aromatic ring.

Examples of the six-membered nitrogen-containing aromatic ring as ring $A^1$ include a pyridine ring, a pyrazine ring, a pyrimidine ring, a pyridazine ring, and a triazine ring. In particular, a pyridine ring is preferred.

Examples of a substituent on ring $A^1$ include the substituents exemplified as $R^1$ and $R^2$. Preferred substituents are the same as the preferred substituents as $R^1$ and $R^2$.

[5] $Ar^1$ and $Ar^2$ $Ar^1$ in the organic compound of the present invention represents an aromatic hydrocarbon group that may have any substituent, an aromatic heterocyclic group that may have any substituent, or an alkyl group that may have any substituent. $Ar^2$ represents an aromatic hydrocarbon group that may have any substituent or an aromatic heterocyclic group that may have any substituent.

Examples of the substituents that may be provided on $Ar^1$ and $Ar^2$ include the substituents exemplified as $R^1$ and $R^2$. Each of the substituents on $Ar^1$ and $Ar^2$ may have a structure in which a plurality of substituents exemplified as $R^1$ and $R^2$ are linked. These substituents may be bonded to adjacent groups to form a ring. $Ar^1$ including the substituent preferably has a molecular weight of 3,000 or less and more preferably 1,000 or less. $Ar^2$-Q including the substituent preferably has a molecular weight of 3,000 or less and more preferably 1,000 or less.

Each of the substituents that may be provided on $Ar^1$ and $Ar^2$ is preferably an optionally-substituted aromatic hydrocarbon group, more preferably an optionally-substituted phenyl group, and still more preferably an unsubstituted phenyl group or a mono- or di-substituted phenyl group, from the viewpoint of improving heat resistance.

Each of the substituents that may be provided on $Ar^1$ and $Ar^2$ is preferably an optionally-substituted alkyl group, more preferably an alkyl group having 1 to 4 carbon atoms, e.g., a methyl group, an ethyl group, a n-propyl group, 2-propyl group, a n-butyl group, an isobutyl group, a sec-butyl group, or a tert-butyl group, and still more preferably a methyl group or an ethyl group, from the viewpoint of further improving solubility and an amorphous nature.

Each of the substituents that may be provided on $Ar^1$ and $Ar^2$ is preferably a group derived from a 1,3-dihydroimidazol-2-one ring from the viewpoints of preventing reductions in singlet and triplet excited levels and further improving heat resistance and the ability to transport charges.

Examples of the aromatic hydrocarbon group that may be applied to $Ar^1$ and $Ar^2$ include groups derived from 6-membered monocycles or 2- to 5-fused rings, e.g., a benzene ring, a naphthalene ring, an anthracene ring, a phenanthrene ring, a perylene ring, a tetracene ring, a pyrene ring, a benzpyrene ring, a chrysene ring, a triphenylene ring, an acenaphthene ring, and a fluoranthene ring.

Examples of the aromatic heterocyclic group that may be applied to $Ar^1$ and $Ar^2$ include groups derived from 5- or 6-membered monocycles or 2- to 4-fused rings, e.g., a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofurane ring, a thienofuran ring, a benzoisoxazole ring, a benzoisothiazole ring, a benzoimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazolinone ring, and an azulene ring.

Examples of the alkyl group that may be applied to $Ar^1$ include alkyl groups having 1 to 4 carbon atoms, e.g., methyl, ethyl, n-propyl, 2-propyl, n-butyl, isobutyl, a sec-butyl group, and a tert-butyl group.

$Ar^1$ preferably represents a group derived from an optionally-substituted benzene ring, a group derived from an optionally-substituted pyridine ring, or a group in which a plurality (e.g., 2 to 10) of optionally-substituted benzene rings or optionally-substituted pyridine rings are linked (e.g., a biphenyl group, a terphenyl group, a phenylpyridyl group, a bipyridyl group, or a terpyridyl group), from the viewpoint of preventing a reduction in triplet excited level.

$Ar^1$ is preferably the same as —$Ar^2$-Q from the viewpoints of ease of synthesis and a tendency to increase the triplet excited level.

$Ar^1$ is preferably a group different from —$Ar^2$-Q from the viewpoint of improving solubility.

$Ar^2$ preferably represents a group derived from an optionally-substituted benzene ring, a group derived from an optionally-substituted pyridine ring, or a divalent group in which a plurality (e.g., 2 to 10) of optionally-substituted benzene rings or optionally-substituted pyridine rings are linked (e.g., a divalent group derived from biphenyl, terphenyl, bipyridyl, terpyridyl, phenylpyridine, diphenylpyridine, or dipyridylbenzene), from the viewpoint of preventing a reduction in triplet excited level.

More preferably, $Ar^2$ represents a p-phenylene group, a 4,4'-biphenylene group, a 4,3'-biphenylene group, or a 3,4'-biphenylene group, from the viewpoint of further improving electrochemical durability.

More preferably, $Ar^2$ represents a m-phenylene group or a 3,3'-biphenylene group from the viewpoint of further improving solubility.

$Ar^2$ preferably contains a pyridine ring and more preferably represents a pyridinediyl group or a divalent group derived from bipyridyl, terpyridyl, phenylpyridine, diphenylpyridine, or dipyridylbenzene, from the viewpoint of further improving charge (electron) transportability.

Preferably, both of $Ar^1$ and $Ar^2$ represent groups each derived from a benzene ring from the viewpoints of achieving good solubility and heat resistance, and preventing a reduction in triplet excited level.

That is, the organic compound of the present invention is preferably represented by Formula (III) shown below.

[Chem. 11]

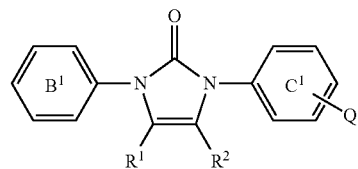

(III)

$R^1$, $R^2$, and Q are defined the same as in Formula (I).
Ring $B^1$ represents an optionally-substituted benzene ring.
Ring $C^1$ represents a benzene ring that may have a substituent in addition to Q.

Examples and preferred examples of substituents that may be provided on ring $B^1$ are the same as the substituents that may be provided on $Ar^1$. Examples and preferred examples of substituents that may be provided on ring $C^1$ are the same as the substituents that may be provided on $Ar^2$.

Preferably, both of $Ar^1$ and $Ar^2$ represent groups each derived from a pyridine ring from the viewpoints of achieving good charge transportability and heat resistance, and preventing a reduction in triplet excited level.

That is, the organic compound of the present invention is represented by Formula (III-2) shown below.

[Chem. 12]

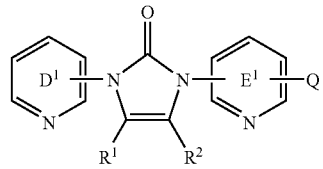

(III-2)

$R^1$, $R^2$, and Q are defined the same as in Formula (I).
Ring $D^1$ represents an optionally-substituted pyridine ring.
Ring $E^1$ represents a pyridine ring that may have a substituent in addition to Q.

Examples and preferred examples of substituents that may be provided on ring $D^1$ are the same as the substituents that may be provided on $Ar^1$. Examples and preferred examples of substituents that may be provided on ring $E^1$ are the same as the substituents that may be provided on $Ar^2$.

[6] Q

Q in the organic compound of the present invention represents a group selected from Formulae (I-1) and (I-2) shown below.

[Chem. 13]

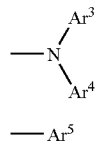

(I-1)

—$Ar^5$ (I-2)

$Ar^3$ to $Ar^5$ each independently represent an optionally-substituted aromatic hydrocarbon group or an optionally-substituted aromatic heterocyclic group. $Ar^3$ to $Ar^5$ may be bonded to each other to form a ring.

Examples of substituents that may be provided on $Ar^3$ to $Ar^5$ include the substituents exemplified as $R^1$ and $R^2$.

Preferred examples of the substituents that may be provided on $Ar^3$ to $Ar^5$ are the same as the preferred examples of the substituents that may be provided on $Ar^1$ and $Ar^2$.

Examples of aromatic hydrocarbon groups and aromatic heterocyclic groups that may be applied to $Ar^3$ to $Ar^5$ are the same as the examples of the aromatic hydrocarbon groups and the aromatic heterocyclic groups that may be applied to $Ar^1$ and $Ar^2$.

Each of $Ar^3$ and $Ar^4$ preferably represents an optionally-substituted aromatic hydrocarbon group, more preferably an optionally-substituted phenyl group, still more preferably an unsubstituted phenyl group or a mono- or di-substituted phenyl group, from the viewpoint of improving electrochemical durability and heat resistance.

From the viewpoint of further improving charge transportability, Q is preferably represented by Formula (I-1).

In Formula (I-1), $Ar^3$ and $Ar^4$ may be bonded to each other to form an optionally-substituted ring. Preferred examples of $Ar^3Ar^4N$— when $Ar^3$ and $Ar^4$ are bonded to each other to form a ring are shown below. Among these, an N-carbazolyl group is more preferred because it has a high triplet excited level.

[Chem. 14]

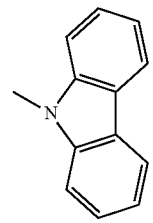 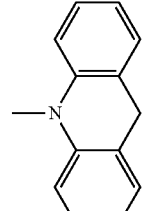

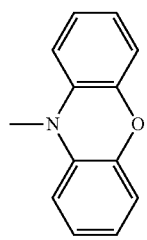 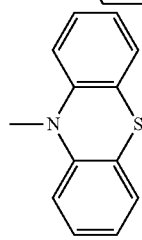

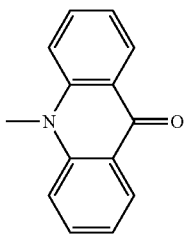 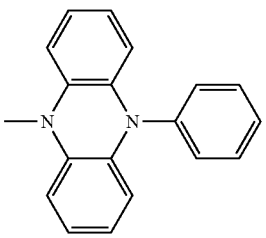

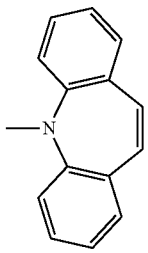 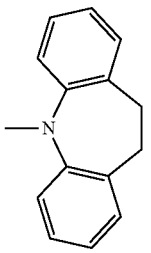

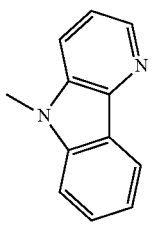 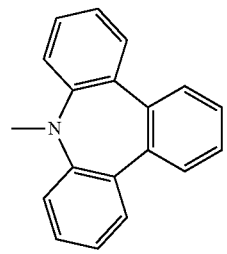

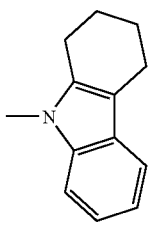 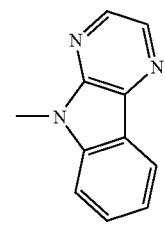

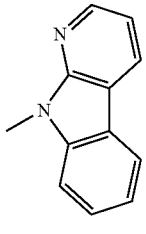 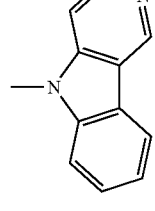

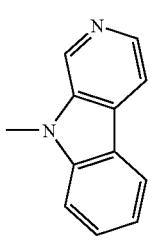 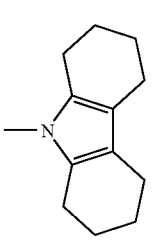

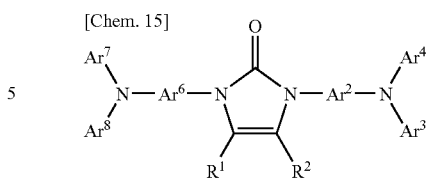

(IV)

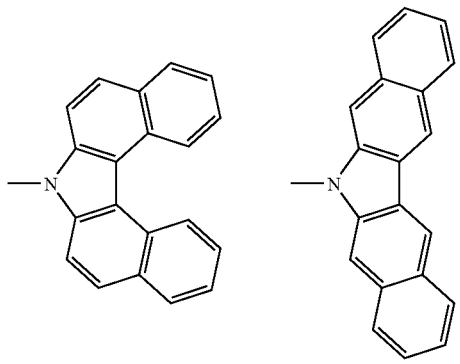

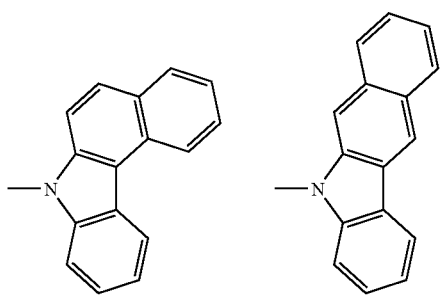

From the viewpoint of improving heat resistance, Q is preferably represented by Formula (I-2).

In Formula (I-2), $Ar^5$ preferably represents a group derived from an optionally-substituted benzene ring or a group in which a plurality (e.g., 2 to 10) of benzene rings are linked (e.g., a biphenylene group or a terphenylene group), from the viewpoint of preventing a reduction in triplet excited level.

[7] Preferred Structure

The organic compound of the present invention is preferably represented by Formula (IV) shown below because it has an excellent ability to transport charges, high electrochemical stability, and a high triplet excited level.

[Chem. 15]

$Ar^2$ to $Ar^4$, $R^1$, and $R^2$ are defined the same as in Formulae (I) and (I-1).

$Ar^6$ to $Ar^8$ each independently represent an optionally-substituted aromatic hydrocarbon group or an optionally-substituted aromatic heterocyclic group. $Ar^7$ and $Ar^8$ may be bonded to each other to form a ring.

Examples and preferred examples of $Ar^6$ are the same as those of $Ar^2$. Examples and preferred examples of $Ar^7$ and $Ar^8$ are the same as those of $Ar^3$ and $Ar^4$, respectively.

From the viewpoint of further improving heat resistance while a high triplet excited level is maintained, the organic compound of the present invention preferably has at least one, more preferably one to six, and still more preferably two to four N-carbazolyl groups represented by Formula (I-3) at the $Ar^1$ moiety, the $Ar^2$-Q moiety, and either $R^1$ moiety or $R^2$ moiety. The carbazolyl group may have a substituent. Preferably, the carbazolyl group is not substituted.

[Chem. 16]

(I-3)

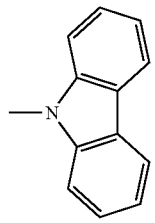

[8] Exemplification

Specific preferred examples of the organic compound of the present invention will be shown below. The present invention is not limited thereto.

[Chem. 17]

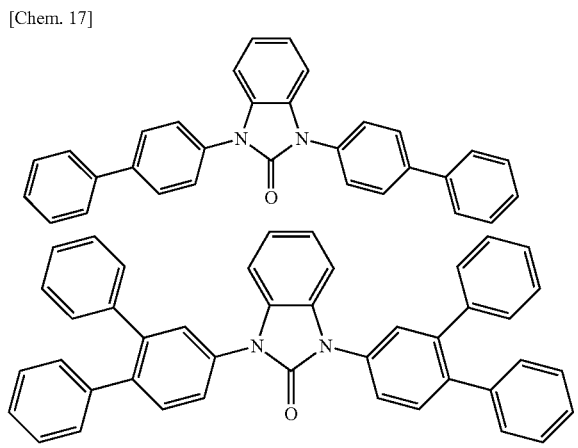

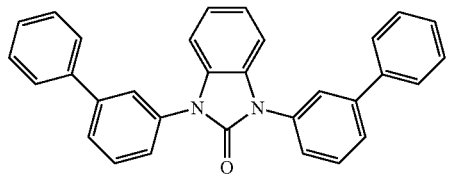

-continued
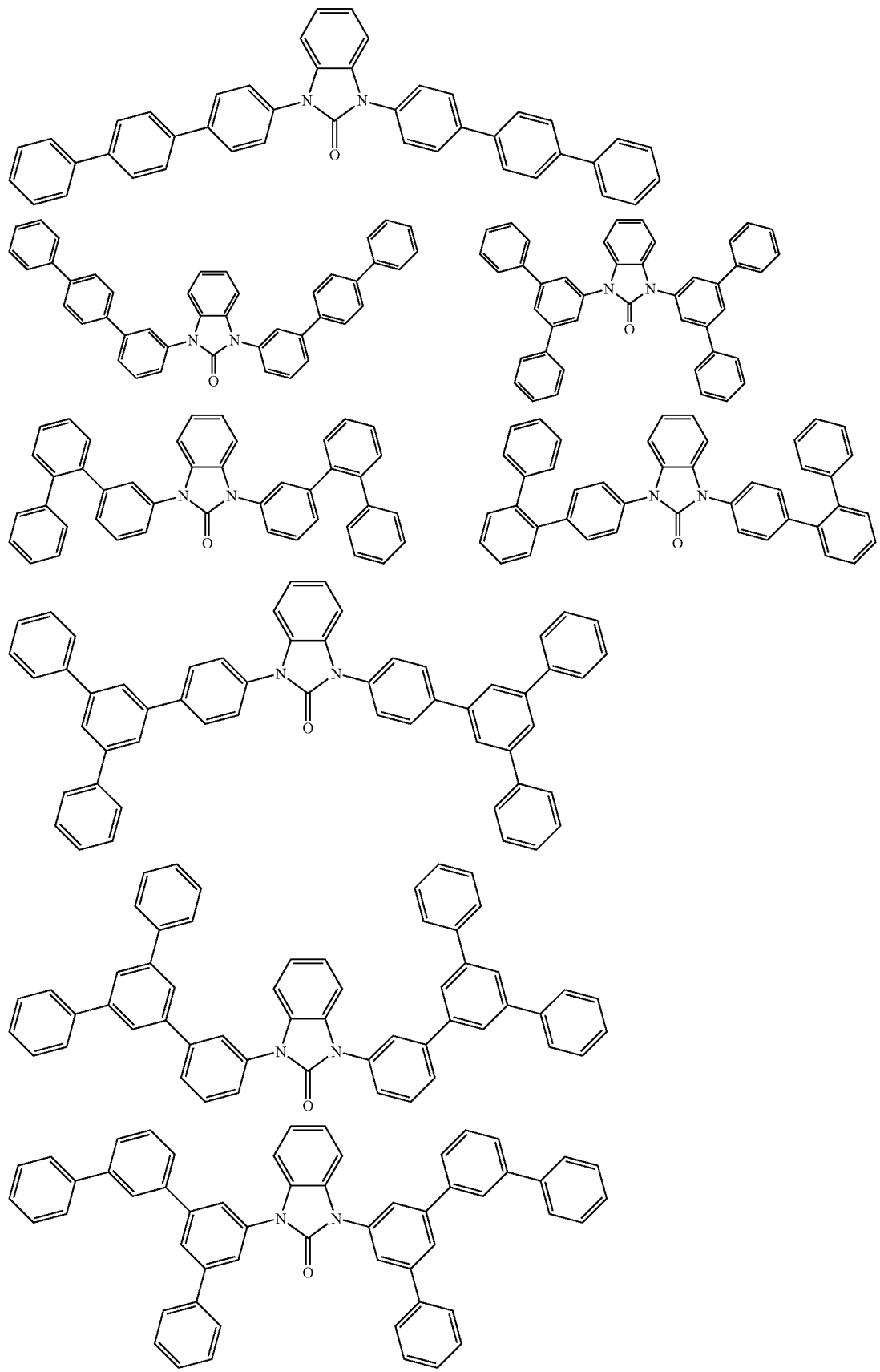

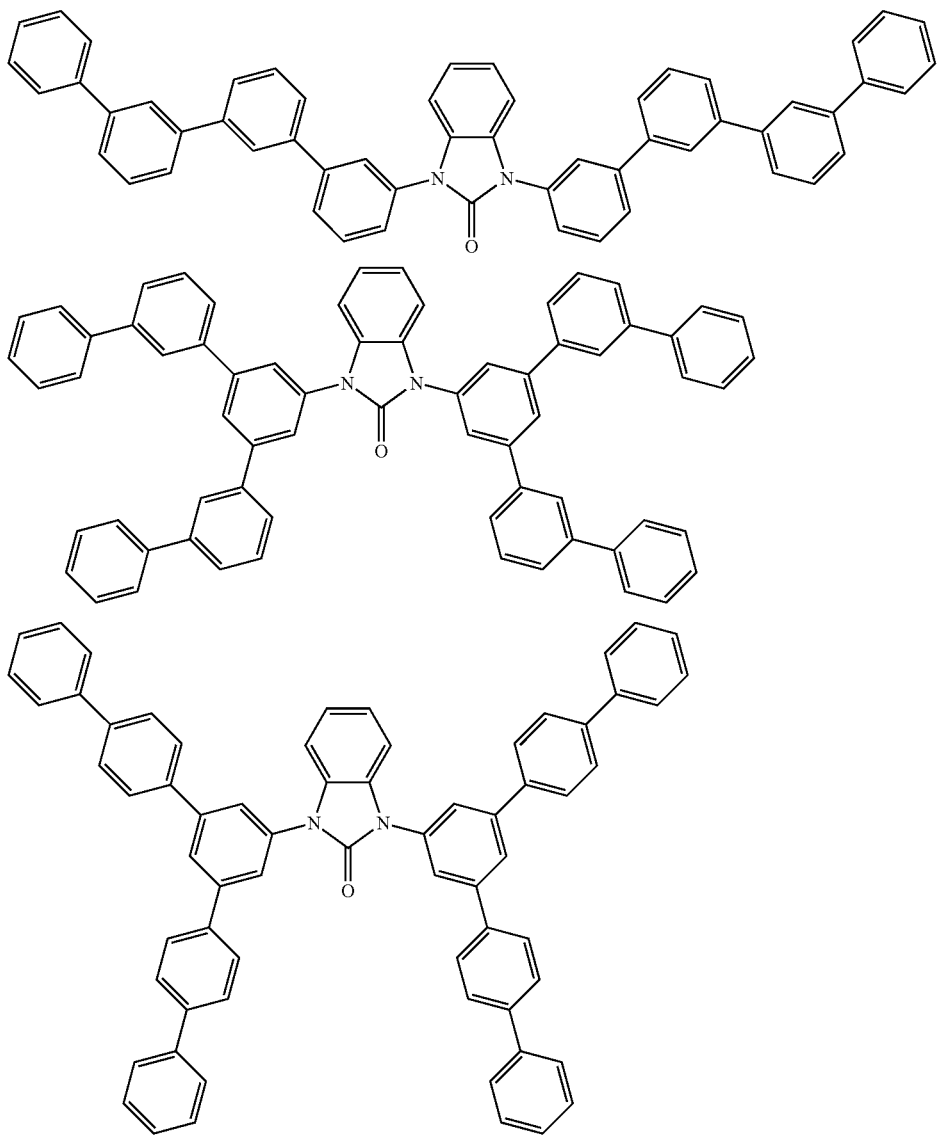
[Chem. 18]
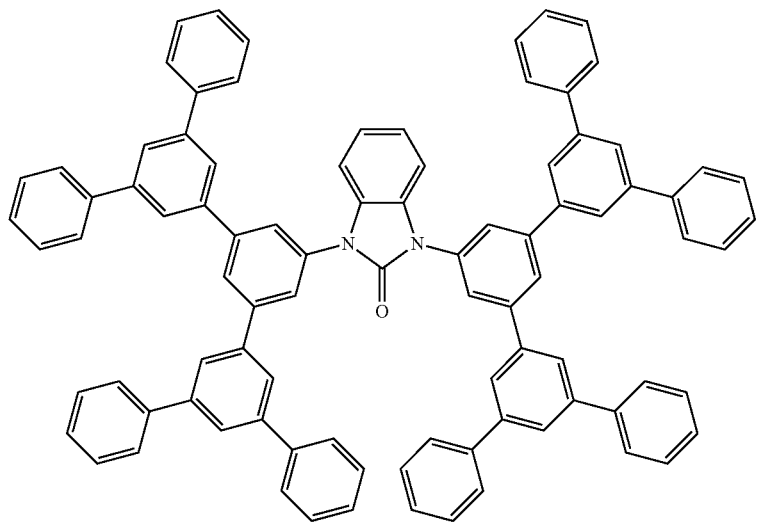

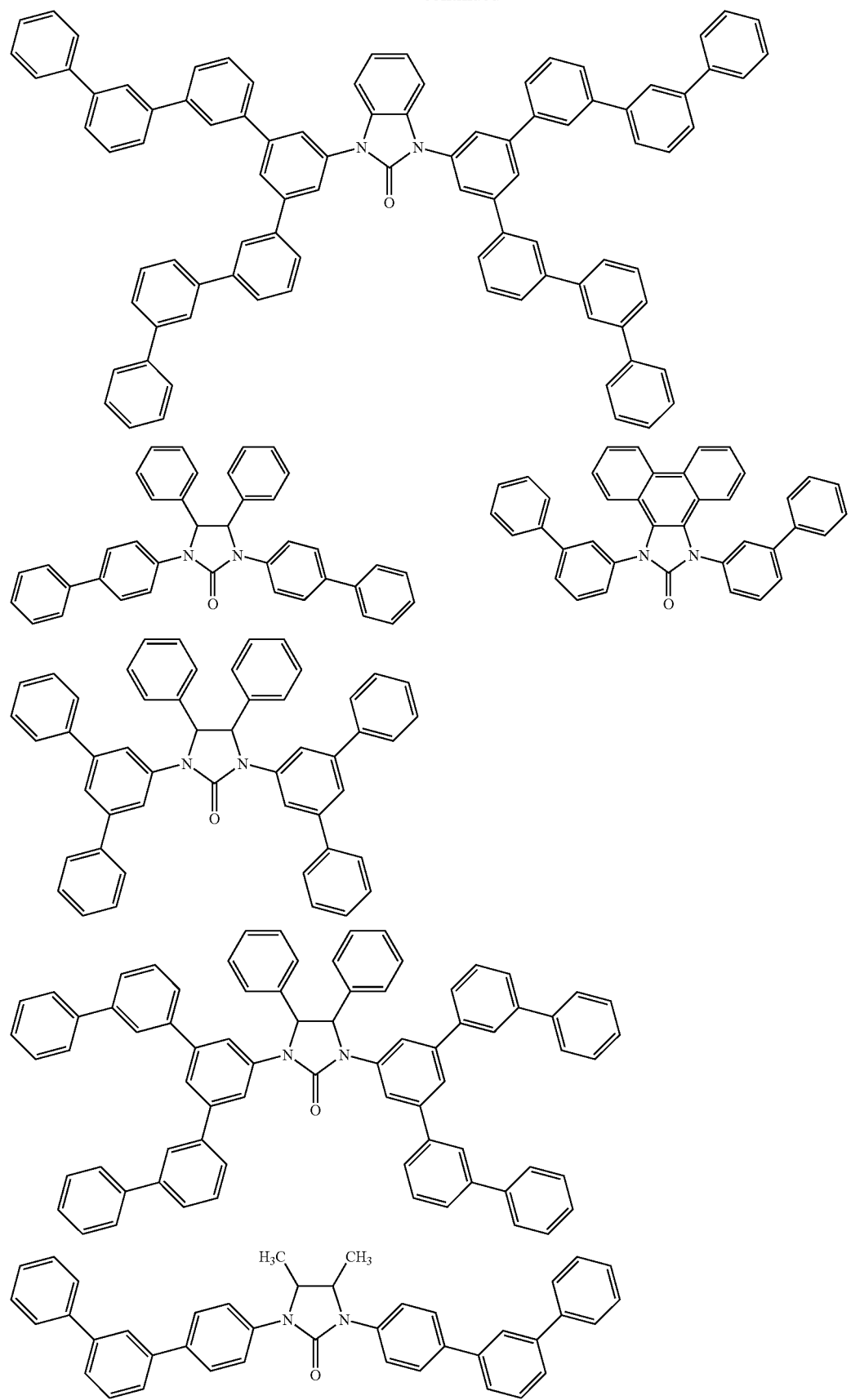

23
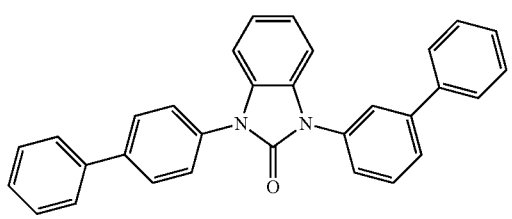
24
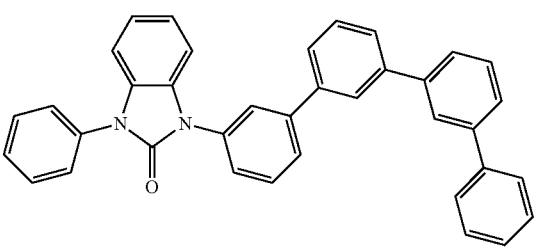
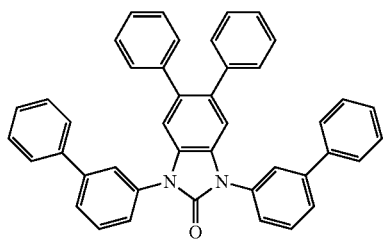
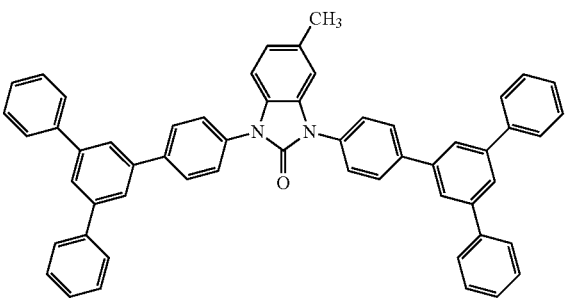
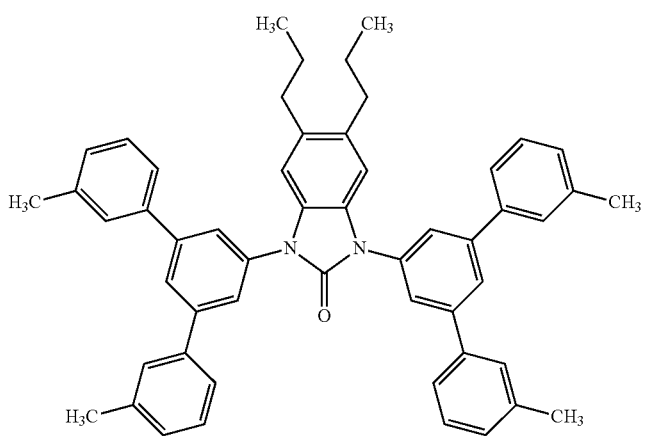
[Chem. 19]
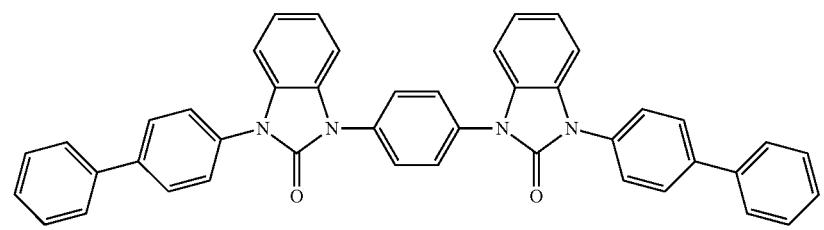
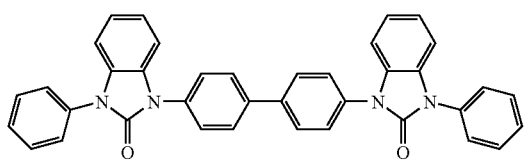
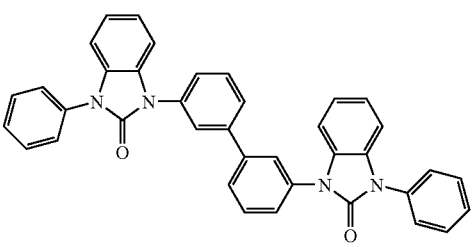
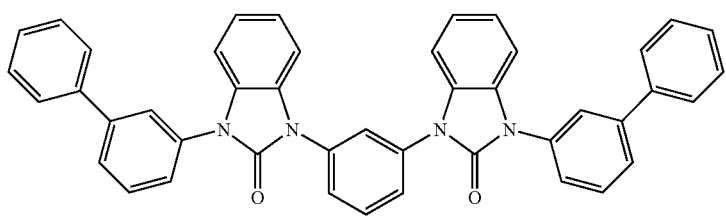

-continued
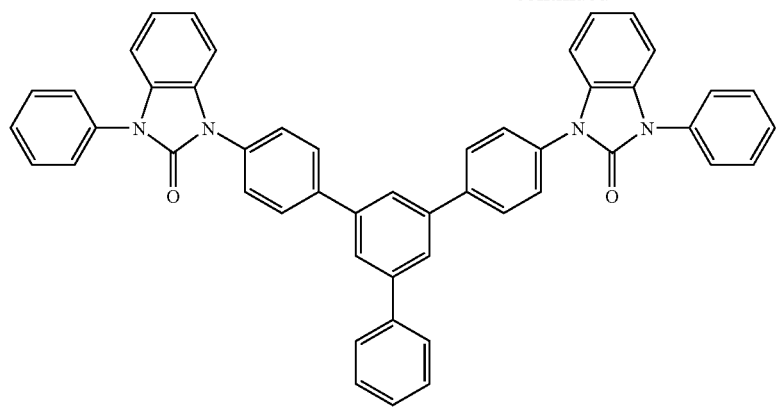
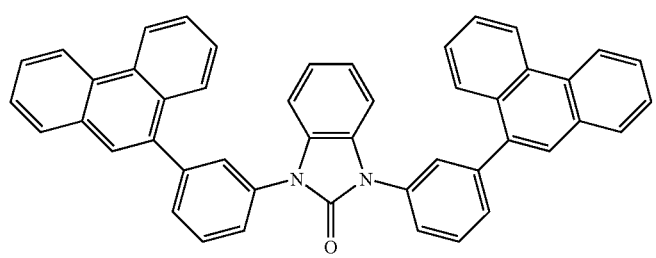
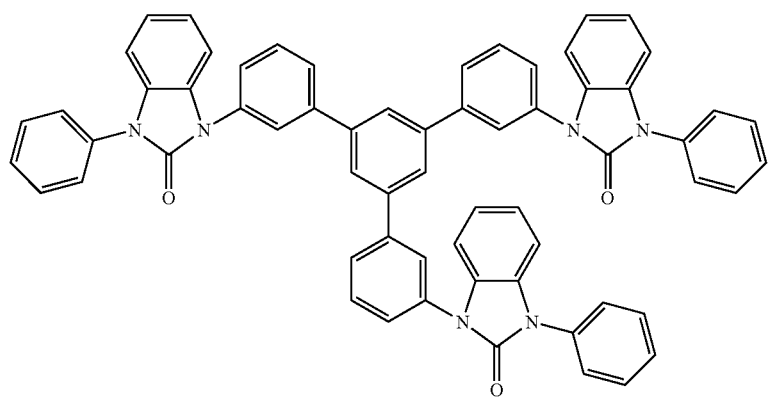
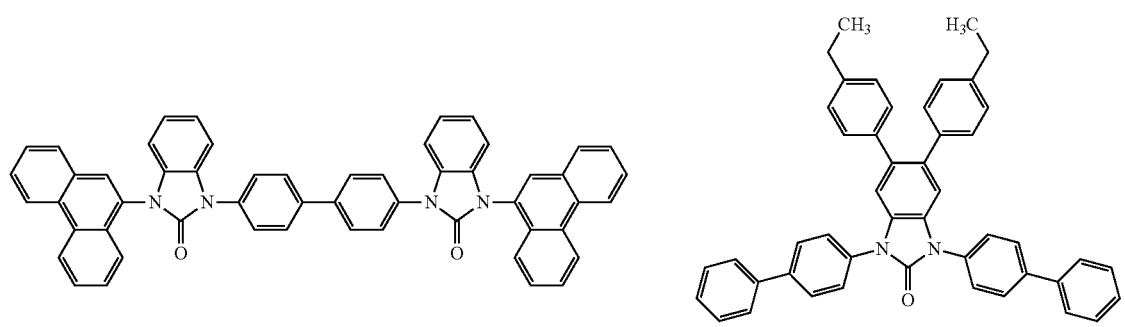
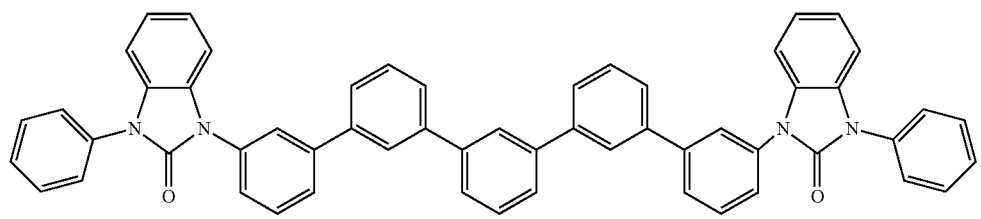

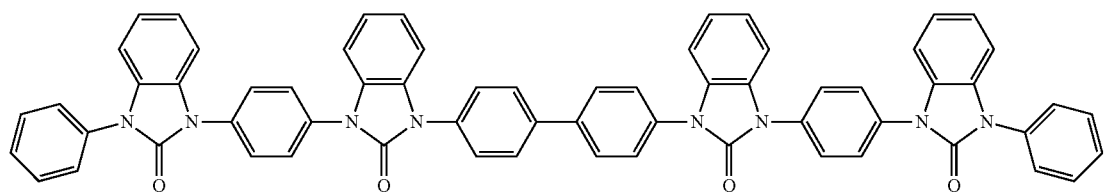
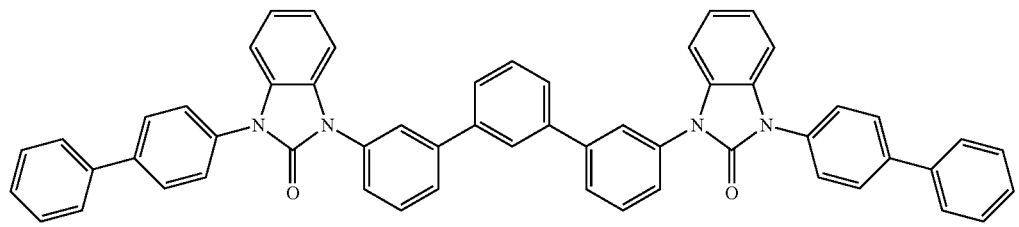
[Chem. 20]
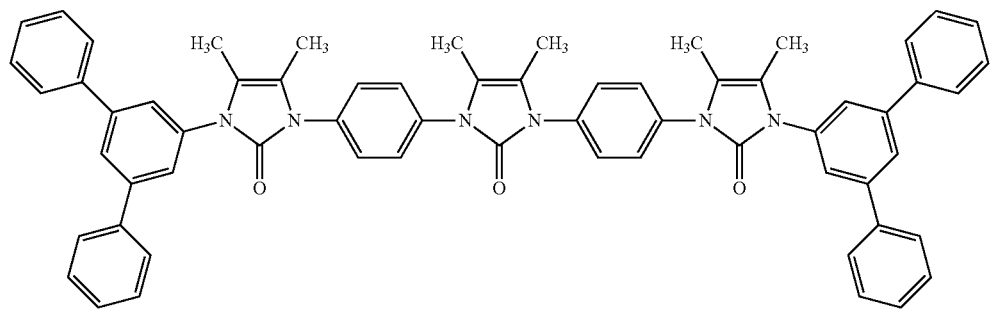
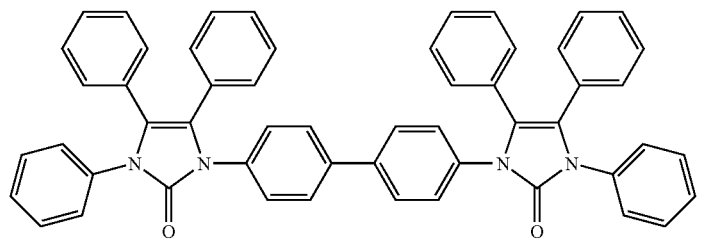
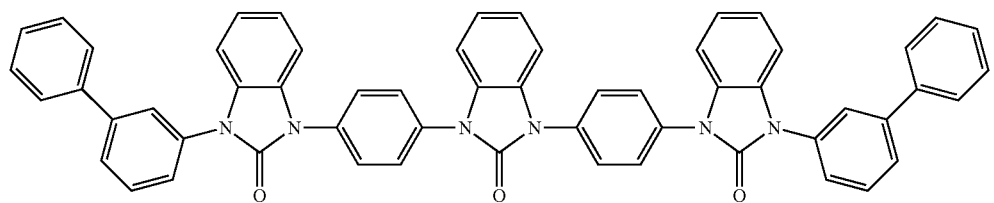
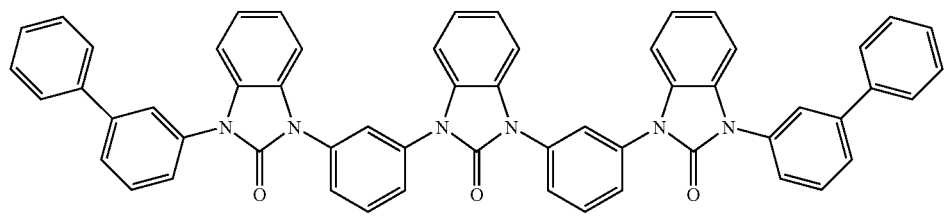

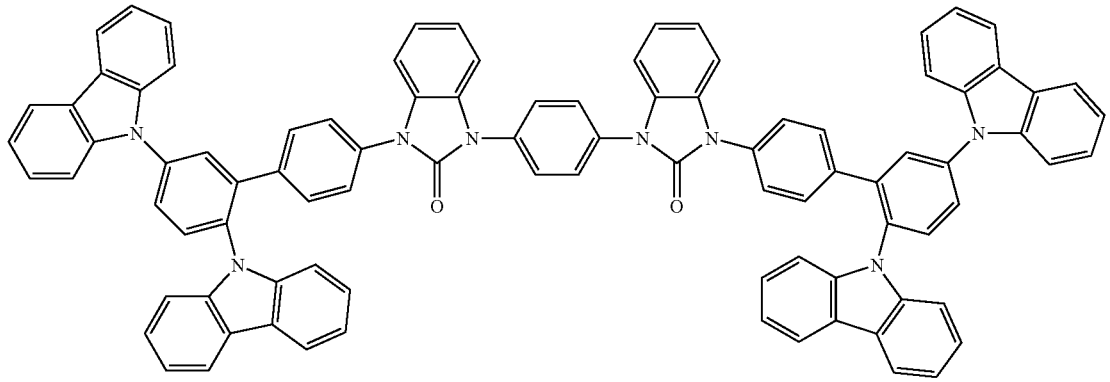
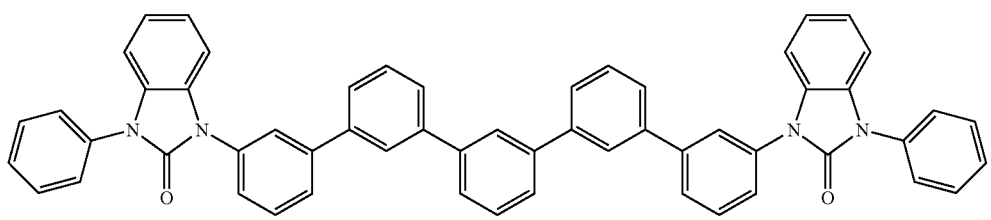
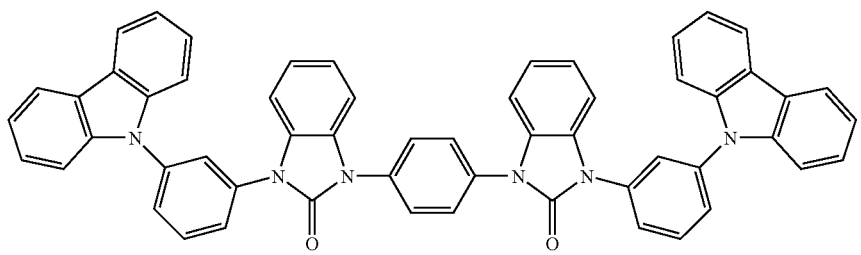
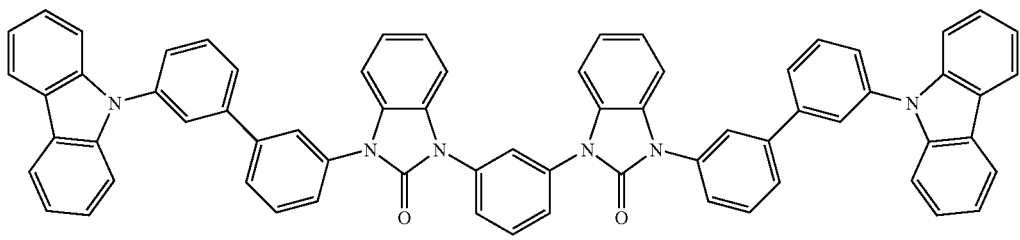
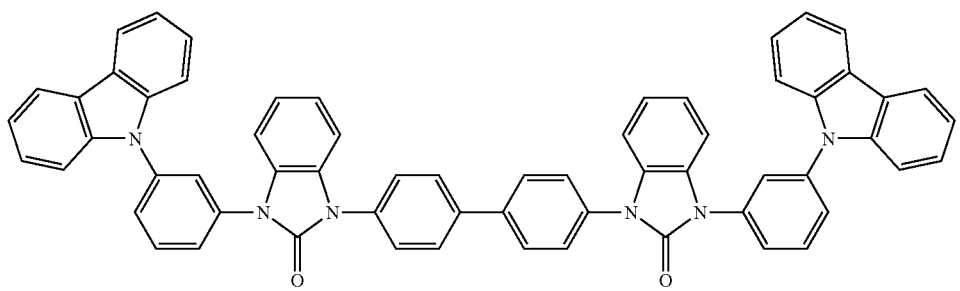

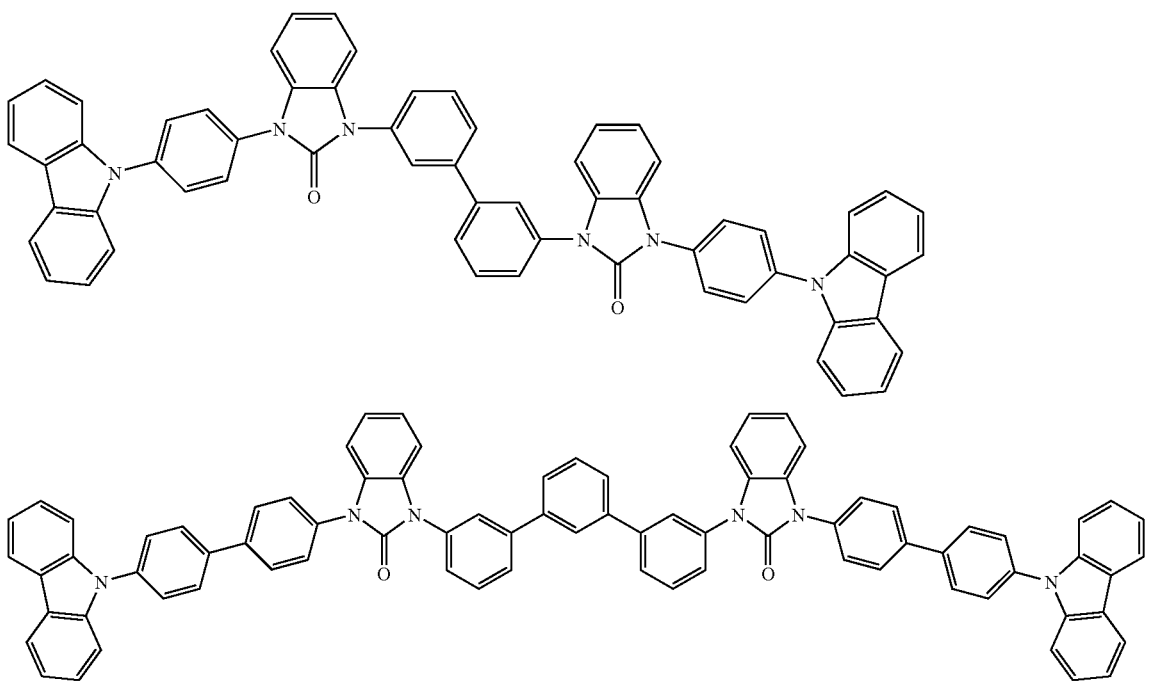
[Chem. 21]
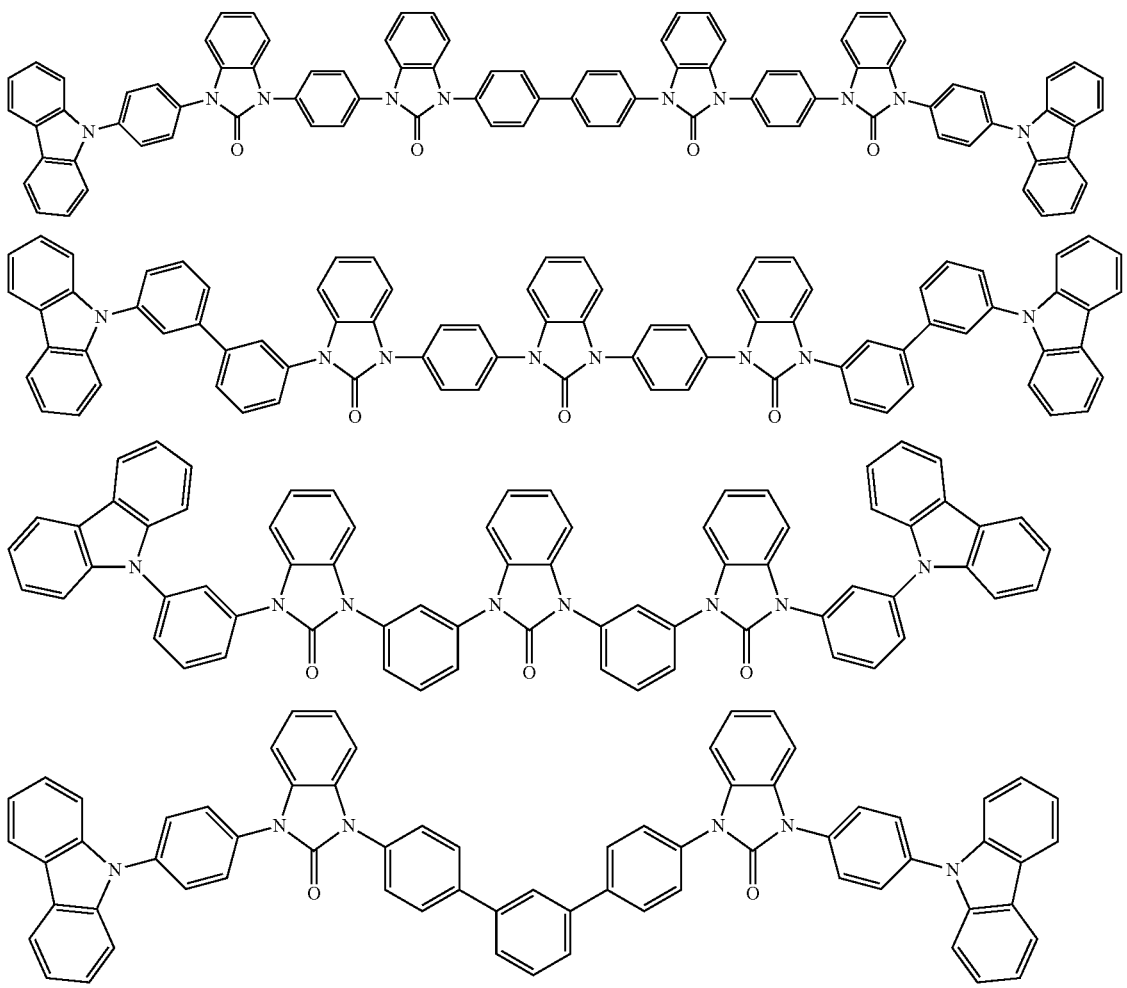

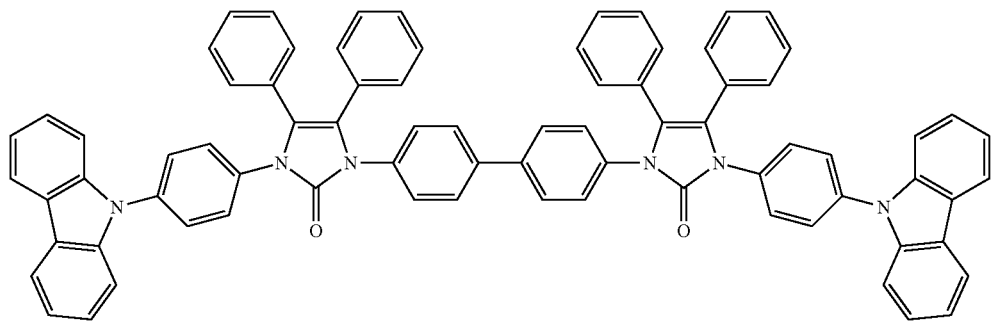
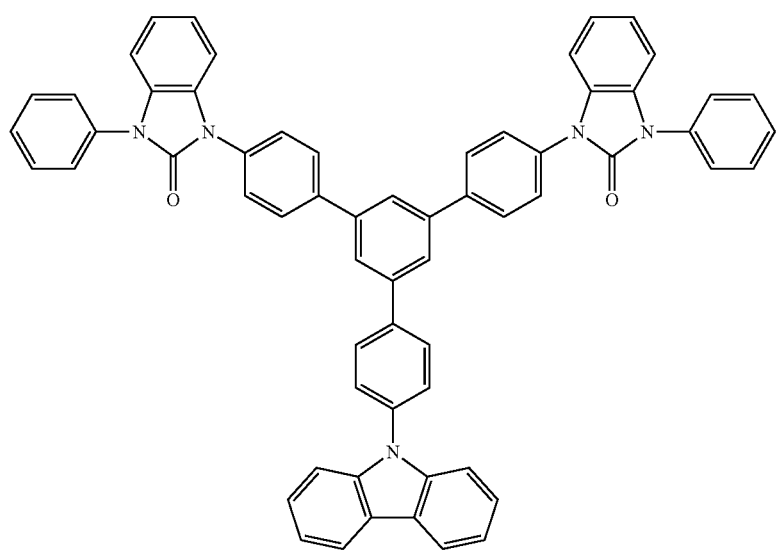
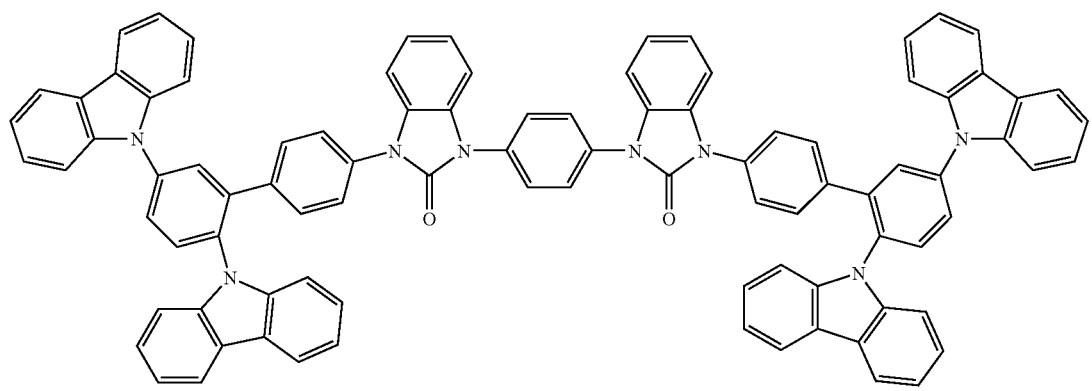
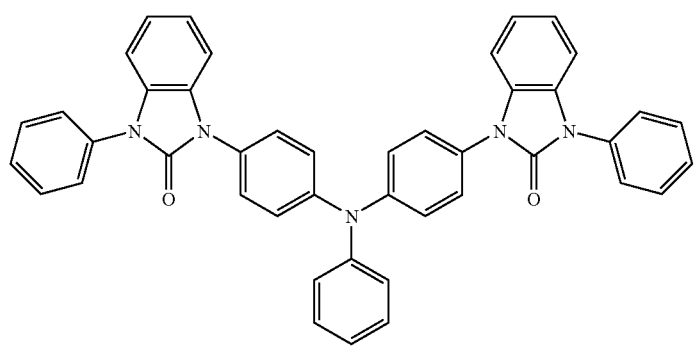

[Chem. 22]
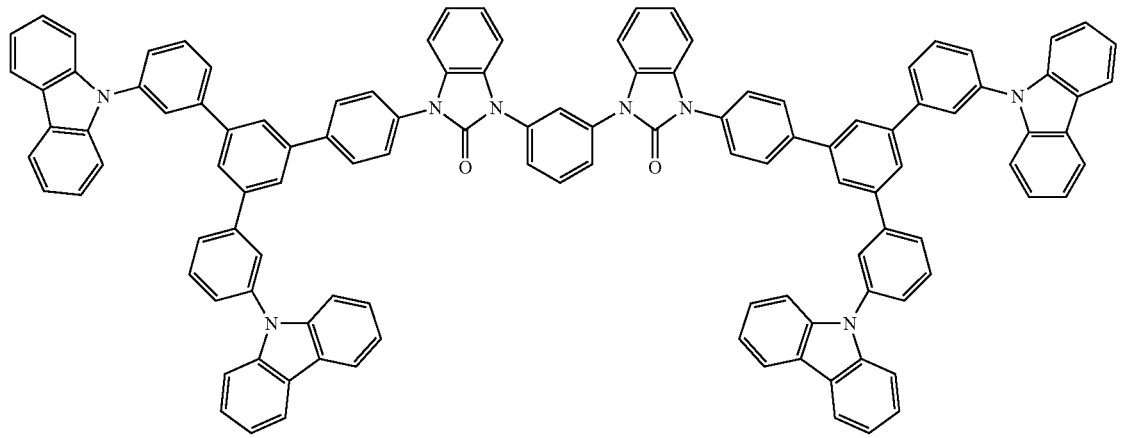
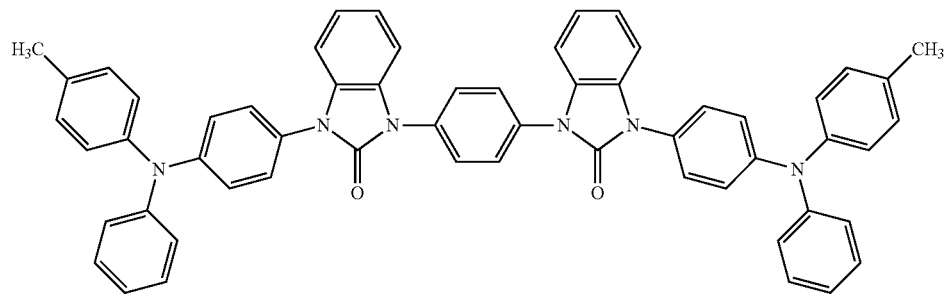
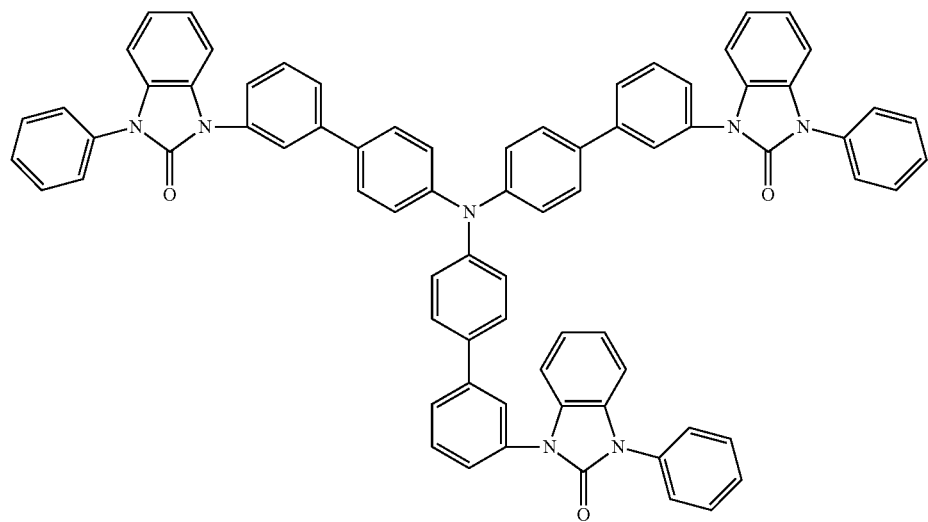

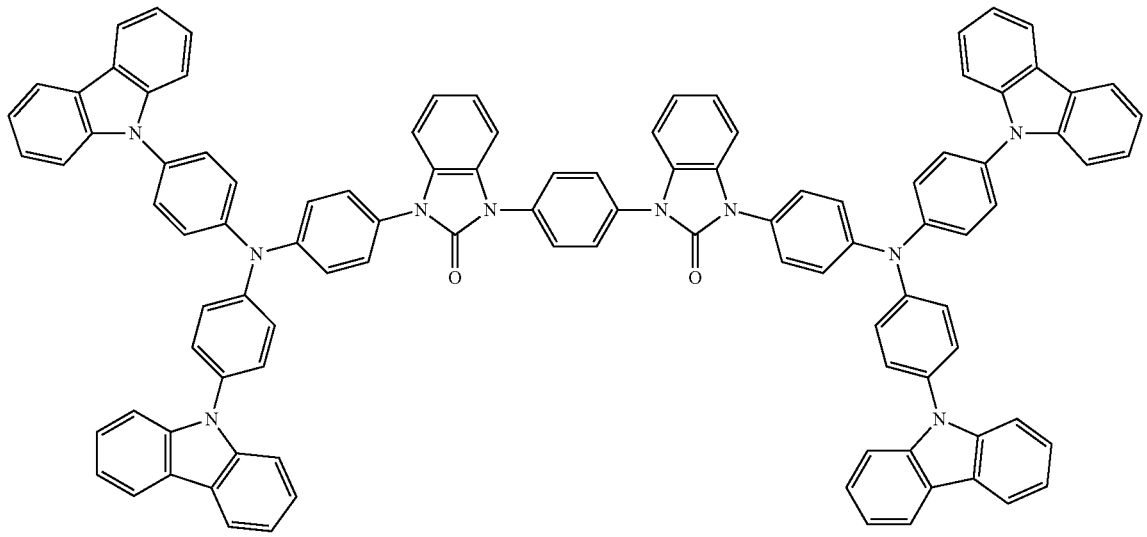
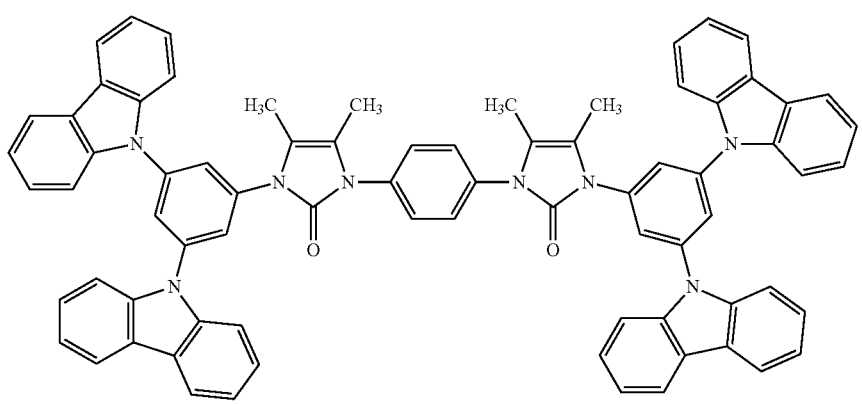
[Chem. 23]
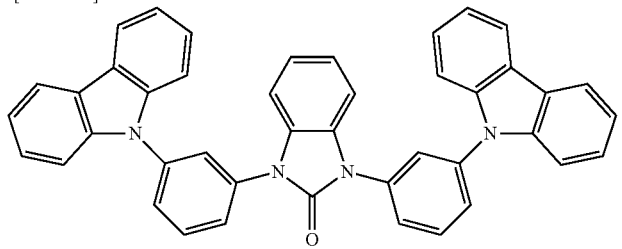
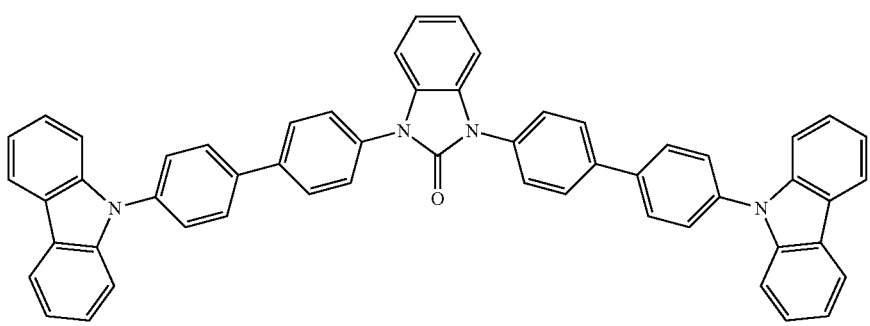

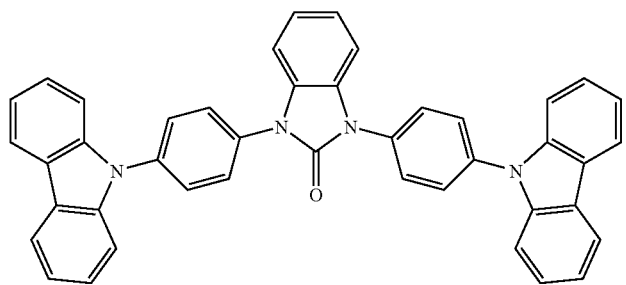
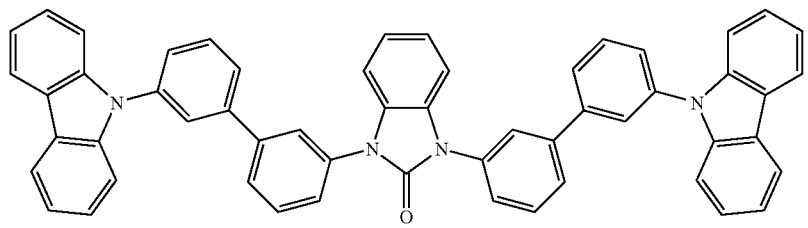
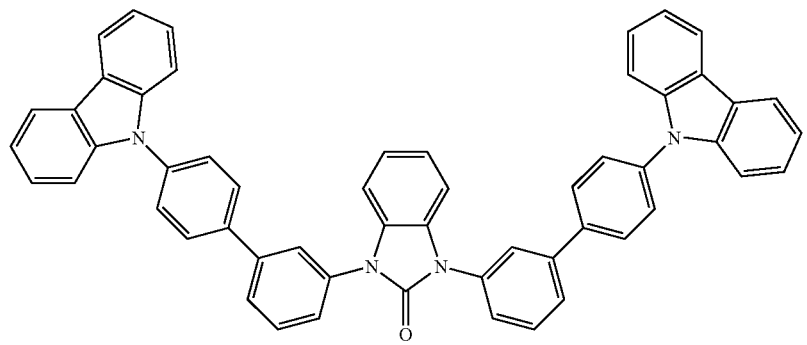
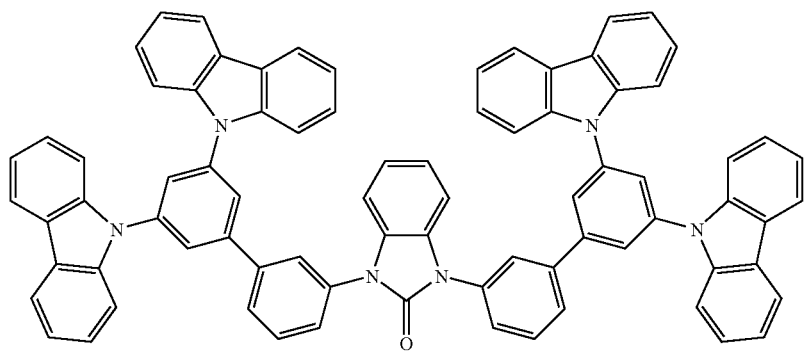
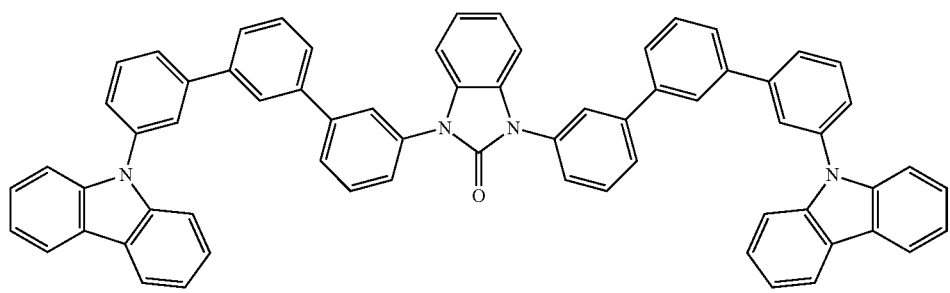

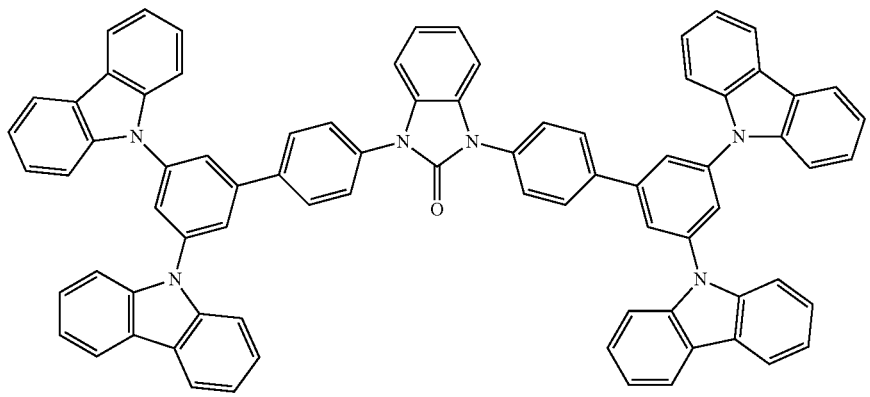
[Chem. 24]
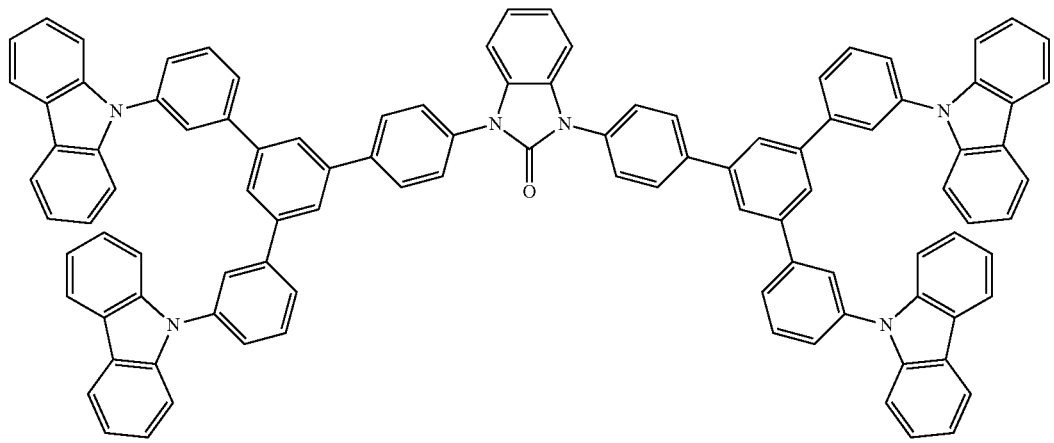
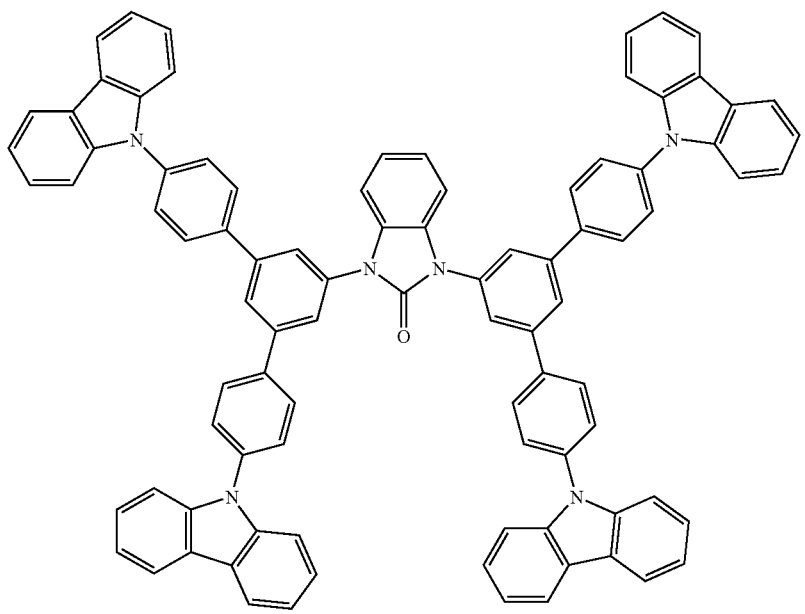

-continued
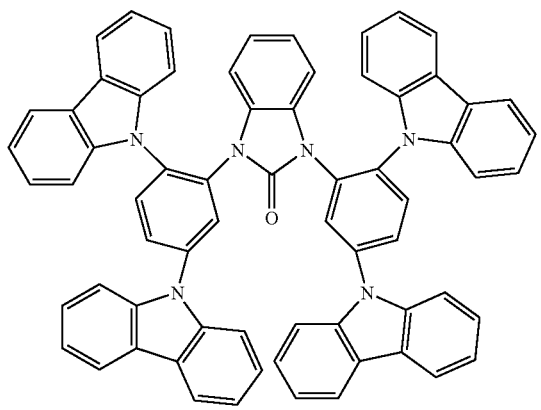
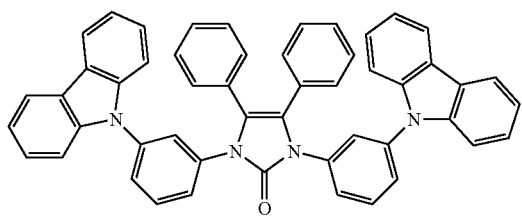
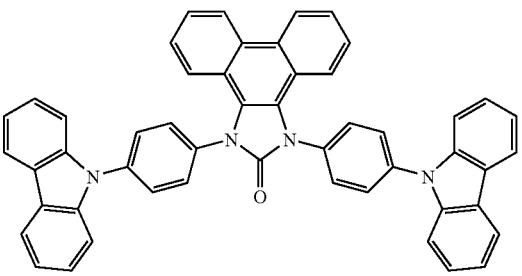
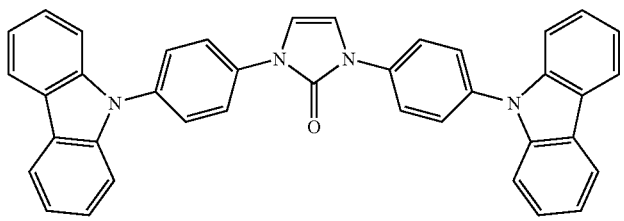
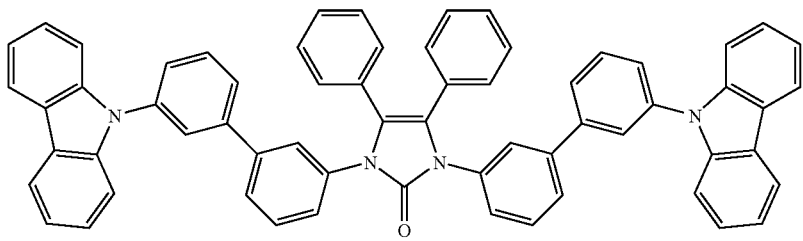
[Chem. 25]
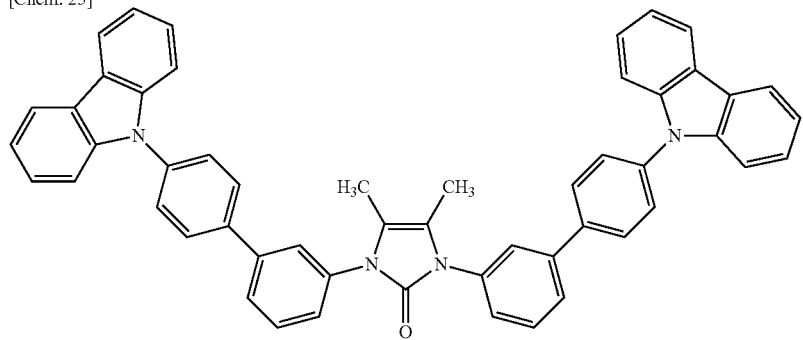

-continued
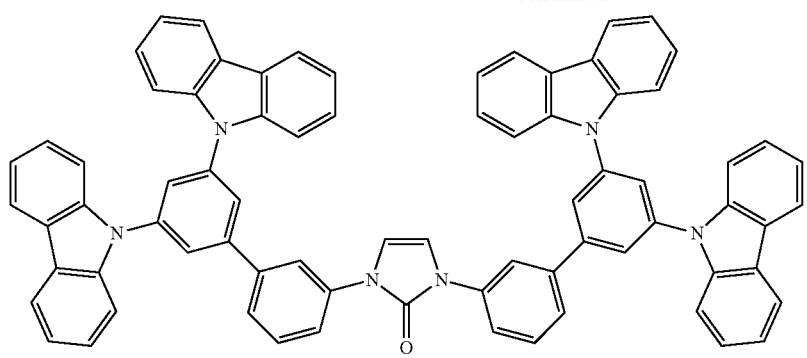
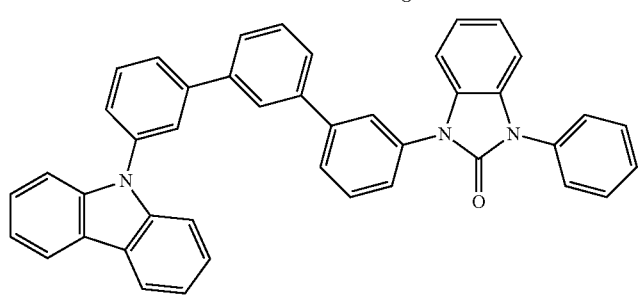
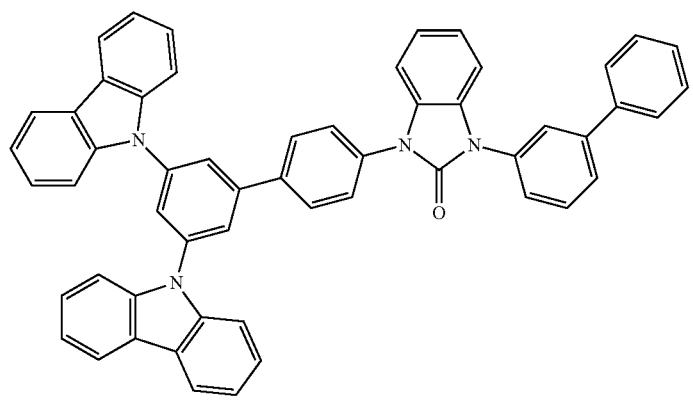
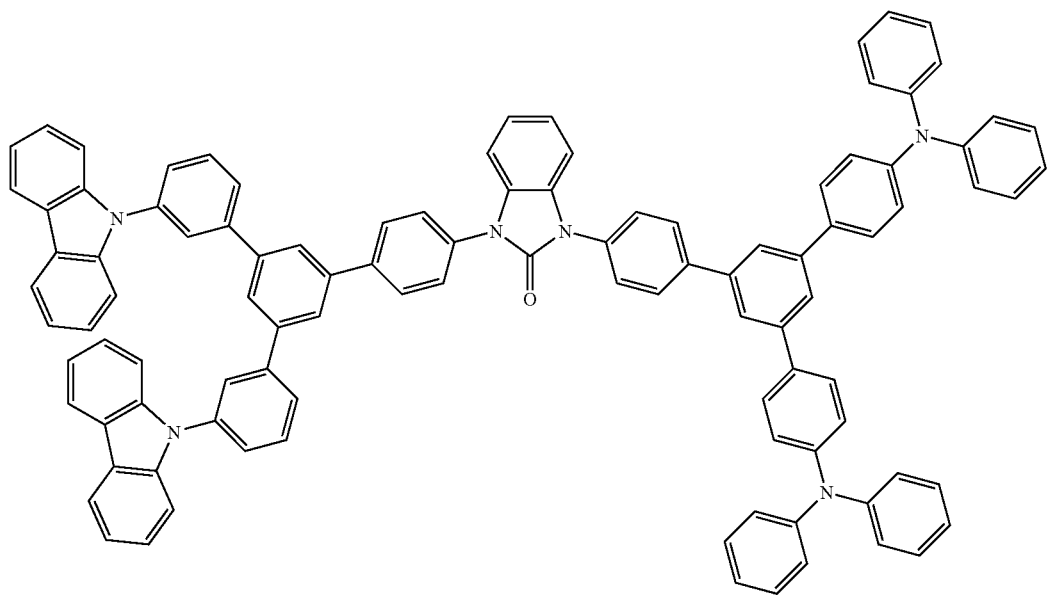

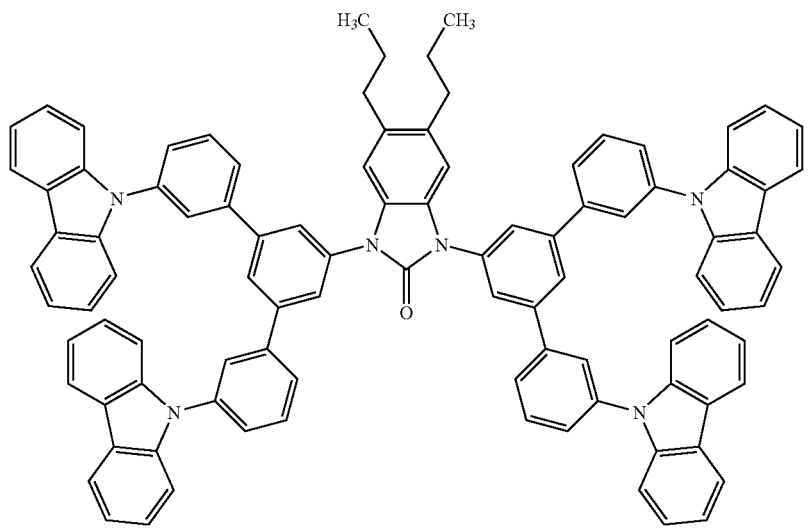
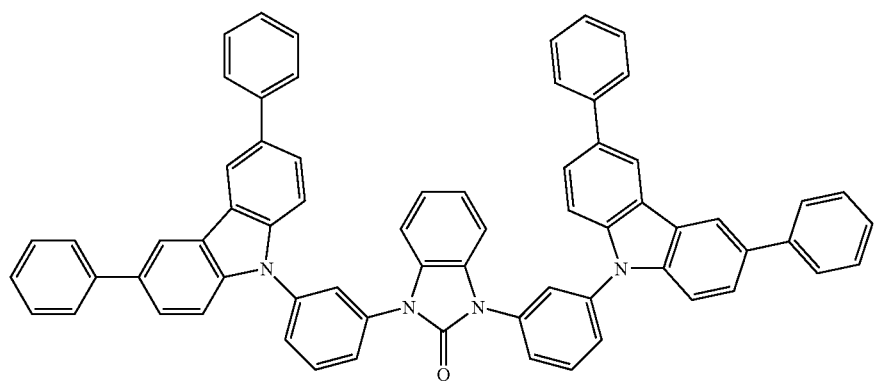
[Chem. 26]
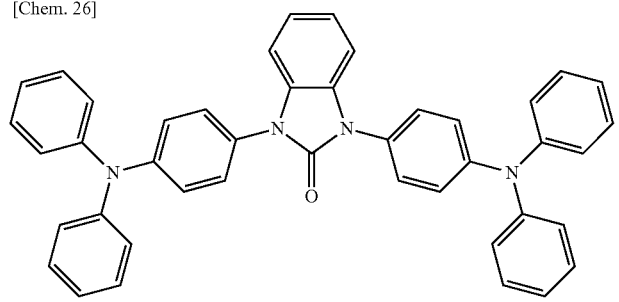
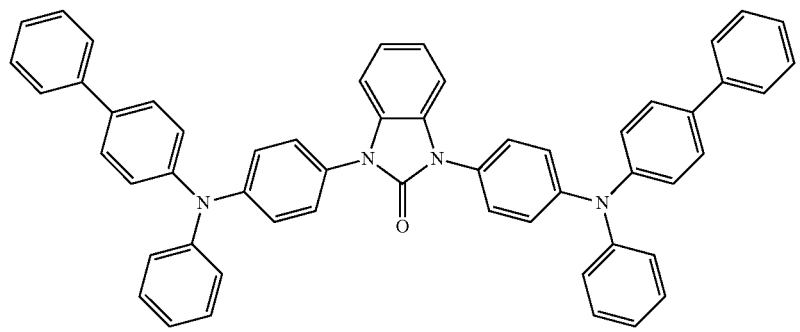

-continued
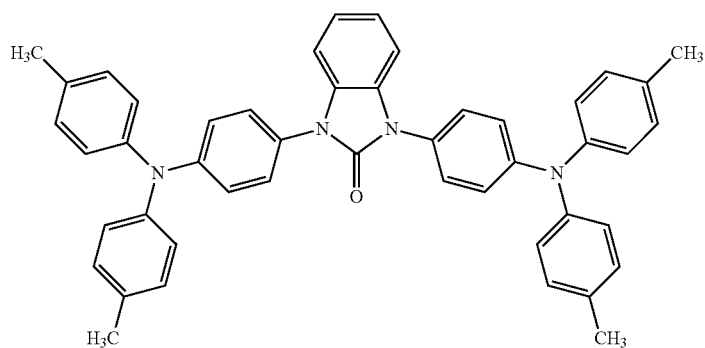
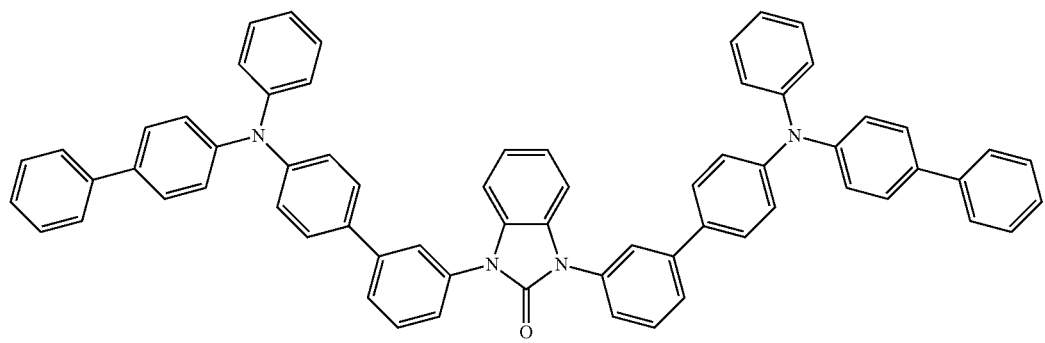
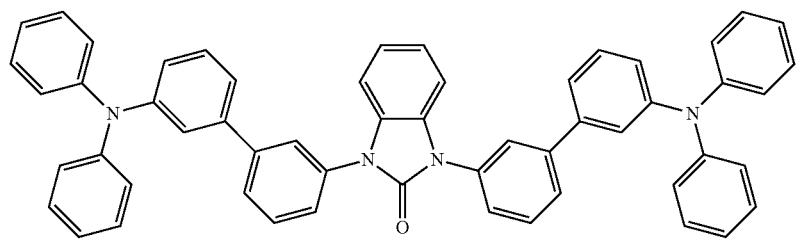
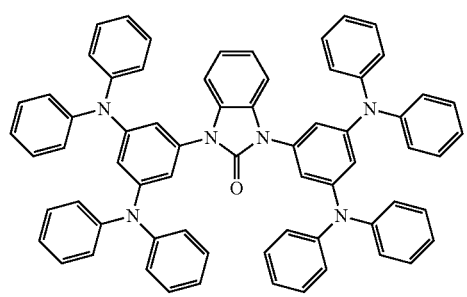
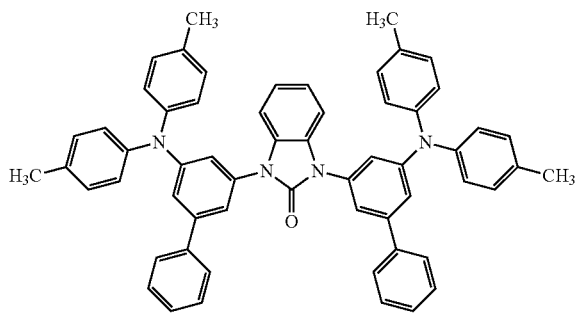

[Chem. 27]
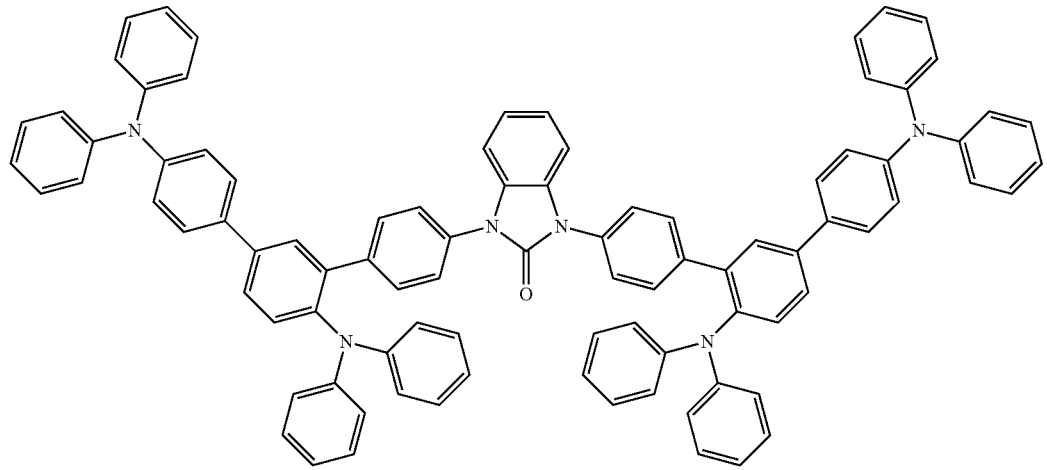
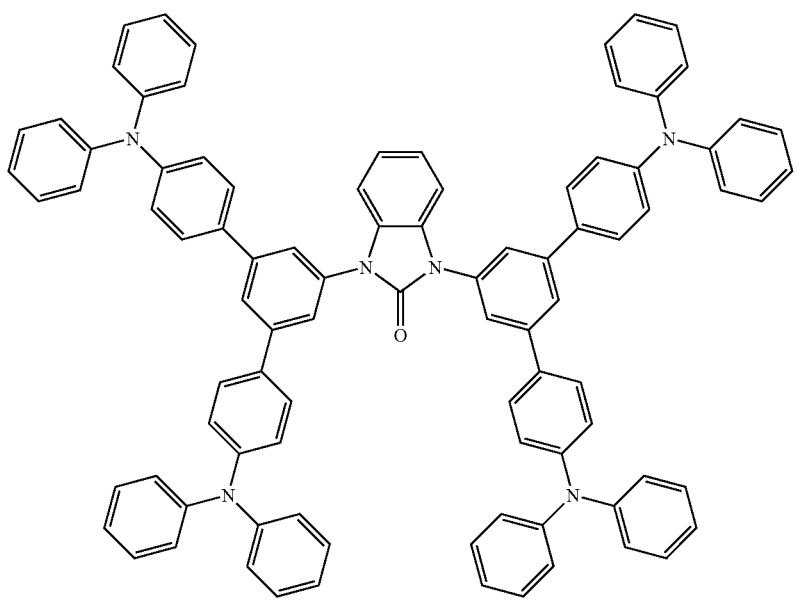
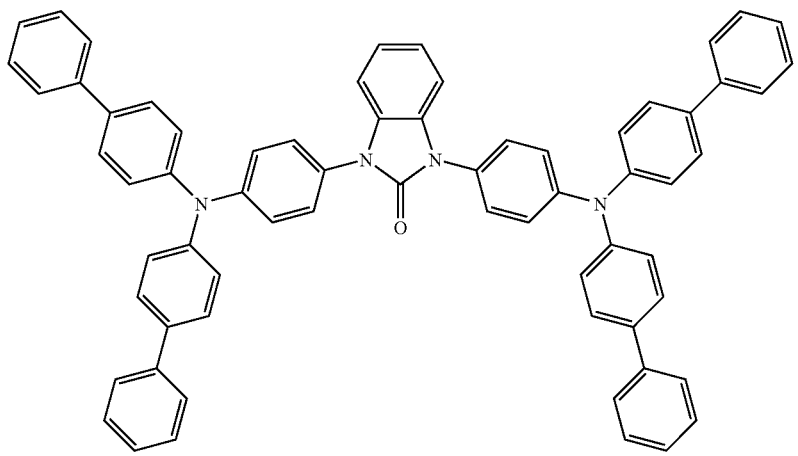

-continued
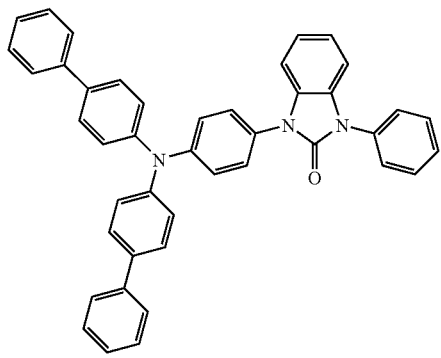
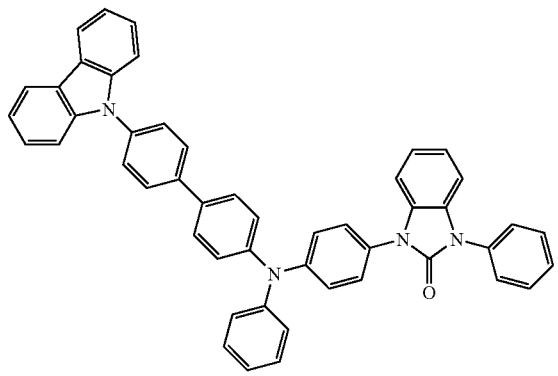
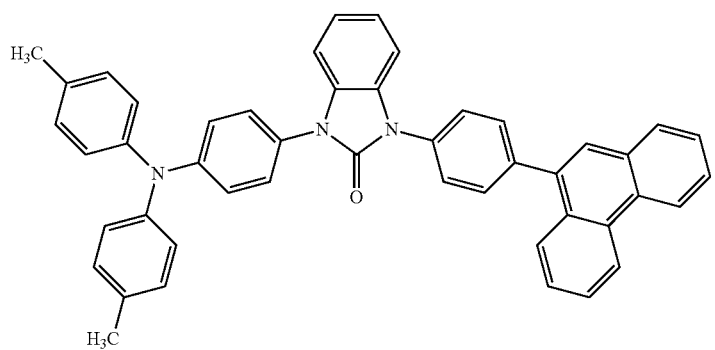
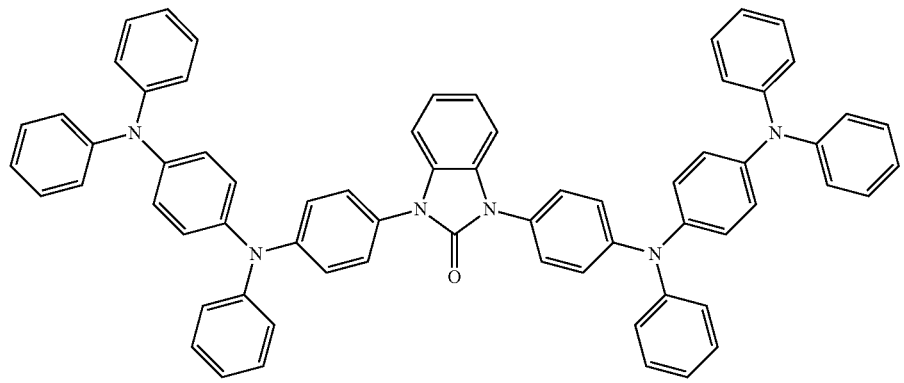
[Chem. 28]
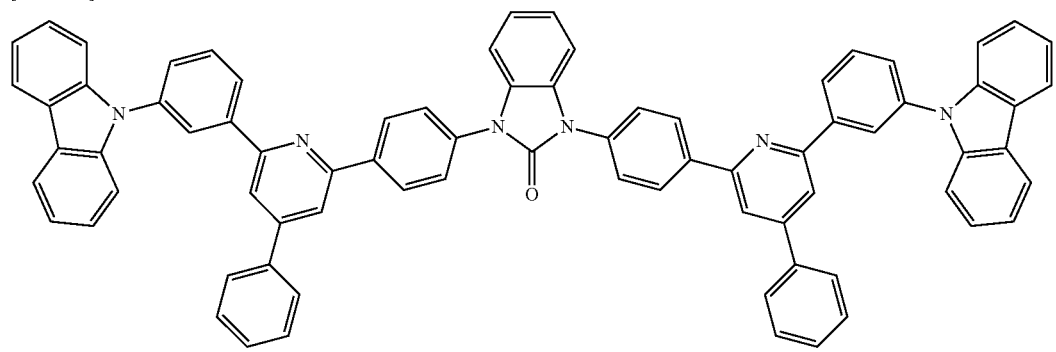

-continued
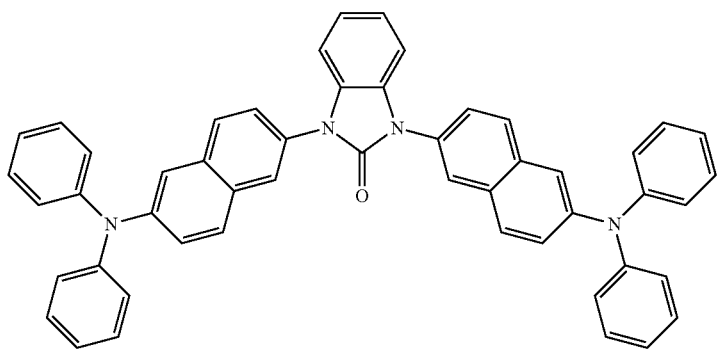
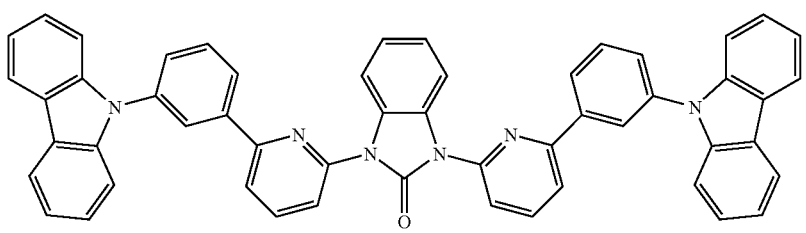
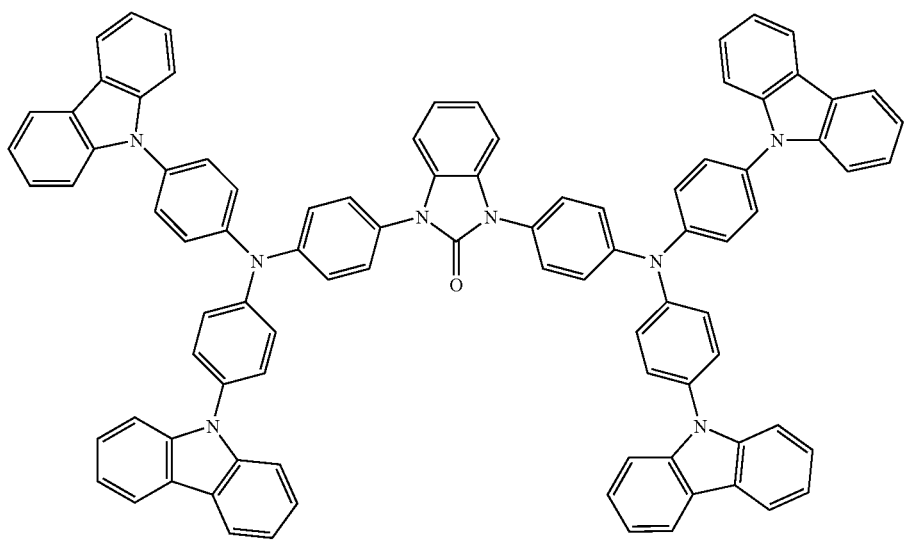
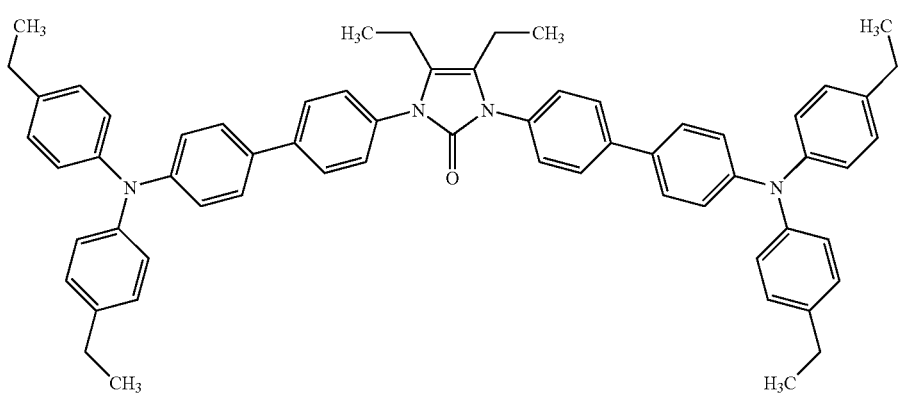

-continued
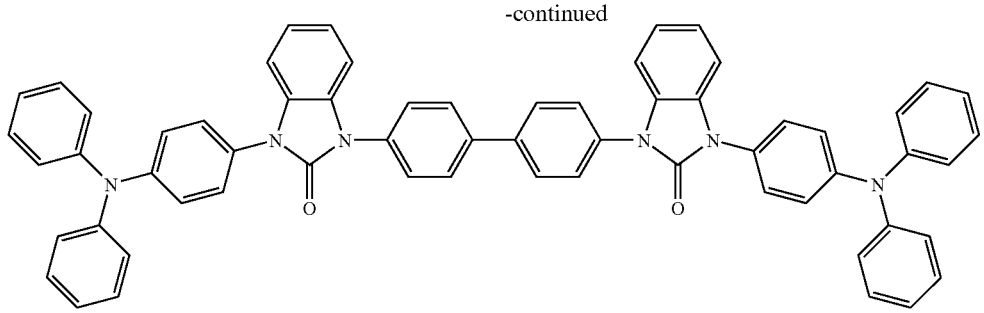
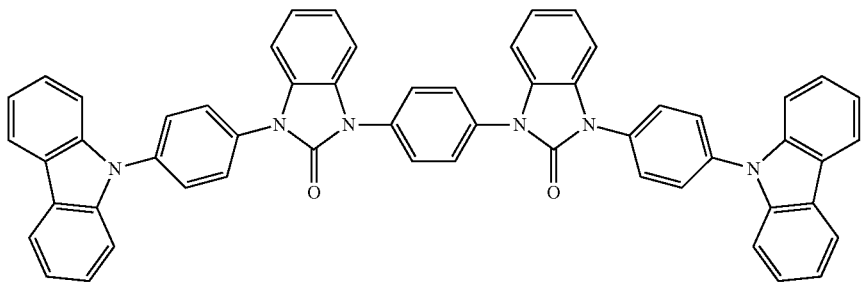
[Chem. 29]
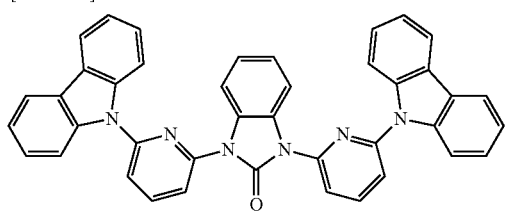
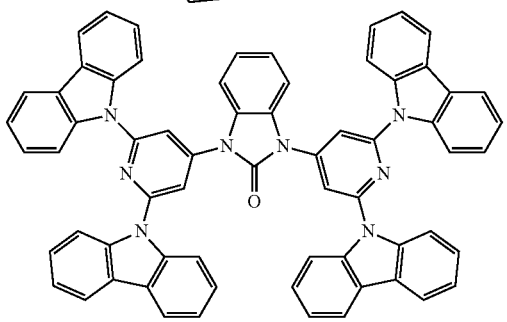
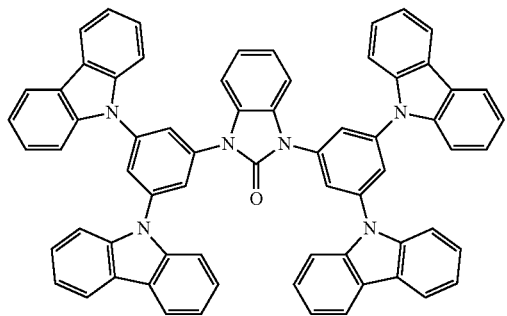
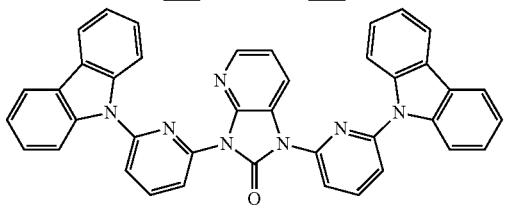
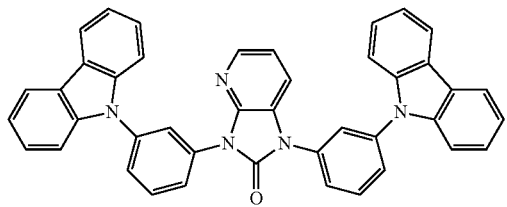
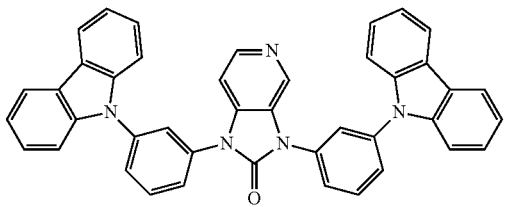
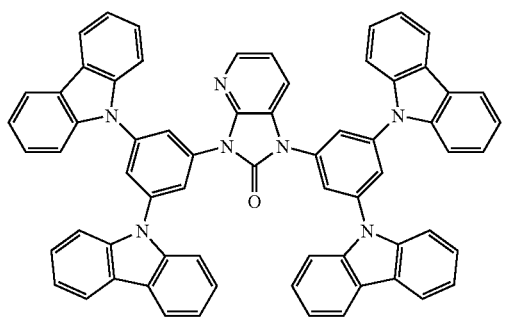
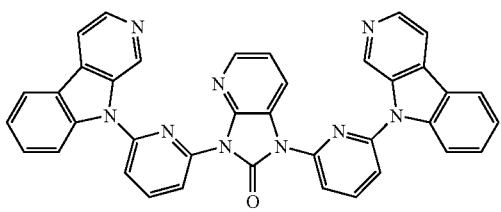

-continued
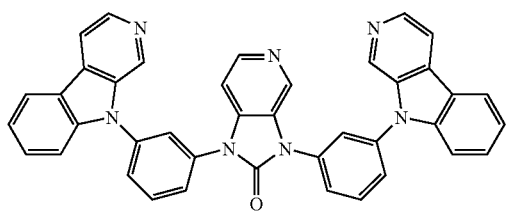
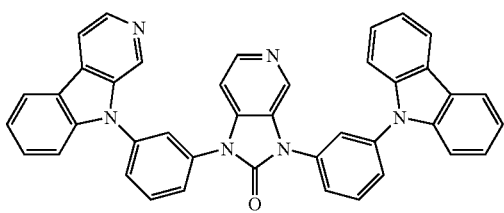
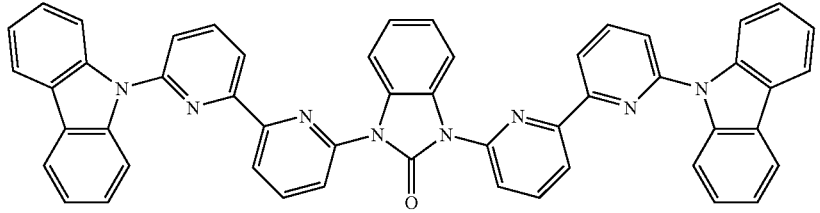
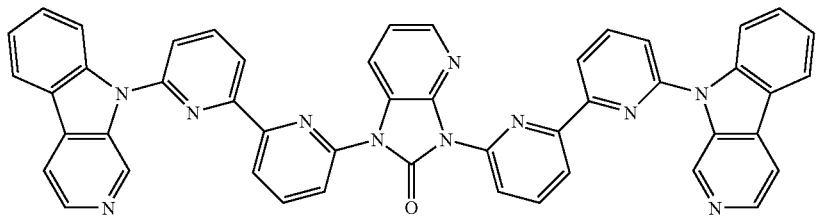
[Chem. 30]
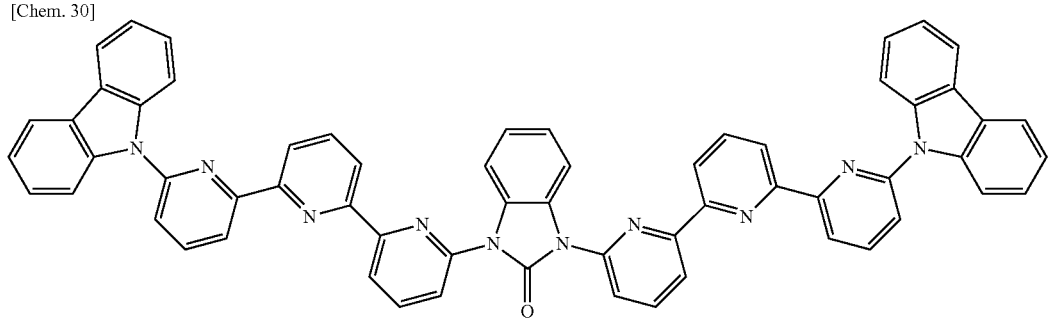
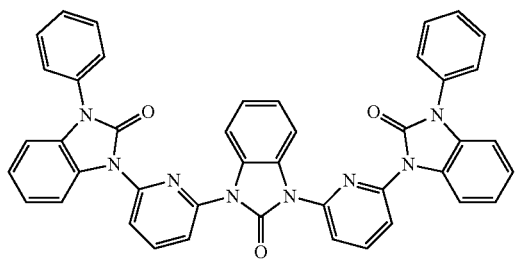
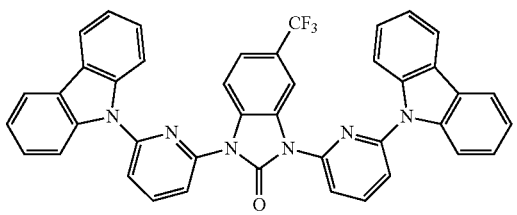
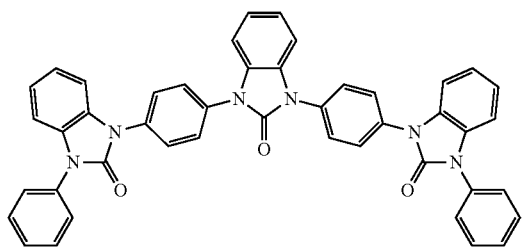
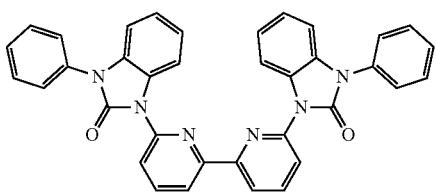
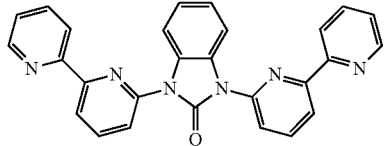
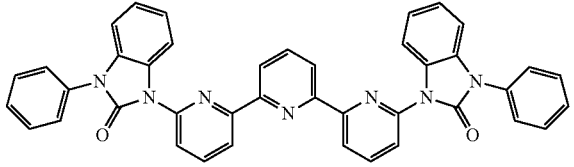

-continued
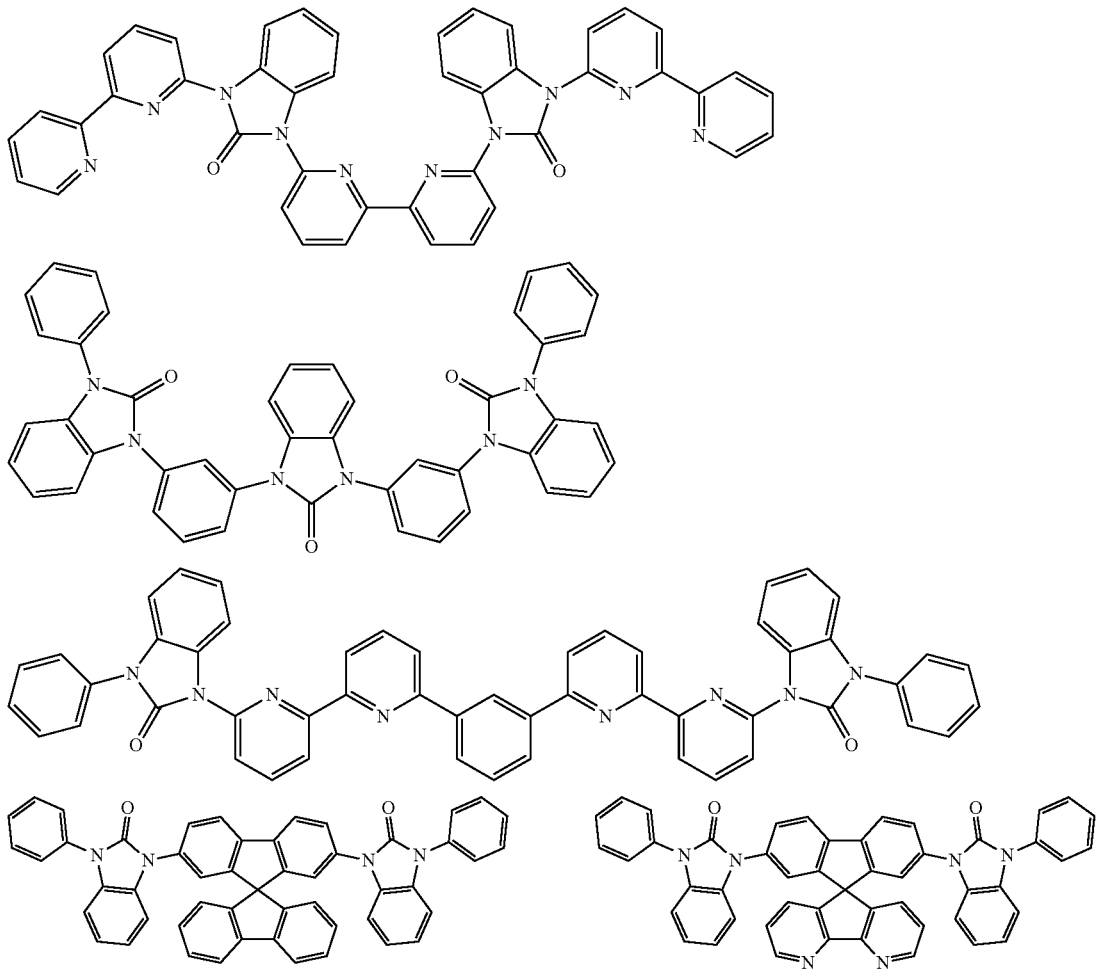
[Chem. 31]
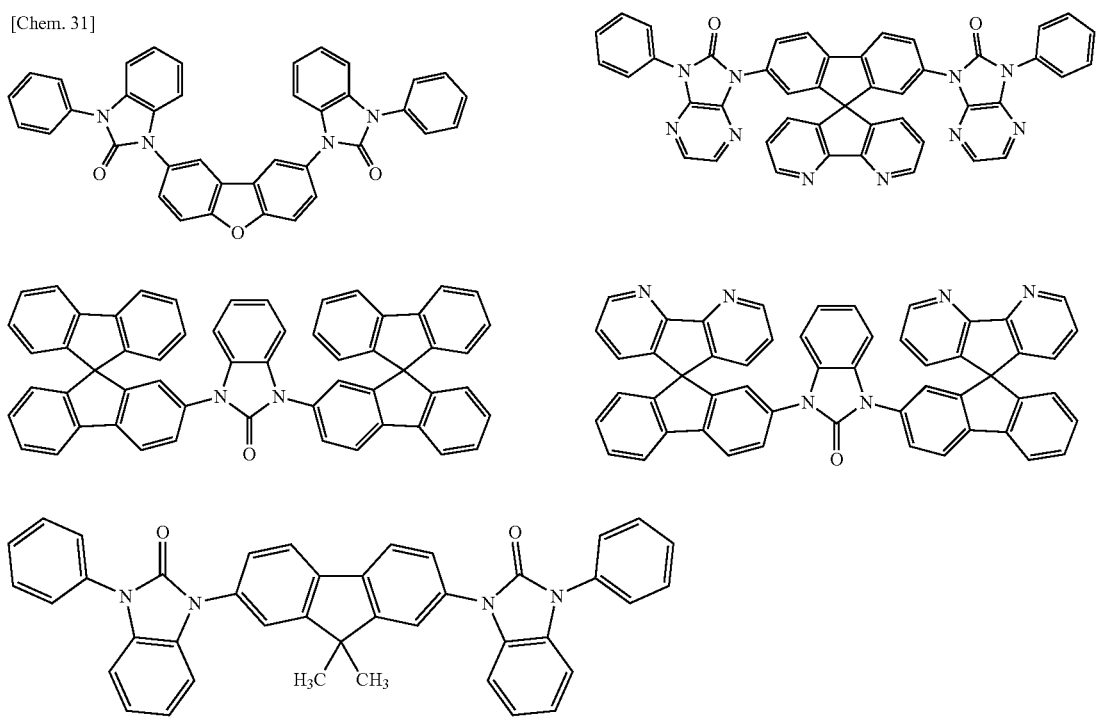

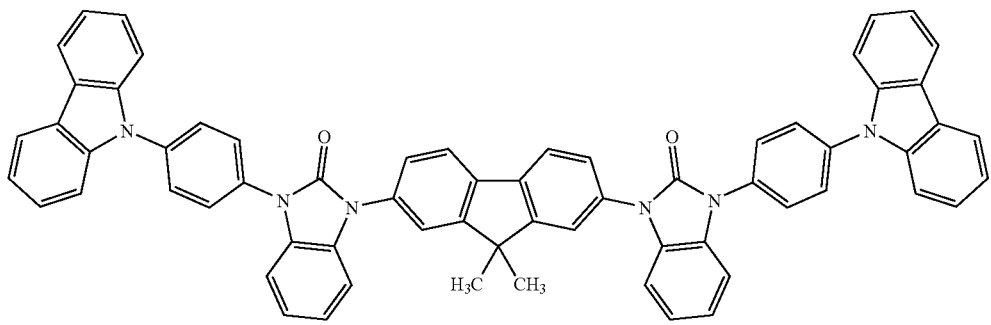
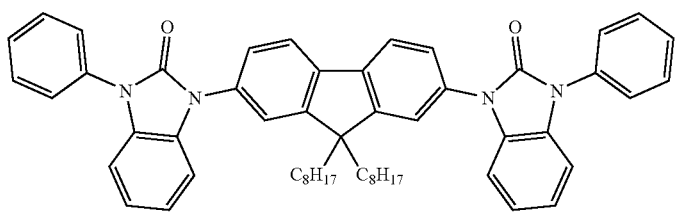
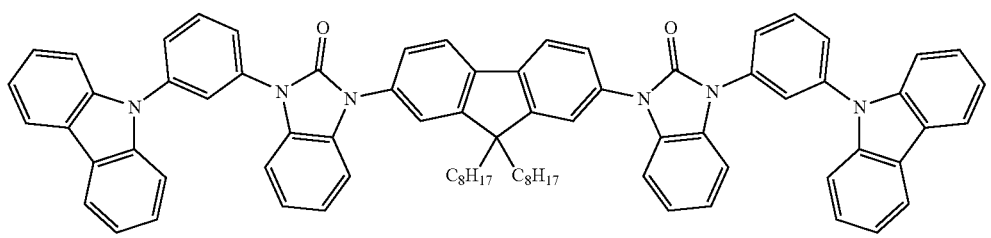
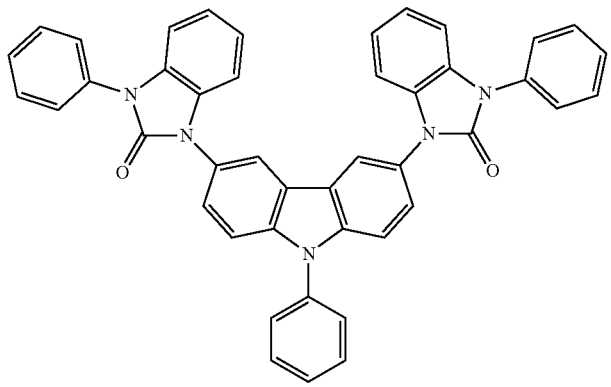
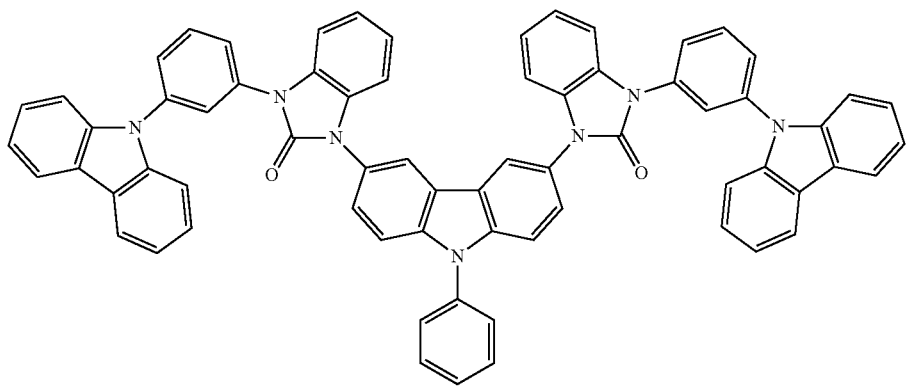

[Chem. 32]

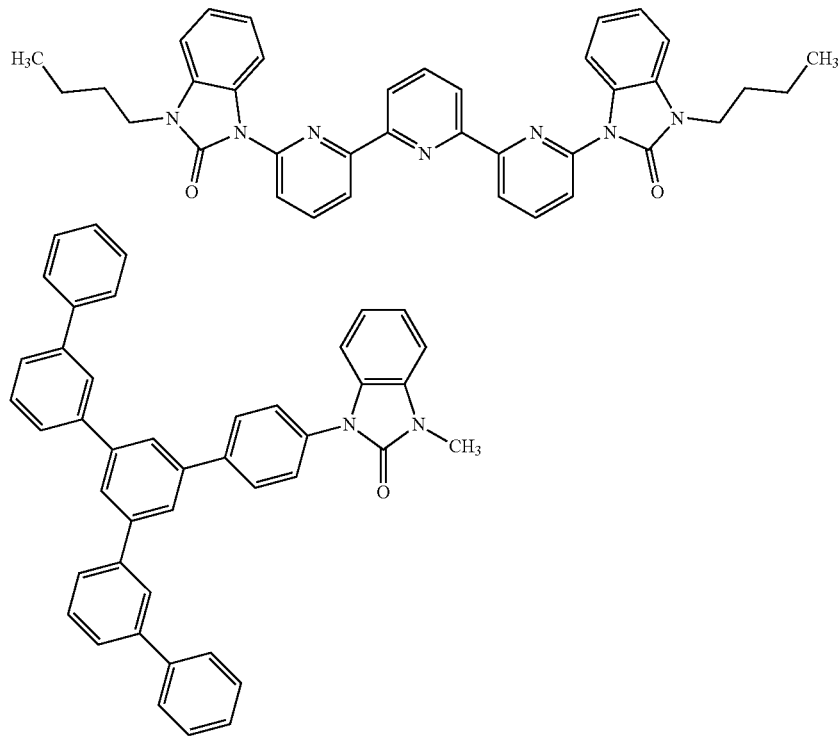

[9] Synthesis Method

The organic compound of the present invention can be synthesized by a known method with materials selected in response to the structure of a target compound.

For example, the compound can be synthesized according to a procedure described below.

A 2-hydroxyimidazole derivative represented by Formula (I) and a halide ($Ar^1$—$X^1$) are stirred at a temperature in the range of 20° C. to 300° C. for 1 to 60 hours without a solvent or in a solvent, such as an aromatic solvent or an ether solvent, under a stream of an inert gas in the presence of a transition metal catalyst (in an amount equivalent to about 0.001 to 5 times the amount of the halogen atoms of the halide ($Ar^1$—$X^1$)), such as a copper powder, copper(I) halide, copper(I) oxide, or a palladium complex, and a basic material (in an amount of about 1 to 10 equivalents with respect to the halogen atoms of the halide ($Ar^1$—$X^1$)), such as potassium carbonate, calcium carbonate, potassium phosphate, cesium carbonate, sodium tert-butoxide, or triethylamine. Thereby, a compound represented by Formula (II) is obtained. The compound represented by Formula (II) and a halide ($X^2$—$Ar^2$-Q) are stirred at a temperature in the range of 20° C. to 300° C. for 1 to 60 hours without a solvent or in a solvent, such as an aromatic solvent or an ether solvent, under a stream of an inert gas in the presence of a transition metal catalyst (in an amount equivalent to about 0.001 to 5 times the amount of the halogen atoms of the halide ($X^2$—$Ar^2$-Q)), such as a copper powder, copper(I) halide, copper(I) oxide, or a palladium complex, and a basic material (in an amount equivalent to about 1 to 10 times the amount of the halogen atoms of the halide ($X^2$—$Ar^2$-Q)), such as potassium carbonate, calcium carbonate, potassium phosphate, cesium carbonate, sodium tert-butoxide, or triethylamine. Thereby, the organic compound of the present invention represented by Formula (I) shown below is obtained. Hereinafter, $Ar^1$ to $Ar^5$, $R^1$, $R^2$, and Q are defined the same as in Formula (I) shown above. $X^1$ and $X^2$ represent halogen atoms.

[Chem. 33]

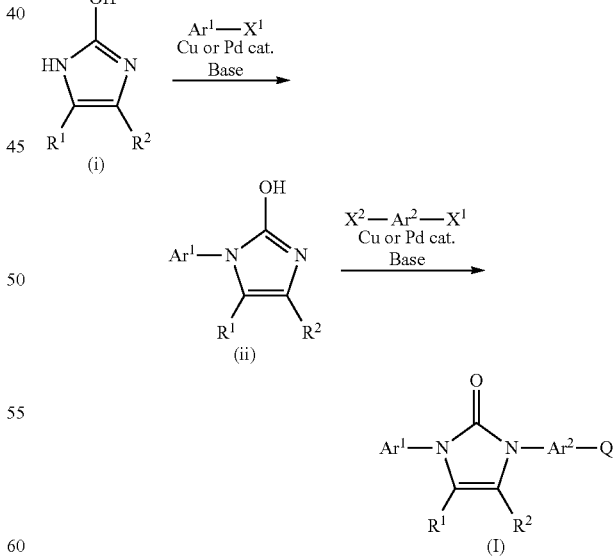

As a method for synthesizing the compound represented by Formula (ii), a method for forming a urea-bond-containing five-membered ring (1,3-dihydroimidazol-2-one) described in Tetrahedron, 1999, 55, pp. 475-484, Tetrahedron Letters, 2000, 41, pp. 6387-6391, Tetrahedron 1990, 46, pp. 1331-

1342, European Journal of Organic Chemistry, 1998, pp. 183-187, and The Journal of Organic Chemistry, 2004, 69, pp. 7752-7754 may also be employed.

When Q=Ar$^5$, a halide (X$^2$—Ar$^2$—Ar$^5$) can be synthesized through a known coupling reaction. With respect to the known coupling technique, a binding (coupling) reaction between rings, e.g., a coupling reaction between an aryl halide and an aryl borate, described or cited in "Palladium in Heterocyclic Chemistry: A Guide for the Synthetic Chemist" (second edition, 2002, Jie Jack Li and Gordon W. Gribble, Pergamon), "Senikinzoku ga Hiraku Yukigosei, Sono Tasaina Hannoukeishiki to Saishin no Seika (Organic Synthesis Pioneered with Transition Metal, various reactions and latest achievements)" (1997, Jiro TSUJI, Kagaku-Dojin Publishing Co., Inc.), "Vollhardt & Schore Gendai Yukikagaku, Ge (Vollhardt & Schore, Modern Organic Chemistry II)" (2004, K. P. C. Vollhardt, Kagaku-Dojin Publishing Co., Inc.), and the like, may be employed.

When Q=NAr$^3$Ar$^4$, a halide (X$^2$—Ar$^2$—NAr$^3$Ar$^4$) can be synthesized from a secondary amine compound (Ar$^3$Ar$^4$NH) and a dihalide (X$^2$—Ar$^2$—X$^3$ (X$^2$, X$^3$=F, Cl, Br, or I)) as shown in a formula shown below. Usable reagents and the like are the same as in the step of synthesizing the compound represented by Formula (ii) from the compound represented by Formula (i).

[Chem. 34]

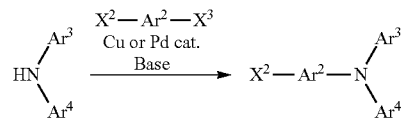

With respect to a method for purifying a compound synthesized, known techniques, for example, known methods described in, e.g., "Bunri Seisei Gijutsu Handobukku (Handbook of Separation and Purification)" (1993, The Chemical Society of Japan), "Kagaku Henkanhou niyoru Biryouseibun oyobi Nanseiseibussitsu no Koudobunri (Sophisticated Separation of Trace Component and Hard-to-Purify Substances by Chemical Conversion Process)" (1988, Industrial Publishing & Consulting, Inc.), and Section "Bunri to Seisei (Separation and Purification)" in "Jikken Kagaku Koza (Dai 4 han) 1 (Courses in Experimental Chemistry, 4th Ed.)", (1990, The Chemical Society of Japan), may be employed.

Specific Examples thereof include extraction (including suspension washing, boil washing, ultrasonic cleaning, and acid and base washing), adsorption, occlusion, melting, crystallization (including recrystallization and reprecipitation from a solvent), distillation (atmospheric distillation and reduced-pressure distillation), evaporation, sublimation (atmospheric sublimation and reduced-pressure sublimation), ion exchange, dialysis, filtration, ultrafiltration, reverse osmosis, pressure osmosis, zone melting, electrophoresis, centrifugal separation, floatation, sedimentation, magnetic separation, and various chromatographic methods (shape classification: column, paper, thin layer, and capillary; mobile-phase classification: gas, liquid, micelle, and supercritical fluid; separation mechanism: adhesion, partition, ion exchange, molecular sieve, chelate, gel filtration, exclusion, and affinity).

As analytical methods for determining a product and the purity, a gas chromatograph (GC), a high-performance liquid chromatograph (HPLC), a high-speed amino acid analyzer (AAA), a capillary electrophoresis (CE), a size exclusion chromatograph (SEC), a gel permeation chromatograph (GPC), a cross fractionation chromatograph (CFC) mass spectrography (MS, LC/MS, GC/MS, or MS/MS), a nuclear magnetic resonance apparatus (NMR ($^1$HNMR or $^{13}$CNMR)), a Fourier transform infrared spectrophotometer (FT-IR), an ultraviolet, visible, near-infrared spectrometer (UV, VIS, NIR), an electron spin resonance spectrometer (ESR), a transmission electron microscope (TEM-EDX), an electron probe microanalyzer (EPMA), a metal element analysis (an ion chromatograph, an inductively-coupled plasma spectrometer (ICP-AES), an atomic absorption spectrometry (AAS), or an X-ray fluorescent analyzer (XRF)), a non-metallic element analysis, a trace analysis (ICP-MS, GF-AAS, or GD-MS), and the like may be applied, as needed.

[10] Application of Organic Compound

The organic compound of the present invention has high charge transportability and thus can be suitably used as a charge-transporting material for electrophotographic photoreceptors, organic electroluminescent devices, photoelectric transducers, organic solar cells, organic rectifiers, and the like.

The organic compound also has a high triplet excited level. Thus, the use of an inventive charge-transporting material composed of the organic compound of the present invention results in an organic electroluminescent device having excellent heat resistance and capable of operating (luminescing) stably over long periods of time. Therefore, the organic compound and charge-transporting material of the present invention are particularly preferred as materials for organic electroluminescent devices.

[Charge-Transporting Material]

The charge-transporting material of the present invention is composed of the organic compound of the present invention or is represented by Formula (II-2). The charge-transporting material is soluble in toluene in an amount of preferably 2.0 percent by weight or more and more preferably 5.0 percent by weight or more.

[Chem. 35]

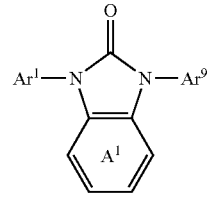

(II-2)

Ring A$^1$ represents an optionally-substituted benzene ring or an optionally-substituted nitrogen-containing aromatic six-membered ring.

Ar$^1$ and Ar$^9$ each independently represent an optionally-substituted aromatic hydrocarbon group or an optionally-substituted aromatic heterocyclic group.

In Formula (II-2), ring A$^1$ and Ar$^1$ are defined the same as ring A$^1$ and Ar$^1$ in Formula (II). The same is true in examples of substituents and preferred substituents that may be provided on them. Examples of Ar$^9$ include the same examples of Ar$^1$. Substituents that may be provided on Ar$^9$ are the same as the substituents that may be provided on Ar$^1$.

The molecular weight of the charge-transporting material of the present invention represented by Formula (II-2) is usually 5,000 or less, preferably 3,000 or less, and more preferably 2,000 or less, and usually 300 or more, preferably 500 or more, and more preferably 600 or more.

A molecular weight exceeding the upper limit described above may result in difficulty in purification due to an increase in the molecular weight of impurities. A molecular weight of less than the lower limit described above may significantly reduce heat resistance due to reductions in glass transition temperature, melting point, vaporization temperature, and the like.

The charge-transporting material of the present invention usually has a glass transition temperature of 40° C. or higher. From the viewpoint of achieving good heat resistance, the glass transition temperature is preferably 80° C. or higher and more preferably 110° C. or higher.

The charge-transporting material of the present invention usually has a vaporization temperature of 300° C. to 800° C.

The energy difference between the excited triplet state and the ground state of the charge-transporting material of the present invention is usually 2.0 eV to 4.0 eV. From the viewpoint of increasing the efficiency of an organic electroluminescent device utilizing phosphorescent emission, the energy difference between the excited triplet state and the ground state is preferably 2.3 eV or more, more preferably 2.6 eV or more, and still more preferably 2.9 eV or more.

As described below, an aromatic hydrocarbon is preferred as a solvent contained in a composition for charge-transporting material. Toluene is a typical aromatic hydrocarbon and is used as an index of the solubility of the organic compound (charge-transporting material) in the present invention.

The charge-transporting material of the present invention has a solubility of 2.0 percent by weight or more in toluene. Thus, a layer constituting an organic electroluminescent device can be easily formed by a wet film-forming method, which is preferred. The upper limit of the solubility is not particularly limited but is usually about 50 percent by weight.

[Composition for Charge-Transporting Material]

A composition for charge-transporting material of the present invention contains the charge-transporting material of the present invention. The composition for charge-transporting material usually contains the charge-transporting material of the present invention and a solvent. More preferably, the composition for charge-transporting material contains a phosphorescent emitting material. Preferably, the composition for charge-transporting material is used for an organic electroluminescent device.

[1] Solvent

A solvent contained in the composition for charge-transporting material of the present invention is not particularly limited as long as the charge-transporting material, which is a solute, and the like are satisfactorily soluble in the solvent.

Various solvents may be used because the composition for charge-transporting material of the present invention has a high solubility. Usable examples thereof include aromatic hydrocarbons, such as toluene, xylene, mesitylene, cyclohexylbenzene, and tetralin; halogenated aromatic hydrocarbons, such as chlorobenzene, dichlorobenzene, and trichlorobenzene; aromatic ethers, such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole; aromatic esters, such as phenyl acetate, phenyl propionate, methyl benzoate, ethyl benzoate, propyl benzoate, and n-butyl benzoate; alicyclic ketones, such as cyclohexanone and cyclooctanone; aliphatic ketones, such as methyl ethyl ketone and dibutylketo ketone; alicyclic alcohols, such as methyl ethyl ketone, cyclohexanol, and cyclooctanol; aliphatic alcohols, such as butanol and hexanol; aliphatic ethers, such as ethylene glycol dimethyl ether, ethylene glycol diethyl ether, and propylene glycol-1-monomethyl ether acetate (PGMEA); and aliphatic esters, such as ethyl acetate, n-butyl acetate, ethyl lactate, and n-butyl lactate. Among these, aromatic hydrocarbons, such as toluene, xylene, mesitylene, cyclohexylbenzene, and tetralin are preferred because water has a low solubility therein and aromatic hydrocarbons do not readily deteriorate.

In an organic electroluminescent device, many materials that deteriorate significantly by water, e.g., a cathode, are used. Thus, the presence of water in the composition may cause a film after drying to contain water to degrade the properties of the device, which is not preferred.

Examples of a method for reducing the amount of water in the composition include the use of a nitrogen gas seal and a desiccant; dehydration of a solvent in advance; and the use of a solvent in which water has a low solubility. Among these, the use of a solvent in which water has a low solubility is preferred because a phenomenon in which a solution film absorbs water and becomes whitened can be prevented during a wet film-forming process. From such a point of view, preferably, the composition for charge-transporting material according to this embodiment contains 10 percent by weight or more of a solvent in which, for example, water has a solubility of 1 percent by weight or less and preferably 0.1 percent by weight or less at 25° C.

To inhibit a reduction in the stability of the film formation due to solvent evaporation from the composition during wet film formation, a solvent having a boiling point of 100° C. or higher, preferably 150° C. or higher, and more preferably 200° C. or higher is effectively used for the composition for charge-transporting material. To obtain a more uniform film, it is necessary to evaporate the solvent from a solution film immediately after the film formation at an appropriate rate. To achieve this, it is effective to use a solvent usually having a boiling point of 80° C. or higher, preferably 100° C. or higher, and more preferably 120° C. or higher, and usually less than 270° C., preferably less than 250° C., and more preferably less than 230° C.

A solvent that satisfies the above-described requirements, i.e., the solubility of a solute, an evaporation rate, and the solubility of water, may be used alone. Alternatively, a mixture of two or more solvents may be used.

[2] Luminescent Material

The composition for charge-transporting material of the present invention, in particular, the composition for charge-transporting material used as the composition for charge-transporting material preferably contains a luminescent material.

The luminescent material refers mainly to a luminescent component in the composition for charge-transporting material of the present invention and corresponds to a dopant component in an organic electroluminescent device. In the case where usually 10% to 100%, preferably 20% to 100%, more preferably 50% to 100%, and most preferably 80% to 100% of the quantity of light (unit: $cd/m^2$) emitted from the composition for charge-transporting material is attributed to a component, the component is defined as the luminescent material.

Any known luminescent material may be used as the luminescent material. Fluorescent emitting materials or phosphorescent emitting materials may be used alone or as a mixture of two or more. From the viewpoint of achieving good internal quantum efficiency, phosphorescent emitting materials are preferred.

In the case where the luminescent material is used for the composition for charge-transporting material of the present invention, the wavelength of the maximum emission peak of the luminescent material is preferably in the range of 390 to 490 nm.

For the purpose of improving the solubility in a solvent, it is also important to reduce the symmetry and stiffness of the molecule of the luminescent material or to introduce a lipophilic substituent such as an alkyl group.

Examples of a blue-emitting fluorescent dye that emits blue light include perylene, pyrene, anthracene, coumarin, p-bis(2-phenylethenyl)benzene, and derivatives thereof. Examples of a green-emitting fluorescent dye include quinacridone derivatives and coumarin derivatives. Examples of a yellow-emitting fluorescent dye include rubrene and perimidone derivatives. Examples of red-emitting fluorescent dye include DCM compounds, benzopyran derivatives, rhodamine derivative, benzothioxanthene derivatives, and azabenzothioxanthene.

Examples of the phosphorescent emitting material include organometallic complexes containing metals selected from groups 7 to 11 of the periodic table.

Preferred examples of the metals of the phosphorescent organometallic complexes containing the metals selected from groups 7 to 11 of the periodic table include ruthenium, rhodium, palladium, silver, rhenium, osmium, iridium, platinum, and gold. These organometallic complexes include a compound represented by General Formula (V) or Formula (VI) shown below.

  (V)

In General Formula (V), M represents a metal. q represents the valence of the metal. L and L' represent bidentate ligands. j represents 0, 1, or 2.

[Chem. 36]

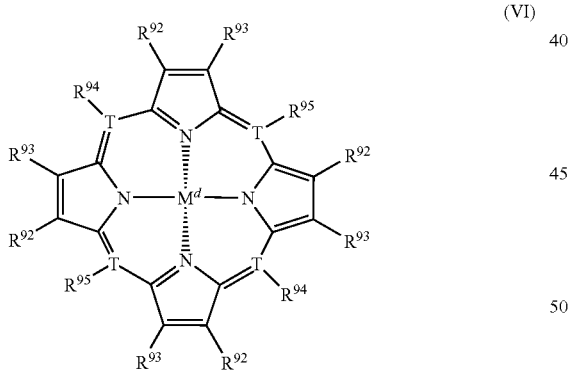  (VI)

In General Formula (VI), $M^d$ represents a metal. Ts each represent carbon or nitrogen. $R^{92}$s to $R^{95}$s each independently represent a substituent. When Ts represent nitrogen, $R^{94}$s and $R^{95}$s are not present.

The compound represented by General Formula (V) will be described below.

In General Formula (V), M represents any metal. Preferred examples thereof include the above-described metals as the metals selected from groups 7 to 11 of the periodic table.

The bidentate ligands L and L' in General Formula (V) represent ligands having partial structures described below.

[Chem. 37]

L:

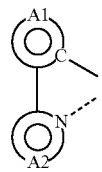

[Chem. 38]

L':

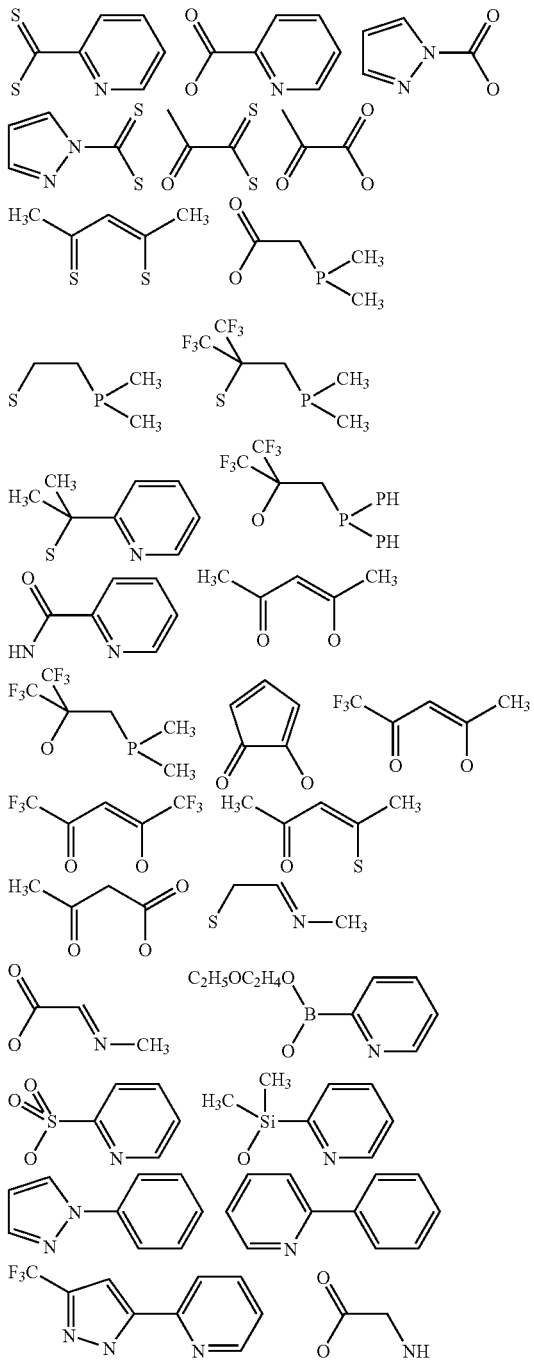

From the viewpoint of the stability of the complex, particularly preferred examples of L' are shown below.

[Chem. 39]

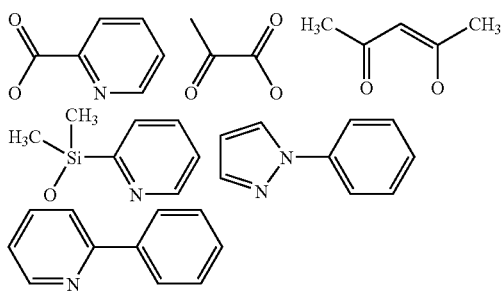

In the partial structures of L and L', ring A1 represents an optionally-substituted aromatic hydrocarbon group or an optionally-substituted aromatic heterocyclic group. Ring A2 represents an optionally-substituted nitrogen-containing aromatic heterocyclic group.

In the case where rings A1 and A2 have substituents, preferred examples of the substituents include halogen atoms such as a fluorine atom; alkyl groups, such as a methyl group and an ethyl group; alkenyl groups such as a vinyl group; alkoxycarbonyl groups, such as a methoxycarbonyl group and an ethoxycarbonyl group; alkoxy groups, such as a methoxy group and an ethoxy group; aryloxy groups, such as a phenoxy group and a benzyloxy group; dialkylamino groups, such as a dimethylamino group and a diethylamino group; diarylamino groups such as a diphenylamino group; a carbazolyl group; acyl groups such as an acetyl group; haloalkyl groups such as a trifluoromethyl group; a cyano group; and aromatic hydrocarbon groups, such as a phenyl group, a naphthyl group, and a phenanthryl group.

More preferred examples of the compound represented by General Formula (V) include compounds represented by General Formulae (Va), (Vb), and (Vc) shown below.

[Chem. 40]

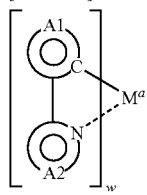 (Va)

In General Formula (Va), $M^a$ represents the same metal as M. w represents the valence of the metal. Ring $A^1$ represents an optionally-substituted aromatic hydrocarbon group. Ring A2 represents an optionally-substituted nitrogen-containing aromatic heterocyclic group.

[Chem. 41]

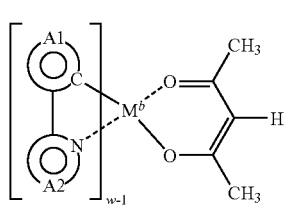 (Vb)

In General Formula (Vb), $M^b$ represents the same metal as M. w represents the valence of the metal. Ring A1 represents an optionally-substituted aromatic hydrocarbon group or an optionally-substituted aromatic heterocyclic group. Ring A2 represents an optionally-substituted nitrogen-containing aromatic heterocyclic group.

[Chem. 42]

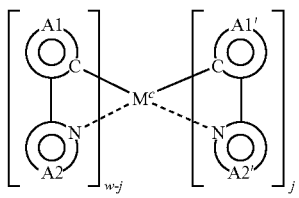 (Vc)

In General Formula (Vc), $M^c$ represents the same metal as M. w represents the valence of the metal. j represents 0, 1, or 2. Ring A1 and ring A1' each independently represent an optionally-substituted aromatic hydrocarbon group or an optionally-substituted aromatic heterocyclic group. Ring A2 and ring A2' each independently represent an optionally-substituted nitrogen-containing aromatic heterocyclic group.

In General Formulae (Va), (Vb), and (Vc), preferred examples of groups of ring A1 and ring A1' include a phenyl group, a biphenyl group, a naphthyl group, an anthryl group, a thienyl group, a furyl group, a benzothienyl group, a benzofuryl group, a pyridyl group, a quinolyl group, an isoquinolyl group, and a carbazolyl group.

Preferred examples of groups of ring A2 and ring A2' include a pyridyl group, a pyrimidyl group, a pyrazyl group, a triazinyl group, a benzothiazole group, a benzoxazole group, a benzimidazole group, a quinolyl group, an isoquinolyl group, a quinoxalyl group, and a phenanthridinyl group.

Examples of substituents that may be provided on the compounds represented by General Formulae (Va), (Vb), and (Vc) include halogen atoms such as a fluorine atom; alkyl groups, such as a methyl group and an ethyl group; alkenyl groups such as a vinyl group; alkoxycarbonyl groups, such as a methoxycarbonyl group and an ethoxycarbonyl group; alkoxy groups, such as a methoxy group and an ethoxy group; aryloxy groups, such as a phenoxy group and a benzyloxy group; dialkylamino groups, such as a dimethylamino group and a diethylamino group; diarylamino groups such as a diphenylamino group; a carbazolyl group; acyl groups such as an acetyl group; haloalkyl groups such as a trifluoromethyl group; and a cyano group.

When the substituent is an alkyl group, the number of carbon atoms is usually 1 to 6. When the substituent is an alkenyl group, the number of carbon atoms is usually 2 to 6. When the substituent is an alkoxycarbonyl group, the number of carbon atoms is usually 2 to 6. When the substituent is an alkoxy group, the number of carbon atoms is usually 1 to 6. When the substituent is an aryloxy group, the number of carbon atoms is usually 6 to 14. When the substituent is a dialkylamino group, the number of carbon atoms is usually 2 to 24. When the substituent is a diarylamino group, the number of carbon atoms is usually 12 to 28. When the substituent is an acyl group, the number of carbon atoms is usually 1 to 14. When the substituent is a haloalkyl group, the number of carbon atoms is usually 1 to 12.

These substituents may be bonded to each other to form a ring. For example, a fused ring may be formed by bonding a substituent provided on ring A1 to a substituent provided on ring A2 or by bonding a substituent provided on ring A1' to a substituent provided on ring A2'.

Examples of such a fused ring group include a 7,8-benzoquinoline group.

Among these, more preferred examples of substituents provided on ring A1, ring A1', ring A2, and ring A2' include alkyl groups, alkoxy groups, aromatic hydrocarbon groups, a cyano group, a halogen atom, haloalkyl groups, diarylamino groups, and a carbazolyl group.

Preferred examples of $M^a$, $M^b$, and $M^c$ in General Formulae (Va), (Vb), and (Vc) include ruthenium, rhodium, palladium, silver, rhenium, osmium, iridium, platinum, and gold.

Specific examples of the organometallic complex represented by Formula (V), (Va), (Vb), or (Vc) are shown below. The organometallic complex is not limited thereto (hereinafter, ph represents a phenyl group).

[Chem. 43]

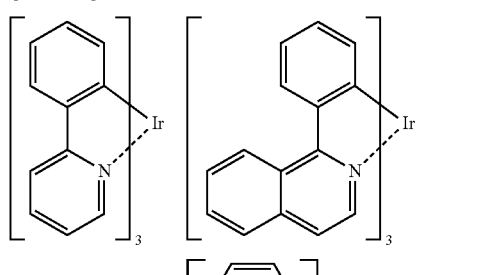

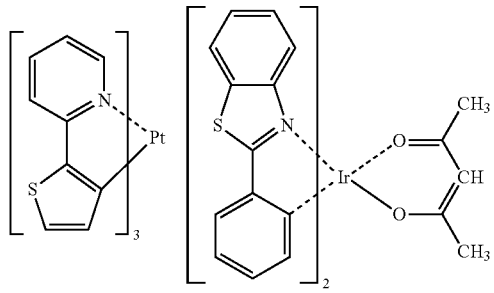

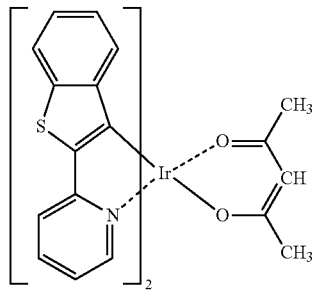

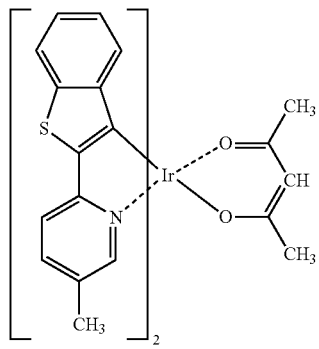

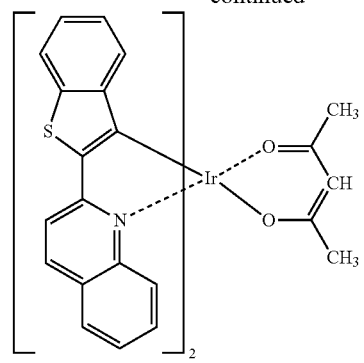

-continued

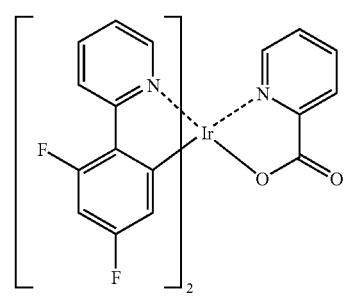

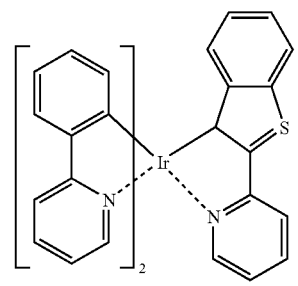

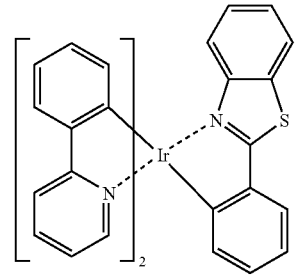

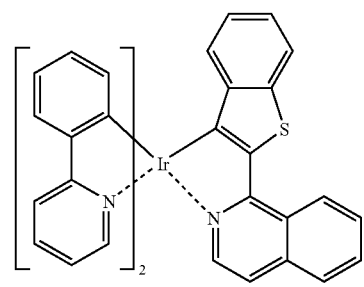

-continued
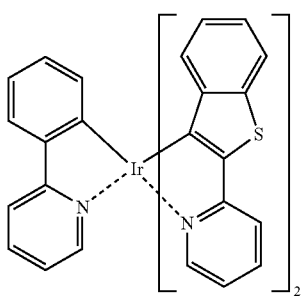
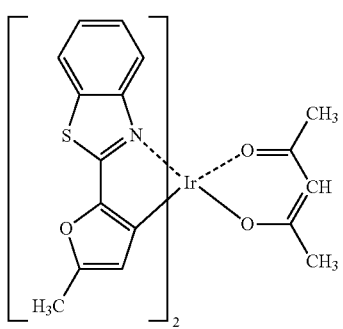
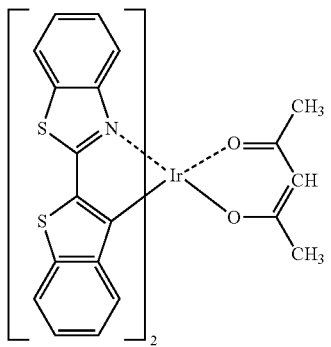
[Chem. 44]
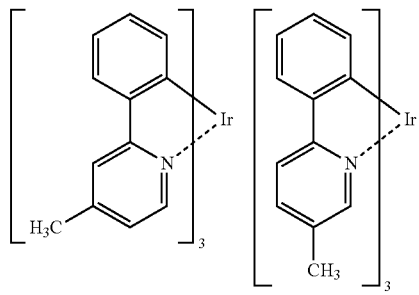
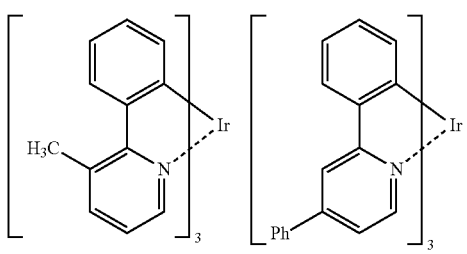
-continued
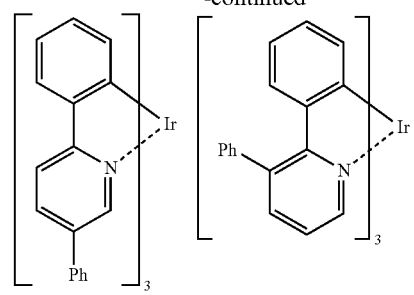
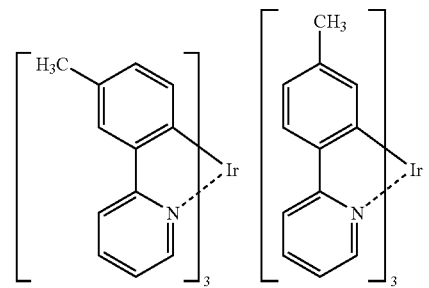
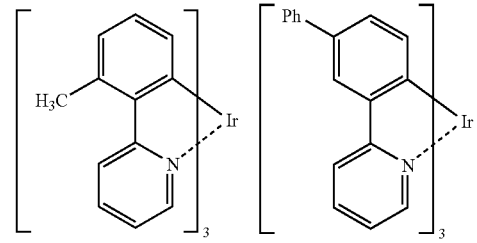
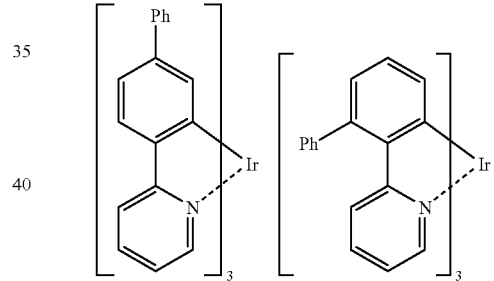
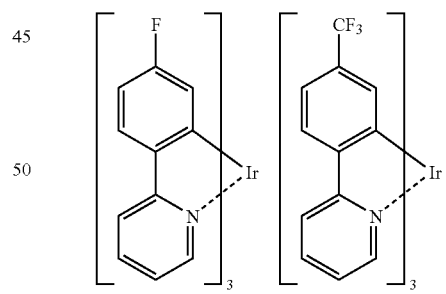
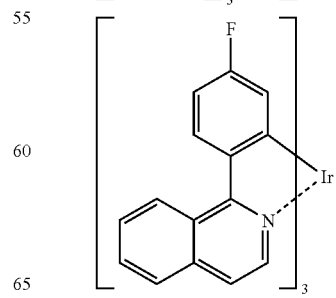

Among these organometallic complexes represented by General Formulae (V), (Va), (Vb), and (Vc), compounds having 2-arylpyridine-based ligands, as the ligand L and/or L', i.e., compounds having 2-arylpyridine, 2-arylpyridine with any substituent, and 2-arylpyridine fused with any group, are particularly preferred.

A compound described in WO 2005/019373 may also be used.

The compound represented by General Formula (VI) will be described below.

In General Formula (VI), $M^d$ represents a metal. Examples thereof include metals described as the metals selected from groups 7 to 11 of the periodic table. Among these, ruthenium, rhodium, palladium, silver, rhenium, osmium, iridium, platinum, and gold are preferred. Divalent metals such as platinum and palladium are particularly preferred.

In General Formula (VI), $R^{92}$s and $R^{93}$s each independently represent a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxy group, an aryloxy group, an aromatic hydrocarbon group, or an aromatic heterocyclic group.

When Ts represent carbon, $R^{94}$s and $R^{95}$s each independently represent the same substituent as that exemplified as each of $R^{92}$s and $R^{93}$s. As described above, when Ts are nitrogen, $R^{94}$s and $R^{95}$s are not present.

Each of $R^{92}$s to $R^{95}$s may have an additional substituent. In this case, the additional substituent is not limited. Any group may be used as the substituent.

Furthermore, $R^{92}$s to $R^{95}$s may be bonded to each other to form a ring. The resulting ring may further have any substituent.

Specific examples (T-1 and T-10 to T-15) of the organometallic complex represented by General Formula (VI) are shown below. The complex is not limited thereto. Hereinafter, Me represents a methyl group. Et represents an ethyl group.

[Chem. 45]

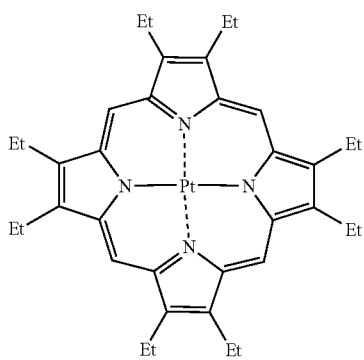

(T-1)

-continued

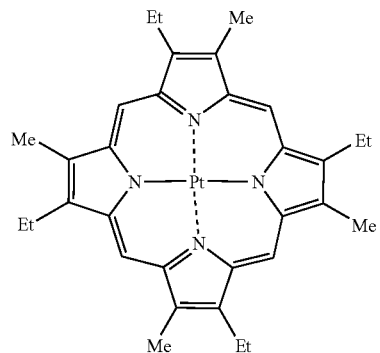

(T-10)

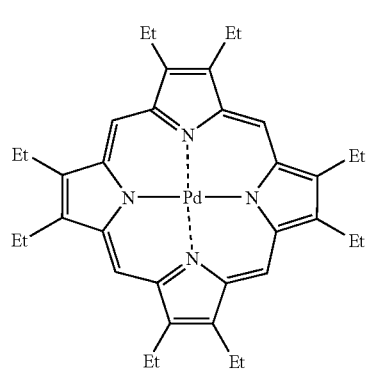

(T-11)

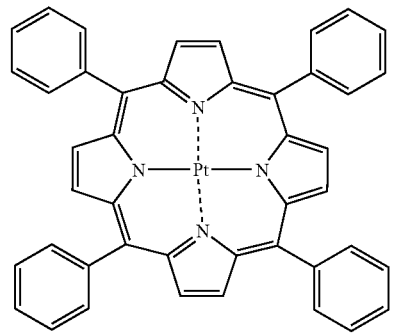

(T-12)

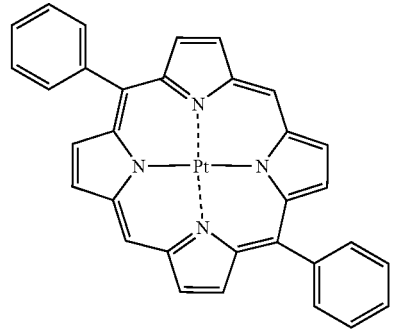

(T-13)

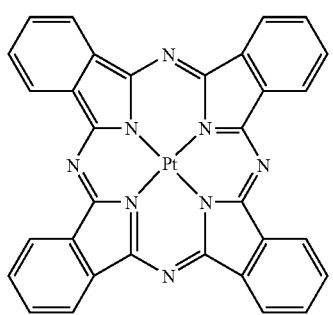

(T-14)

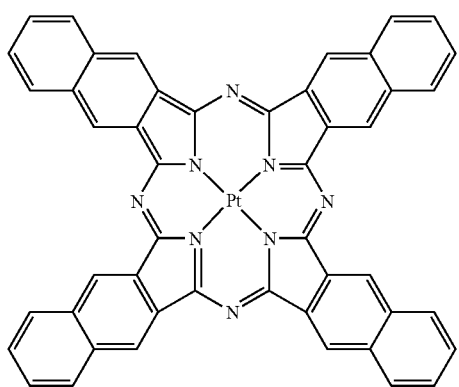

(T-15)

[3] Additional Component

In the composition for charge-transporting material of the present invention, in particular, the composition for charge-transporting material used as the composition for charge-transporting material may contain various other solvents in addition to the above-described solvent and luminescent material, as needed. Examples of other solvents include amides, such as N,N-dimethylformamide and N,N-dimethylacetamide; and dimethyl sulfoxide.

Furthermore, various additives, such as a leveling agent and an antifoaming agent, may be incorporated therein.

In the case where two or more layers are stacked by a wet film-forming method, for the purpose of preventing the layers from mixing with each other, a photocurable resin or a thermosetting resin may be incorporated therein in order that the resin is insolubilized by curing after film formation.

[4] Concentration and Mixing Ratio of Material in Composition for Charge-Transporting Material With respect to the solid content of the composition for charge-transporting material, in particular, the concentration of the solid components, such as the charge-transporting material, the luminescent material, and a component (e.g., a leveling agent) that can be added as needed, is usually 0.01 percent by weight or more, preferably 0.05 percent by weight or more, more preferably 0.1 percent by weight or more, still more preferably 0.5 percent by weight or more, and most preferably 1 percent by weight, and usually 80 percent by weight or less, preferably 50 percent by weight or less, more preferably 40 percent by weight or less, still more preferably 30 percent by weight or less, and most preferably 20 percent by weight or less. At a solid content of less than the lower limit, it is difficult to form a thin film having a relatively large thickness. At a solid content exceeding the upper limit, it may be difficult to form a thin film.

In the composition for charge-transporting material of the present invention, in particular, in the composition for charge-transporting material, the mixing ratio by weight of luminescent material/charge-transporting material is usually 0.1/99.9 or more, more preferably 0.5/99.5 or more, still more preferably 1/99 or more, and most preferably 2/98 or more, and usually 50/50 or less, more preferably 40/60 or less, still more preferably 30/70 or less, and most preferably 20/80 or less. When the ratio is less than the lower limit or exceeds the upper limit, light-emission efficiency may be significantly reduced.

[5] Method for Preparing Composition for Charge-Transporting Material

In the composition for charge-transporting material of the present invention, in particular, the composition for charge-transporting material is prepared by dissolving a solute containing the charge-transporting material, the luminescent material, and various additives, such as a leveling agent and an anti-foaming agent, that can be added as needed in an appropriate solvent. In order to reduce a period of time required for a dissolution step and to maintain the concentration of the solute in the composition at a constant level, the solute is usually dissolved in the solvent while the solvent is stirred. The dissolution step may be performed at room temperature. If the rate of dissolution is low, the mixture may be heated to dissolve the solute. After the completion of the dissolution step, a filtration step of performing filtering may be performed as needed.

[6] Characteristics, Physical Properties, Etc., of Composition for Charge-Transporting Material

[Water Concentration]

In the case where the organic electroluminescent device is produced by forming layers by a wet film-forming method with the composition for charge-transporting material of the present invention (composition for charge-transporting material), the presence of water in the composition for charge-transporting material causes contamination of the film with water, degrading the evenness of the film. Thus, the water content of the composition for charge-transporting material of the present invention, in particular, the water content of the composition for charge-transporting material is preferably minimized. In an organic electroluminescent device, many materials that are significantly deteriorated by water, e.g., the material of a cathode, are generally used. In the case where water is present in the composition for charge-transporting material, a film may contain water after drying. This possibly degrades the properties of the device, which is not preferred.

Specifically, in the water content of the composition for charge-transporting material of the present invention, in particular, the water content of the composition for charge-transporting material is usually 1 percent by weight or less, preferably 0.1 percent by weight or less, more preferably 0.01 percent by weight or less.

As a method for measuring water concentration in the composition for charge-transporting material, a method described in Japanese Industrial Standards "Test methods for water content of chemical products" (JIS K0068: 2001) is preferred. For example, water concentration may be analyzed by the Karl Fischer reagent method (JIS K0211-1348) or the like.

[Homogeneity]

In the composition for charge-transporting material of the present invention, in particular, the composition for charge-transporting material is preferably a homogeneous liquid at room temperature in order to enhance stability in a wet film-forming process, for example, to enhance the stability of discharge of the composition from a nozzle in an ink-jet film-forming method. The phrase "homogeneous liquid at room temperature" means that the composition is a homogeneous-phase liquid and that the composition does not contain a particle component having a particle size of 0.1 μm or more.

[Physical Property]

With respect to the composition for charge-transporting material of the present invention, in particular, with respect to the viscosity of the composition for charge-transporting material, an excessively low viscosity is likely to cause, for example, an uneven film surface due to an excessive flow of a solution film during a film-forming step, the failure of discharge of the composition from a nozzle in an ink-jet film forming process, and the like. An extremely high viscosity is likely to cause nozzle clogging in the ink-jet film-forming process. Accordingly, the viscosity of the composition of the present invention at 25° C. is usually 2 mPa·s or more, preferably 3 mPa·s or more, and more preferably 5 mPa·s or more, and usually 1,000 mPa·s or less, preferably 100 mPa·s or less, and more preferably 50 mPa·s or less.

In the composition for charge-transporting material of the present invention, in particular, a high surface tension of the composition for charge-transporting material may cause problems such as a reduction in the wettability of a film-forming solution to a substrate, a tendency to cause irregularities of a film surface due to poor leveling properties of the solution film during drying, and the like. Therefore, the surface tension of the composition of the present invention at 20° C. is usually less than 50 mN/m and preferably less than 40 mN/m.

In the composition for charge-transporting material of the present invention, in particular, a high vapor pressure of the composition for charge-transporting material may be likely to cause problems such as a change in solute concentration due to solvent evaporation. Thus, the vapor pressure of the composition of the present invention is usually 50 mmHg or less, preferably 10 mmHg or less, and more preferably 1 mmHg or less.

[7] Method for Storing Composition for Charge-Transporting Material

Preferably, the composition for charge-transporting material of the present invention is charged into a vessel that can inhibit the transmission of ultraviolet rays, e.g., a brown glass bottle, securely stoppered, and stored. The storage temperature is usually −30° C. or higher and preferably 0° C. or higher, and usually 35° C. or lower and preferably 25° C. or lower.

[Organic Electroluminescent Device]

An organic electroluminescent device of the present invention includes an anode, a cathode, and a light-emitting layer provided between the electrodes, on a substrate, and is characterized in that the organic electroluminescent device has a layer containing the charge-transporting material of the present invention. The layer containing the charge-transporting material is preferably formed by using the composition for charge-transporting material of the present invention. The layer containing the charge-transporting material is preferably the light-emitting layer. Furthermore, an organometallic complex is preferably doped in the layer containing the charge-transporting material. As the organometallic complex, the compounds exemplified as the luminescent material may be used.

FIGS. 1 to 8 are schematic cross-sectional views showing organic electroluminescent devices according to preferred embodiments of the present invention. In FIG. 1, reference numeral 1 denotes a substrate, reference numeral 2 denotes an anode, reference numeral 3 denotes a hole-injection layer, reference numeral 4 denotes a light-emitting layer, reference numeral 5 denotes an electron-injection layer, and reference numeral 6 denotes a cathode.

[1] Substrate

The substrate 1 is a support of an organic electroluminescent device. A plate of quartz or glass, a metal plate, metal foil, a plastic film, a sheet, or the like is used. In particular, a glass plate or a transparent plate composed of a synthetic resin, e.g., polyester, polymethacrylate, polycarbonate, or polysulfone, is preferred. In the case where a synthetic resin substrate is used, it is necessary to note gas-barrier properties. Excessively low gas-barrier properties of the substrate are not preferred because the organic electroluminescent device may deteriorate due to air that has permeated the substrate.

Thus, a method for forming a dense silicon oxide film or the like on at least one surface of the synthetic resin substrate to ensure gas-barrier properties is one of preferred methods.

[2] Anode

The anode 2 is disposed on the substrate 1. The anode 2 serves as a component which plays a role in the injection of holes toward a layer of the light-emitting-layer side (e.g., the hole-injection layer 3 or the light-emitting layer 4).

The anode 2 is usually composed of a metal such as aluminum, gold, silver, nickel, palladium, or platinum, a metal oxide such as an oxide of indium and/or tin, a metal halide such as copper iodide, carbon black, or a conducting polymer such as poly(3-methylthiophene), polypyrrole, or polyaniline.

Usually, the anode 2 is often formed by sputtering, vacuum evaporation, or the like. In the case where the anode is made by using fine particles of a metal such as silver, fine particles of copper iodide or the like, carbon black, conductive metal-oxide fine particles, or conductive polymer fine particles, the anode 2 may also be formed by dispersing the particles in an appropriate binder resin solution and then applying the resulting mixture on the substrate 1. In the case of a conductive polymer, a thin film may be directly formed on the substrate 1 by electrolytic polymerization, and the conductive polymer may also be applied on the substrate 1 to form the anode 2 (Appl. Phys, Lett., vol. 60, p. 2711 (1992)).

The anode 2 usually has a single-layer structure. Alternatively, the anode 2 may have a laminated structure composed of a plurality of materials, as needed.

The thickness of the anode 2 varies depending on transparency required. In the case where transparency is required, desirably, the light transmittance is usually set at 60% or more and preferably 80% or more. In this case, The thickness of the anode is usually about 5 nm or more and preferably about 10 nm or more, and usually about 1,000 nm or less and preferably about 500 nm or less. In the case where the anode 2 may be opaque, the anode 2 may have any thickness. The anode 2 may also function as the substrate 1. Furthermore, another conductive material may be laminated on the anode 2.

The surface of the anode is preferably subjected to ultraviolet (UV)/ozone treatment, oxygen plasma treatment, or argon plasma treatment in order to remove impurities attached to the anode and improve hole-injection performance by adjusting the ionization potential.

[3] Hole-Injection Layer

The hole-injection layer 3 is a layer that transports holes from the anode 2 to the light-emitting layer 4. Thus, the hole-injection layer 3 preferably contains a hole-transport compound.

In the hole-injection layer 3, a cation radical generated by removing an electron from an electroneutral compound receives an electron from adjacent electroneutral compound. In this way, a hole is moved. In the case where the hole-injection layer 3 does not contain a cation radical compound in the non-energized state of the device, the hole-transport compound provides the anode 2 with an electron in the energized state to form a cation radical of the hole-transport compound. An electron moves between the cation radical and an electroneutral hole-transport compound. In this way, a hole is transported.

In the case where the hole-injection layer 3 contains a cation radical compound, a cation radical is present at a concentration equal to or higher than a concentration of a cation radical generated by oxidation due to the anode 2, improving charge transportability. Thus, the hole-injection layer 3 preferably contains the cation radical compound. The presence of the electroneutral hole-transport compound in the vicinity of the cation radical compound results in a smooth transfer of an electron. Thus, more preferably, the hole-injection layer 3 contains the cation radical compound and the hole-transport compound.

The term "cation radical compound" refers to an ionic compound constituted by a cation radical, which is a chemical species generated by removing an electron from the hole-transport compound, and its counter anion. The cation radical compound contains easily movable holes (free carriers).

The mixing of the hole-transport compound with an electron-accepting compound results in the transfer of an electron from the hole-transport compound to the electron-accepting compound, thereby forming the above-described cation radical compound. Thus, preferably, the hole-injection layer 3 contains the hole-transport compound and the electron-accepting compound.

The above-described preferred materials are summarized as follows: The hole-injection layer 3 preferably contains the hole-transport compound. More preferably, the hole-injection layer 3 contains both of the hole-transport compound and the electron-accepting compound. Furthermore, the hole-injection layer 3 preferably contains the cation radical compound. More preferably, the hole-injection layer 3 contains both of the cation radical compound and the hole-transport compound.

As needed, the hole-injection layer 3 further contains a binder resin and an application-property modifier which do not easily contribute to charge trapping.

Figure 7:
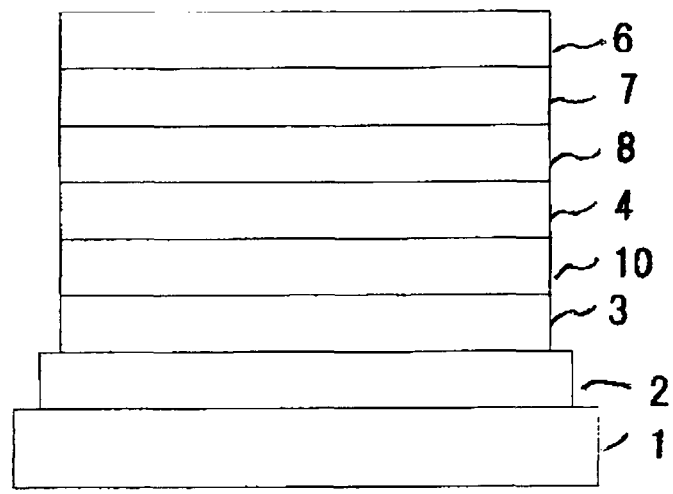
FIG. 7 is a schematic cross-sectional view of an organic electroluminescent device according to another embodiment of the present invention.
Figure 8:
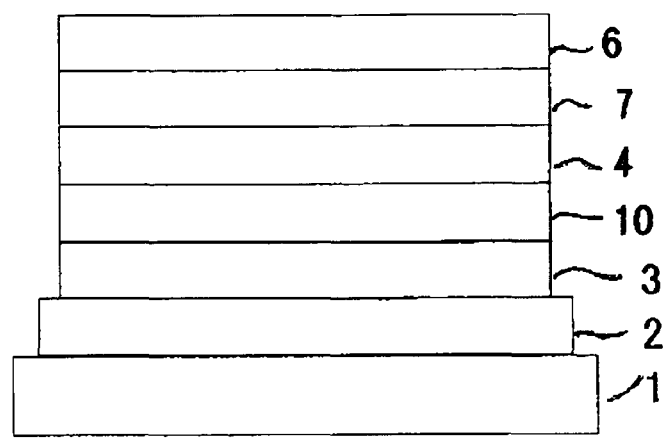
FIG. 8 is a schematic cross-sectional view of an organic electroluminescent device according to another embodiment of the present invention.

It is also possible to form the hole-injection layer 3 on the anode 2 by a wet film-forming method with only the electron-accepting compound or both of the electron-accepting compound and the hole-transport compound and then applying or evaporating the composition for charge-transporting material of the present invention thereon to form a laminate. In this case, the interaction between the electron-accepting compound and a part or the whole of the composition for charge-transporting material of the present invention results in a hole-transport layer 10 having excellent hole-injection performance as shown in FIGS. 7 and 8.

[Hole-Transport Compound]

As the hole-transport compound, a compound having an ionization potential of 4.5 eV to 6.0 eV is preferred.

Examples of the hole-transport compound include aromatic amine compounds, phthalocyanine derivatives, porphyrin derivatives, oligothiophene derivatives, and polythiophene derivatives, in addition to the hole-transport compound of the present invention. Among these, aromatic amine compounds are preferred from the viewpoint of achieving a good amorphous nature and transmittance of visible light.

Among aromatic amine compounds, aromatic tertiary amine compounds such as the hole-transport compound of the present invention are particularly preferred. The phrase "aromatic tertiary amine compounds" refers to compounds each having an aromatic tertiary amine structure and includes compounds having groups derived from aromatic tertiary amines.

The type of aromatic tertiary amine is not particularly limited. Polymer compounds each having a weight-average molecular weight of 1,000 to 1,000,000 (polymeric organic compounds each having a structure in which repeating units are linked) are more preferred from the viewpoint of achieving a good surface-smoothing effect.

Examples of aromatic tertiary amine polymer compounds include polymer compounds having a repeating unit represented by General Formula (VII) shown below.

[Chem. 46]

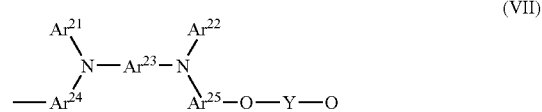

(VII)

In General Formula (VII), $Ar^{21}$ and $Ar^{22}$ each independently represent an optionally-substituted aromatic hydrocarbon group or an optionally-substituted aromatic heterocyclic group. $Ar^{23}$ to $Ar^{25}$ each independently represent an optionally-substituted divalent aromatic hydrocarbon group or an optionally-substituted divalent aromatic heterocyclic group. Y represents a linking group selected from linking groups shown below. Among $Ar^{21}$ to $Ar^{25}$, two groups attached to the same N atom may be bonded to each other to form a ring.

[Chem. 47]

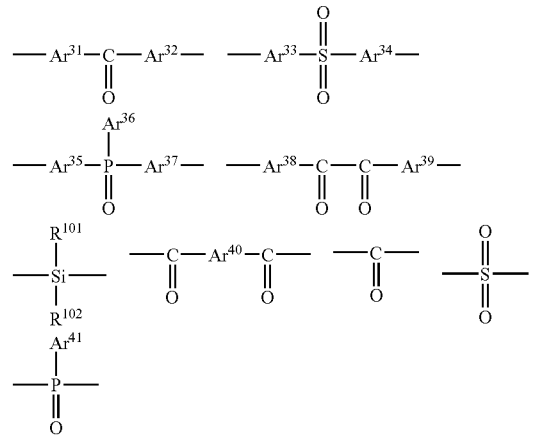

In the formulae shown above, $Ar^{31}$ to $Ar^{41}$ each independently represent a mono- or di-valent group derived from an optionally-substituted aromatic hydrocarbon ring or an optionally-substituted aromatic heterocyclic ring. $R^{101}$ and $R^{102}$ each independently represent a hydrogen atom or any substituent.

As each of $Ar^{21}$ to $Ar^{25}$ and $Ar^{31}$ to $Ar^{41}$, a mono- or di-valent group derived from any of aromatic hydrocarbon rings or aromatic heterocyclic rings may be applied. These may be the same or different. Furthermore, these may have any substituents.

As the aromatic hydrocarbon rings, 5- or 6-membered monocycles and 2- to 5-fused rings are exemplified. Examples thereof include a benzene ring, a naphthalene ring, an anthracene ring, a phenanthrene ring, a perylene ring, a tetracene ring, a pyrene ring, a benzpyrene ring, a chrysene ring, a triphenylene ring, an acenaphthene ring, a fluoranthene ring, and a fluorene ring.

As the aromatic heterocyclic rings, 5- or 6-membered monocycles and 2- to 4-fused rings are exemplified. Examples thereof include a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofurane ring, a thienofuran ring, a benzoisoxazole ring, a benzoisothiazole ring, a benzoimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazolinone ring, and an azulene ring.

Two or more divalent groups derived from one type or two types of aromatic hydrocarbon rings and/or aromatic heterocyclic rings exemplified above may be bonded and used as each of $Ar^{23}$ to $Ar^{25}$, $Ar^{31}$ to $Ar^{35}$, and $Ar^{37}$ to $Ar^{40}$.

$Ar^{21}$ to $Ar^{41}$, which are the groups derived from the aromatic hydrocarbon rings and/or the aromatic heterocyclic rings, may have additional substituents. Each of the substituents preferably has a molecular weight of usually about 400 or less and preferably about 250 or less. The type of substituent is not particularly limited. One type or two or more types selected from substituent group D described below are exemplified.

[Substituent Group D]

Substituent group D includes alkyl groups, such as a methyl group and an ethyl group, each usually having 1 to 10 and preferably 1 to 8 carbon atoms; alkenyl groups, such as a vinyl group, each usually having 2 to 11 and preferably 2 to 5 carbon atoms; alkynyl groups, such as an ethynyl group, each usually having 2 to 11 and preferably 2 to 5 carbon atoms; alkoxy groups, such as a methoxy group and an ethoxy group, each usually having 1 to 10 and preferably 1 to 6 carbon atoms; aryloxy groups, such as a phenoxy group, a naphthoxy group, and a pyridyloxy group, each having a carbon number of usually 4 or more and preferably 5 or more, and usually 25 or less and preferably 14 or less; alkoxycarbonyl groups, such as a methoxycarbonyl group and an ethoxycarbonyl group, each usually having 2 to 11 and preferably 2 to 7 carbon atoms; dialkylamino groups, such as a dimethylamino group and diethylamino group, each usually having 2 to 20 and preferably 2 to 12 carbon atoms; diarylamino groups, such as a diphenylamino group, a ditolylamino group, and an N-carbazolyl group, each having a carbon number of usually 10 or more an preferably 12 or more, and usually 30 or less and preferably 22 or less; arylalkylamino groups, such as a phenylmethylamino group, each having a carbon number of usually 6 or more and preferably 7 or more, and usually 25 or less and preferably 17 or less; acyl groups, such as an acetyl group and a benzoyl group, each usually having 2 to 10 and preferably 2 to 7 carbon atoms; halogen atoms, such as a fluorine atom and a chlorine atom; haloalkyl groups, such as a trifluoromethyl group, each usually having 1 to 8 and preferably 1 to 4 carbon atoms; alkylthio groups, such as a methylthio group and an ethylthio group, each usually having 1 to 10 and preferably 1 to 6 carbon atoms; arylthio groups, such as a phenylthio group, a naphthylthio group, and a pyridylthio group, each having a carbon number of usually 4 or more and preferably 5 or more, and usually 25 or less and preferably 14 or less; silyl groups, such as a trimethylsilyl group and a triphenylsilyl group, each having a carbon number of usually 2 or more and preferably 3 or more, and usually 33 or less and preferably 26 or less; siloxy groups, such as a trimethylsiloxy group and a triphenylsiloxy group, each having a carbon number of usually 2 or more and preferably 3 or more, and usually 33 or less and preferably 26 or less; aromatic hydrocarbon group, such as a phenyl group and a naphthyl group, each usually having 6 to 30 and preferably 6 to 18; and aromatic heterocyclic groups, such as a thienyl group and a pyridyl group, each having a carbon number of usually 3 or more and preferably 4 or more, and usually 28 or less and preferably 17 or less.

As $Ar^{21}$ and $Ar^{22}$, monovalent groups derived from a benzene ring, a naphthalene ring, a phenanthrene ring, a thiophene ring, and a pyridine ring are preferred, and a phenyl group and a naphthyl group are more preferred, from the viewpoints of achieving good solubility of the polymer compound, heat resistance, hole-injection performance, and hole transportability.

As $Ar^{23}$ to $Ar^{25}$, divalent groups derived from a benzene ring, a naphthalene ring, an anthracene ring, and a phenanthrene ring are preferred, and a phenylene group, a biphenylene group, and a naphthylene group are more preferred, from the viewpoints of achieving good hole-injection performance and hole transportability including heat resistance and oxidation-reduction potential.

As each of $R^{101}$ and $R^{102}$, a hydrogen atom or any substituent may be applied. These may be the same or different. The type of substituent is not particularly limited. Examples of the substituent that may be applied include alkyl groups, alkenyl groups, alkynyl groups, alkoxy groups, a silyl group, a siloxy group, aromatic hydrocarbon groups, aromatic heterocyclic groups, and halogen atoms. Specific examples thereof include the groups exemplified in substituent group D.

Specific examples of the aromatic tertiary amine polymer compound having the repeating unit represented by General Formula (VII) include compounds described in WO 2005/089024. The same is true in preferred examples thereof. For example, Compound (PB-1) represented by a structural formula shown below is exemplified. However, the polymer compound is not limited thereto.

[Chem. 48]

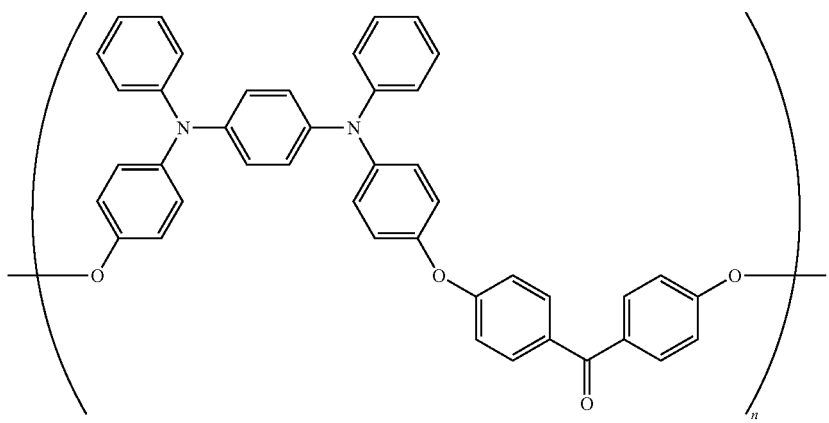

PB-1

Preferred examples of another aromatic tertiary amine polymer compound include polymer compounds each having a repeating unit represented by General Formula (VIII) and/or General Formula (IX) shown below.

[Chem. 49]

(VIII)

(IX)

In General Formulae (VIII) and (IX), $Ar^{45}$, $Ar^{47}$, and $Ar^{48}$ each independently represent an optionally-substituted aromatic hydrocarbon group or an optionally-substituted aromatic heterocyclic group. $Ar^{44}$ and $Ar^{46}$ each independently represent an optionally-substituted divalent aromatic hydrocarbon group or an optionally-substituted divalent aromatic heterocyclic group. Among $Ar^{45}$ to $Ar^{48}$, two groups attached to the same N atom may be bonded to each other to form a ring. $R^{111}$ to $R^{113}$ each independently represent a hydrogen atom or any substituent.

Specific examples and preferred examples of $Ar^{45}$, $Ar^{47}$, and $Ar^{48}$ and examples and preferred examples of a substituent that may be provided thereon are the same as those of $Ar^{21}$ and $Ar^{22}$. Specific examples and preferred examples of $Ar^{44}$ and $Ar^{46}$ and examples and preferred examples of a substituent that may be provided thereon are the same as those of $Ar^{23}$ to $Ar^{25}$. Each of $R^{111}$ to $R^{113}$ preferably represents a hydrogen atom or the substituent described in [substituent group D] and more preferably a hydrogen atom, an alkyl group, an alkoxy group, an amino group, or an aromatic hydrocarbon group.

Specific examples of the aromatic tertiary amine polymer compound having the repeating unit represented by General Formula (VIII) and/or (IX) include compounds described in WO 2005/089024. The same is true in preferred examples thereof. However, the polymer compound is not limited thereto.

In the case where the hole-injection layer is formed by a wet film-forming method, a hole-transport compound that is easily soluble in various solvents is preferred. As the aromatic tertiary amine compounds, for example, a binaphthyl-based compound (Japanese Unexamined Patent Application Publication No. 2004-014187) and an unsymmetrical 1,4-phenylenediamine compound (Japanese Unexamined Patent Application Publication No. 2004-026732) are preferred.

A compound that is easily soluble in various solvents may be appropriately selected from aromatic amine compounds previously used as materials for forming hole-injection and hole-transport thin films in organic electroluminescent devices. Examples of aromatic amine compounds that may be used as the hole-transport compounds for the hole-injection layer include known compounds that have been used as materials for forming hole-injection and hole-transport layers. Examples thereof include aromatic diamine compounds each having a structure in which tertiary aromatic amine units are linked, e.g., 1,1-bis(4-di-p-tolylaminophenyl)cyclohexane (Japanese Unexamined Patent Application Publication No. 59-194393); aromatic amine compounds each having two or more tertiary amines and two or more fused aromatic rings attached to nitrogen atoms, e.g., 4,4'-bis[N-(1-naphthyl)-N-phenylamino]biphenyl (Japanese Unexamined Patent Application Publication No. 5-234681); aromatic triamine compounds that are triphenylbenzene derivatives each having a starburst structure (U.S. Pat. No. 4,923,774); aromatic diamine compounds such as N,N'-diphenyl-N,N'-bis(3-methylphenyl)biphenyl-4,4'-diamine (U.S. Pat. No. 4,764,625); α,α,α',α'-tetramethyl-α,α'-bis(4-di(p-tolyl)aminophenyl)-p-xylene (Japanese Unexamined Patent Application Publication No. 3-269084); triphenylamine derivatives each having a sterically asymmetrical structure as the entire molecule (Japanese Unexamined Patent Application Publication No. 4-129271); compounds in which a pyrenyl group is substituted with a plurality of aromatic diamino groups (Japanese Unexamined Patent Application Publication No. 4-175395); aromatic diamine compounds each having a structure in which aromatic tertiary amine units are linked with an ethyelen group (Japanese Unexamined Patent Application Publication No. 4-264189); aromatic diamines each having a styryl structure (Japanese Unexamined Patent Application Publication No. 4-290851); compounds each having a structure in which aromatic tertiary amine units are linked with a thiophene group (Japanese Unexamined Patent Application Publication No. 4-304466); starburst aromatic triamine compounds (Japanese Unexamined Patent Application Publication No. 4-308688); benzylphenyl compounds (Japanese Unexamined Patent Application Publication No. 4-364153); compounds each having a structure in which tertiary amines are linked with a fluorene group (Japanese Unexamined Patent Application Publication No. 5-25473); triamine compounds (Japanese Unexamined Patent Application Publication No. 5-239455); bisdipyridylaminobiphenyl (Japanese Unexamined Patent Application Publication No. 5-320634); N,N,N-triphenylamine derivatives (Japanese Unexamined Patent Application Publication No. 6-1972); aromatic diamines each having a phenoxazine structure (Japanese Unexamined Patent Application Publication No. 7-138562); diaminophenylphenanthridine derivatives (Japanese Unexamined Patent Application Publication No. 7-252474); hydrazone compounds (Japanese Unexamined Patent Application Publication No. 2-311591); silazane compounds (U.S. Pat. No. 4,950,950); silanamine derivatives (Japanese Unexamined Patent Application Publication No. 6-49079); phosphamine derivatives (Japanese Unexamined Patent Application Publication No. 6-25659); and quinacridone compounds. These aromatic amine compounds may be used as a mixture of two or more, as needed.

Preferred examples of phthalocyanine derivatives or porphyrin derivatives that may be used as the hole-transport compounds for the hole-injection layer include porphyrin, 5,10,15,20-tetraphenyl-21H,23H-porphyrin, 5,10,15,20-tetraphenyl-21H,23H-porphyrin cobalt(II), 5,10,15,20-tetraphenyl-21H,23H-porphyrin copper(II), 5,10,15,20-tetraphenyl-21H,23H-porphyrin zinc(II), 5,10,15,20-tetraphenyl-21H,23H-porphyrin vanadium(IV) oxide, 5,10, 15,20-tetra(4-pyridyl)-21H,23H-porphyrin, copper(II) 29H, 31H-phthalocyanine, zinc(II) titanium phthalocyanine, phthalocyanine, magnesium phthalocyanine oxide, lead phthalocyanine, copper(II) phthalocyanine, and 4,4',4",4"'-tetraaza-29H,31H-phthalocyanine.

Preferred examples of oligothiophene derivatives that may be used as the hole-transport compounds for the hole-injection layer include α-terthiophene and derivatives thereof; α-sexithiophene and derivatives thereof; and oligothiophene derivatives each having a naphthalene ring (Japanese Unexamined Patent Application Publication No. 6-256341).

Preferred examples of polythiophene derivatives that may be used as the hole-transport compound of the present invention include poly(3,4-ethylenedioxythiophene) (PEDOT) and poly(3-hexylthiophene).

The molecular weight of the hole-transport compound is usually 9,000 or less and preferably 5,000 or less, and usually 200 or more and preferably 400 or more, except in the case of a polymer compound (polymer compound in which repeating units are linked). An excessively high molecular weight of the hole-transport compound makes it difficult to perform the synthesis and purification, which is not preferred. An excessively low molecular weight may reduce heat resistance, which is also not preferred.

With respect to the hole-transport compound used as a material for the hole-injection layer, these compounds may be contained alone or two or more. When two or more hole-transport compounds are contained, any combination may be used. A combination of one or tow or more aromatic tertiary amine polymer compounds and one or two or more other hole-transport compounds is preferred.

[Electron-Accepting Compound]

As the electron-accepting compound, an oxidative compound having the ability to receive an electron form the above-described hole-transport compound is preferred. Specifically, a compound having an electron affinity of 4 eV or more is preferred. A compound having an electron affinity of 5 eV or more is more preferred.

Examples thereof include organic group-substituted onium salts such as 4-isopropyl-4'-methyldiphenyliodonium tetrakis(pentafluorophenyl)borate, iron(III) chloride (Japanese Unexamined Patent Application Publication No. 11-251067), high-valence inorganic compounds such as ammonium peroxodisulfate, cyano compounds such as tetracyanoethylene, aromatic boron compounds such as tris(pentafluorophenyl) borane (Japanese Unexamined Patent Application Publication No. 2003-31365), fullerene derivatives, and iodine.

Among these compounds, organic group-substituted onium salts and high-valence inorganic compounds are preferred in view of strong oxidizing power. Organic group-substituted onium salts, cyano compounds, and aromatic boron compounds are preferred in view that they are soluble in various solvent and can be applied by wet application.

Specific examples of organic group-substituted onium salts, cyano compounds, and aromatic boron compounds, which are suitable as electron-accepting compounds include compounds described in WO 2005/089024. The same is true in preferred examples thereof. For example, Compound (A-2) represented by a structural formula shown below is exemplified. However, the electron-accepting compound is not limited thereto.

[Chem. 50]

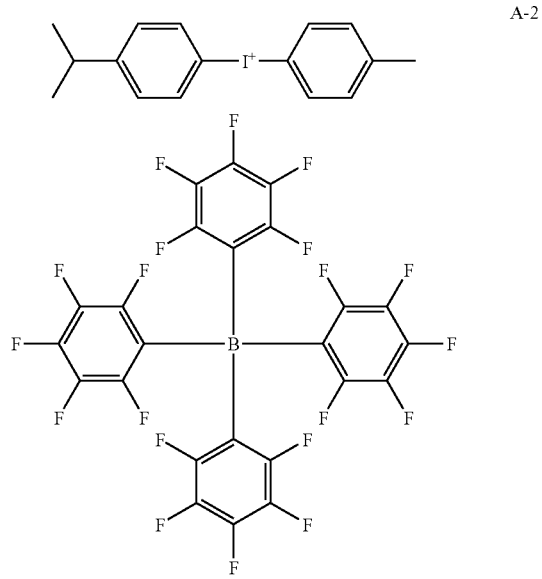

A-2

[Cation Radical Compound]

A cation radical compound refers to an ionic compound constituted by a cation radical, which is a chemical species generated by removing an electron from the hole-transport compound, and its counter anion. In the case where the cation radical is derived from a hole-transport polymer compound, the cation radical has a structure in which an electron is removed from the repeating unit of the polymer compound.

The cation radical is preferably a chemical species generated by removing an electron from the compound exemplified as the hole-transport compound. More preferably, the cation radical is a chemical species generated by removing an electron from the compound exemplified as the preferred hole-transport compound from the viewpoints of achieving a good amorphous nature, transmittance of visible light, heat resistance, solubility, and the like.

The cation radical compound can be formed by mixing the above-described hole-transport compound and the electron-accepting compound. That is, The mixing of the hole-transport compound with an electron-accepting compound results in the transfer of an electron from the hole-transport compound to the electron-accepting compound, thereby forming the cation radical compound constituted by the cation radical derived from the hole-transport compound and its counter anion.

Cation radical compounds derived from polymer compounds such as PEDOT/PSS (Adv. Mater., 2000, vol. 12, p. 481) and an emeraldine hydrochloride (J. Phys. Chem., 1990, vol. 94, p. 7716), are also formed by oxidative polymerization (dehydrogenative polymerization), i.e., by chemically or electrochemically oxidation of a monomer in an acidic solution with peroxodisulfate or the like. In the case of oxidative polymerization (dehydrogenative polymerization), a cation radical in which an electron is removed from a repeating unit of the polymer is formed, its counter anion being an anion from the acidic solution, while the monomer is polymerized by oxidation.

The hole-injection layer 3 is formed on the anode 2 by a wet film-forming method or vacuum evaporation.

Indium-tin oxide (ITO), which is typically used as the anode 2, has disadvantages in that a short-circuit fault occurs easily because the surface roughness is about 10 nm (Ra) and local projections are often formed. The formation of the hole-injection layer 3 on the anode 2 by the wet film-forming method advantageously reduces the occurrence of a defective device due to irregularities of the surface of the anode, compared with the case in which the hole-injection layer 3 is formed by vacuum evaporation.

In the case of the formation of the layer by the wet film-forming method, a predetermined amount of one or two or more of the above-described materials (the hole-transport compound, the electron-accepting compound, and the cation radical compound) are dissolved in a solvent. If necessary, a binder resin and an application-property modifier which do not easily contribute to charge trapping are added therein, preparing a coating solution. The resulting coating solution is applied on the anode by the wet film-forming method, e.g., spin coating, spray coating, dip coating, die coating, flexographic printing, screen printing, or an ink-jet method. After drying, the hole-injection layer 3 is formed.

With respect to the solvent used for forming the layer by the wet film-forming method, the type of solvent is not particularly limited as long as the solvent can dissolve the above-described materials (the hole-transport compound, the electron-accepting compound, and the cation radical compound). Preferably, the solvent does not contain an inactivating material or a material that generates an inactivating material which may inactivate the materials (the hole-transport compound, the electron-accepting compound, and the cation radical compound) used for the hole-injection layer.

Preferred examples of the solvent that satisfies the requirements include ether solvents and ester solvents. Specific examples of the ether solvents include aliphatic ethers, such as ethylene glycol dimethyl ether, ethylene glycol diethyl ether, and propylene glycol-1-monomethyl ether acetate (PGMEA); and aromatic ethers, such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole. Examples of the ester solvents include aliphatic esters, such as ethyl acetate, n-butyl acetate, ethyl lactate, and n-butyl lactate; and aromatic esters, such as phenyl acetate, phenyl propionate, methyl benzoate, ethyl benzoate, propyl benzoate, and n-butyl benzoate. These may be used alone. Alternatively, two or more among them may be combined in any proportion.

Usable examples of the solvent other than the ether solvents and the ester solvents include aromatic hydrocarbon solvents, such as benzene, toluene, and xylene; amide solvents, such as N,N-dimethylformamide and N,N-dimethylacetamide; and dimethyl sulfoxide. These may be used alone. Alternatively, two or more among them may be combined in any proportion. Furthermore, one or two or more among these solvents may be used in combination of one or two or more among the above-described ether solvents and ester solvents. In particular, the aromatic hydrocarbon solvents, such as benzene, toluene, and xylene have a low ability to dissolve the electron-accepting compound and the cation radical compound. Thus, preferably, the aromatic hydrocarbon solvents are used as mixtures of the aromatic hydrocarbon solvents, the ether solvents, and the ester solvents.

The concentration of the solvent in the coating solution is usually 10 percent by weight or more, preferably 30 percent by weight or more, and more preferably 50 percent by weight or more, and usually 99.999 percent by weight or less, preferably 99.99 percent by weight or less, and more preferably 99.9 percent by weight or less. In the case where a mixture of two or more solvents is used, the sum of concentrations of these solvents satisfies the range.

In the case of the formation of the layer by vacuum evaporation, one or two or more of the above-described materials (the hole-transport compound, the electron-accepting compound, and the cation radical compound) are charged into a crucible placed in a vacuum chamber (when two or more materials are used, the materials are charged into respective crucibles). After the vacuum chamber is evacuated to about $10^{-4}$ Pa with an appropriate vacuum pump, the crucible is heated (when two or more materials are used, each of the crucibles is heated) to evaporate the material while the amount of evaporation is controlled (when two or more materials are used, the materials are evaporated while amounts of evaporation are independently controlled). Thereby, the hole-injection layer is formed on an anode of a substrate facing the crucible. In the case where two or more materials are used, the hole-injection layer may also be formed by charging a mixture of the materials to a crucible and evaporating the mixture by heating.

The thickness of the resulting hole-injection layer 3 is usually 5 nm or more and preferably 10 nm or more, and usually 1,000 nm or less and preferably 500 nm or less.

Figure 6:
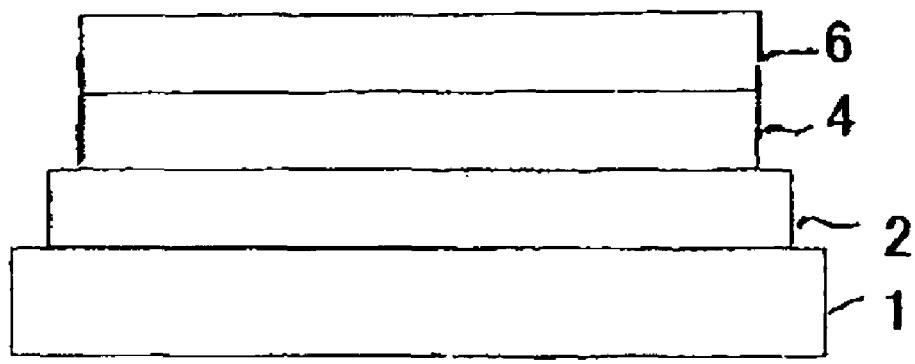
FIG. 6 is a schematic cross-sectional view of an organic electroluminescent device according to another embodiment of the present invention.

As shown in FIG. 6, the hole-injection layer 3 may be omitted.

[4] Light-Emitting Layer

The light-emitting layer 4 is usually provided on the hole-injection layer 3. The light-emitting layer 4 is a layer containing a luminescent material. The layer is excited by recombination of holes injected from the anode 2 through the hole-injection layer 3 with electrons injected from the cathode 6 through the electron-injection layer 5 between the electrodes to which an electric field is applied, functioning as a main source of luminescence. The light-emitting layer 4 preferably contains the luminescent material (dopant) and one or two or more host materials. More preferably, the light-emitting layer 4 contains the charge-transporting material of the present invention as the host material. The light-emitting layer 4 may be formed by vacuum evaporation. Particularly preferably, the light-emitting layer 4 is a layer formed by a wet film-forming method with the composition for charge-transporting material of the present invention.

The wet film-forming method means that the composition for charge-transporting material of the present invention containing the solvent is applied by spin coating, spray coating, dip coating, die coating, flexographic printing, screen printing, or an ink-jet method, to form a film.

The light-emitting layer 4 may contain other materials and components within a range in which performance of the present invention is not impaired.

In organic electroluminescent devices, in the case where the same materials are used, smaller thicknesses of films provided between electrodes generally increase an effective electric field and a current injected, thereby reducing a driving voltage. Thus, a smaller total thickness of the films provided between the electrodes reduces the driving voltage of the organic electroluminescent device. An excessively small thickness causes a short-circuit due to projections of the electrodes composed of ITO or the like. Therefore, a certain length of the thickness is needed.

In the present invention, in the case where organic layers, such as the hole-injection layer 3 and the electron-transport layer 5 described below, are provided in addition to the light-emitting layer 4, the total thickness of the light-emitting layer 4 and the other organic layers, such as the hole-injection layer 3 and the electron-injection layer 5, is usually 30 nm or more, preferably 50 nm or more, and more preferably 100 nm or more, and usually 1,000 nm or less, preferably 500 nm or less, and more preferably 300 nm or less. In the case where the hole-injection layer 3 and the electron-transport layer 5 described below other than the light-emitting layer 4 have high conductivity, the quantity of electric charge injected into the light-emitting layer 4 is increased. Thus, for example, the driving voltage can be reduced while the total thickness is maintained at a certain level by increasing the thickness of the hole-injection layer 3 and reducing the thickness of the light-emitting layer 4.

Accordingly, the thickness of the light-emitting layer is usually 10 nm or more and preferably 20 nm or more, and usually 300 nm or less and preferably 200 nm or less. In the case where the device of the present invention has only the light-emitting layer 4 provided between the anode and the cathode, the thickness of the light-emitting layer 4 is usually 30 nm or more and preferably 50 nm or more, and usually 500 nm or less and preferably 300 nm or less.

[5] Electron-Injection Layer

The electron-injection layer 5 plays a role in effectively injecting electrons, which are injected from the cathode 6, into the light-emitting layer 4. To achieve efficient electron injection, a material for the electron-injection layer 5 is preferably a low-work-function metal. An alkali metal, e.g., sodium or cesium, or an alkaline-earth metal, e.g., barium or calcium, is used.

The electron-injection layer 5 preferably has a thickness of 0.1 to 5 nm.

The arrangement of an ultrathin insulating film (0.1 to 5 nm) composed of LiF, MgF$_2$, Li$_2$O, CsCO$_3$, or the like at an interface between the cathode 6 and the light-emitting layer 4 or between the cathode 6 and an electron-transport layer 7 described below is an effective method for improving the efficiency of the device (Appl. Phys. Lett., vol. 70, p. 152, 1997; Japanese Unexamined Patent Application Publication No. 10-74586; IEEE Trans. Electron. Devices, vol. 44, p. 1245, 1997; SID 04 Digest, p. 154).

Doping an organic electron-transport material such as a nitrogen-containing heterocyclic compound, e.g., bathophenanthroline, or a metal complex, e.g., a 8-hydroxyquinoline aluminum complex, with an alkali metal such as sodium, potassium, cesium, lithium, or rubidium (described in Japanese Unexamined Patent Application Publication No. 10-270171, Japanese Unexamined Patent Application Publication No. 2002-100478, Japanese Unexamined Patent Application Publication No. 2002-100482, and the like) improves electron-injection performance and electron transportability and results in an excellent-quality film, which is preferred. In this case, the thickness is usually 5 nm or more and preferably 10 nm or more, and usually 200 nm or less and preferably 100 nm or less.

The electron-injection layer 5 is formed (stacked) on the light-emitting layer 4 by a wet film-forming method or vacuum evaporation as in the light-emitting layer 4. In the case of vacuum evaporation, an evaporation source is charged into a crucible or a metal boat placed in a in a vacuum chamber. After the vacuum chamber is evacuated to about $10^{-4}$ Pa with an appropriate vacuum pump, the crucible or the metal boat is heated to evaporate the source. Thereby, the electron-injection layer is formed on a substrate facing the crucible or the metal boat.

Evaporation of an alkali metal is performed with an alkali metal dispenser in which an alkali metal chromate and a reductant are charged into nichrome. Heating the dispenser in a vacuum chamber reduces the alkali metal chromate, evaporating the alkali metal. In the case where an organic electron-transport material and an alkali metal are co-evaporated, the organic electron-transport material is charged into a crucible placed in a vacuum chamber. After the vacuum chamber is evacuated to about $10^{-4}$ Pa with an appropriate vacuum pump, each of the crucible and the dispenser are simultaneously heated to evaporate them. Thereby, the electron-injection layer is formed on a substrate facing the crucible and the dispenser.

In this case, co-evaporation is uniformly performed in the thickness direction of the electron-injection layer 5. Alternatively, the electron-injection layer 5 may have concentration distribution in the thickness direction.

As shown in FIGS. 5, 6, 7, and 8, the electron-injection layer 5 may be omitted.

[6] Cathode

The cathode 6 plays a role in injecting electrons into a layer (e.g., the electron-injection layer 5 or the light-emitting layer 4) adjacent to the light-emitting layer. The material for the anode 2 may also be used for the cathode 6. To achieve efficient electron injection, a low-work-function metal is preferred. An appropriate metal, e.g., tin, magnesium, indium, calcium, aluminum, or silver, or an alloy thereof is used. Specific examples thereof include electrodes composed of low-work-function alloys, such as magnesium-silver alloys, magnesium-indium alloys, and aluminum-lithium alloys.

The cathode 6 usually has the same thickness as the anode 2. To protect the cathode composed of the low-work-function metal, a metal layer having a high work function and stability to air is stacked thereon. This increases the stability of the device. To this end, a metal, e.g., aluminum, silver, copper, nickel, chromium, gold, or platinum, is used.

[7] Additional Constitutional Layer

The device having the layer structure shown in FIG. 1 has been described above. Any layer may be provided between the light-emitting layer 4 and the anode 2 or the cathode 6 of the organic electroluminescent device of the present invention in addition to the above-described layers as long as the performance is not impaired. Furthermore, any of the layers other than the light-emitting layer 4 may be omitted.

Figure 2:
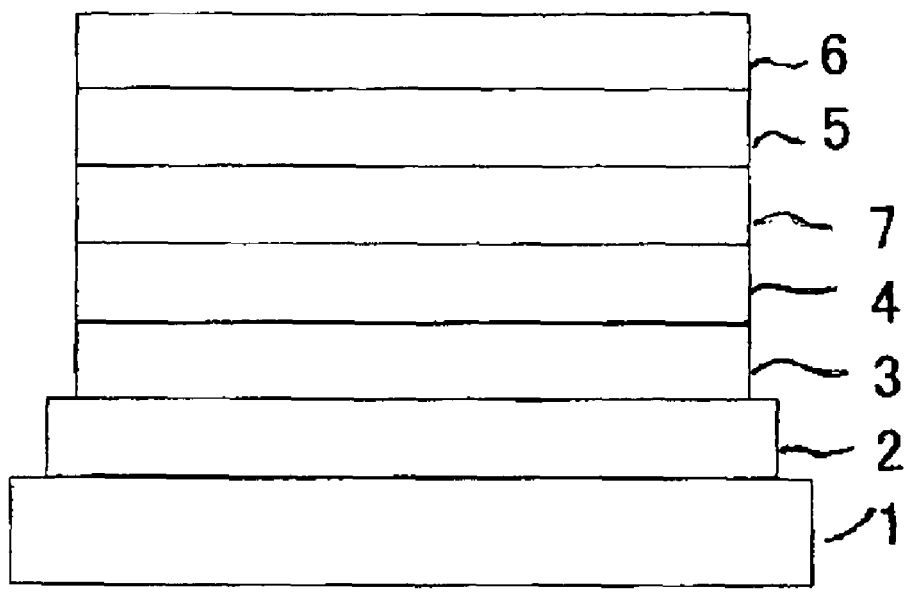
FIG. 2 is a schematic cross-sectional view of an organic electroluminescent device according to another embodiment of the present invention.

An example of the layer that may be provided is an electron-transport layer 7. As shown in FIG. 2, the electron-transport layer 7 is provided between the light-emitting layer 4 and the electron-injection layer 5 in order to further improve the light-emission efficiency of the device.

The electron-transport layer 7 is composed of a compound capable of efficiently transporting electrons, which are injected from the cathode 6, toward the light-emitting layer 4. An electron-transport compound used for the electron-transport layer 7 needs to have the high efficiency of electron injection from the cathode 6 or the electron-injection layer 5 and have high electron mobility and be capable of efficiently transporting electrons injected.

Examples of a material that satisfies the requirements include 8-hydroxyquinoline metal complexes such as a 8-hydroxyquinoline aluminum complex (Japanese Unexamined Patent Application Publication No. 59-194393), 10-hydroxybenzo[h]quinoline metal complexes, oxadiazole derivatives, distyrylbiphenyl derivatives, silole derivatives, 3- or 5-hydroxyflavone metal complexes, benzoxazole metal complexes, benzothiazole metal complexes, trisbenzimidazolylbenzene (U.S. Pat. No. 5,645,948), quinoxaline compounds (Japanese Unexamined Patent Application Publication No. 6-207169), phenanthroline derivatives (Japanese Unexamined Patent Application Publication No. 5-331459), 2-tert-butyl-9,10-N,N'-dicyanoanthraquinonediimine, n-type hydrogenated amorphous silicon carbide, n-type zinc sulfide, and n-type zinc selenide.

The lower limit of the thickness of the electron-transport layer 7 is usually about 1 nm and preferably about 5 nm. The upper limit thereof is usually about 300 nm and preferably about 100 nm.

The electron-transport layer 7 is formed (stacked) on the light-emitting layer 4 by a wet film-forming method or vacuum evaporation as in the hole-injection layer 3. Usually, vacuum evaporation is employed.

In the present invention, preferably, the hole-transport layer 10 is provided. The hole-transport layer 10 preferably contains the charge-transporting material of the present invention. The compounds exemplified as the hole-transport compound for the hole-injection layer may also be used. Alternatively, polymer materials, such as polyvinylcarbazol, polyvinyltriphenylamine, and poly(arylene ether sulfone) containing tetraphenylbenzidine, may be used. The hole-transport layer 10 is formed by stacking any of these materials on the hole-injection layer by the wet film-forming method or vacuum evaporation. The thickness of the hole-transport layer 10 is usually 10 nm or more and preferably 30 nm, and usually 300 nm or less and preferably 100 nm or less.

Figure 3:
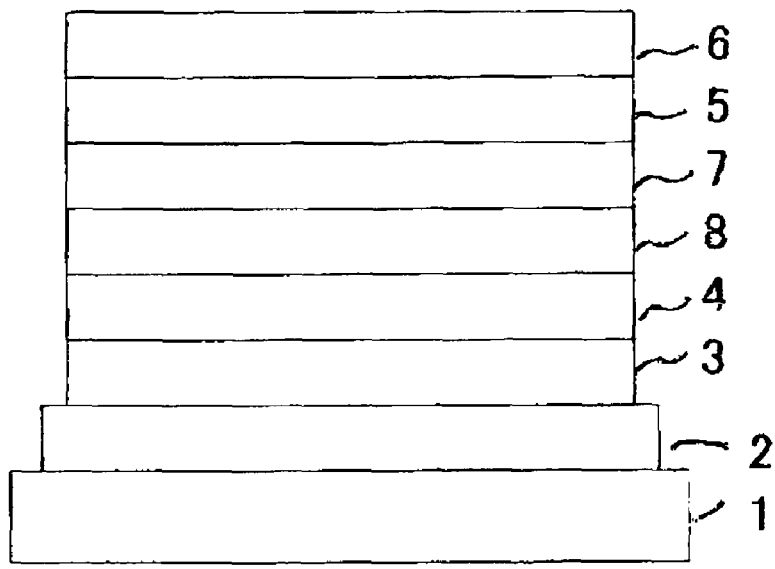
FIG. 3 is a schematic cross-sectional view of an organic electroluminescent device according to another embodiment of the present invention.

In particular, in the case where a phosphorescent material or a blue-luminescent material is used as a luminescent material, as shown in FIG. 3, a hole-inhibition layer 8 is effectively provided. The hole-inhibition layer 8 has a function to trap holes and electrons in the light-emitting layer 4 to improve luminescent efficiency. That is, the hole-inhibition layer 8 has a role to inhibit holes transferred from the light-emitting layer 4 from reaching the electron-transport layer 7 to increase recombination probability, trapping excitons formed in the light-emitting layer 4. The hole-inhibition layer 8 also has a role to efficiently transport electrons, which are injected from the electron-transport layer 8, toward the light-emitting layer 4.

The hole-inhibition layer 8 is composed of a compound which has a role to inhibit holes transferred from the anode 2 from reaching the cathode 6 and which is capable of efficiently transporting electrons injected from the cathode 6 toward the light-emitting layer 4. The hole-inhibition layer 8 is formed (stacked) on the light-emitting layer 4 so as to be in contact with the surface of the light-emitting layer 4 adjacent to the cathode 6.

The material constituting the hole-inhibition layer 8 needs to have physical properties such as high electron mobility, low hole mobility, a large energy gap (large difference in energy between HOMO and LUMO), and a high excited triplet level (T1).

Examples of a material for the hole-injection layer which satisfies the requirements include mixed ligand complexes, such as bis(2-methyl-8-quinolinolato)(phenolato)aluminum and bis(2-methyl-8-quinolinolato)(triphenylsilanolato)aluminum; metal complexes, such as dinuclear metal complexes, e.g., bis(2-methyl-8-quinolato)aluminum-μ-oxo-bis-(2-methyl-8-quinolylato)aluminum; styryl compounds such as distyrylbiphenyl derivatives (Japanese Unexamined Patent Application Publication No. 11-242996); triazole derivatives such as 3-(4-biphenylyl)-4-phenyl-5(4-tert-butylphenyl)-1, 2,4-triazole (Japanese Unexamined Patent Application Publication No. 7-41759), and phenanthroline derivatives such as bathocuproin (Japanese Unexamined Patent Application Publication No. 10-79297).

A compound having at least one pyridine ring substituted in the 2-, 4-, and 6-positions, described in WO 2005/022962, is also preferred as a hole-inhibition material.

The thickness of the hole-inhibition layer 8 is usually 0.3 nm or more and preferably 0.5 nm or more, and usually 100 nm or less and preferably 50 nm or less.

The hole-inhibition layer 8 may also be formed by the same method as in the hole-injection layer 3. Usually, vacuum evaporation is employed.

The electron-transport layer 7 and the hole-inhibition layer 8 may be appropriately provided as needed. In other words, for example, 1) only the electron-transport layer is provided, 2) only the hole-inhibition layer is provided, 3) a laminate of hole-inhibition layer/electron-transport layer is provided, or 4) they are not provided. As shown in FIG. 7, the hole-inhibition layer 8 and the electron-transport layer 7 may be stacked without the electron-injection layer 5. As shown in FIG. 8, only the electron-transport layer 7 may be provided.

Figure 4:
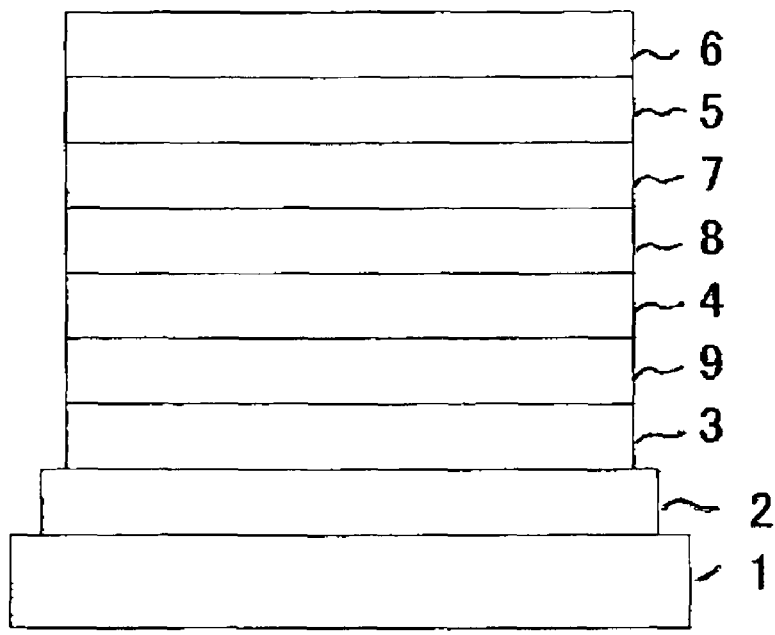
FIG. 4 is a schematic cross-sectional view of an organic electroluminescent device according to another embodiment of the present invention.
Figure 5:
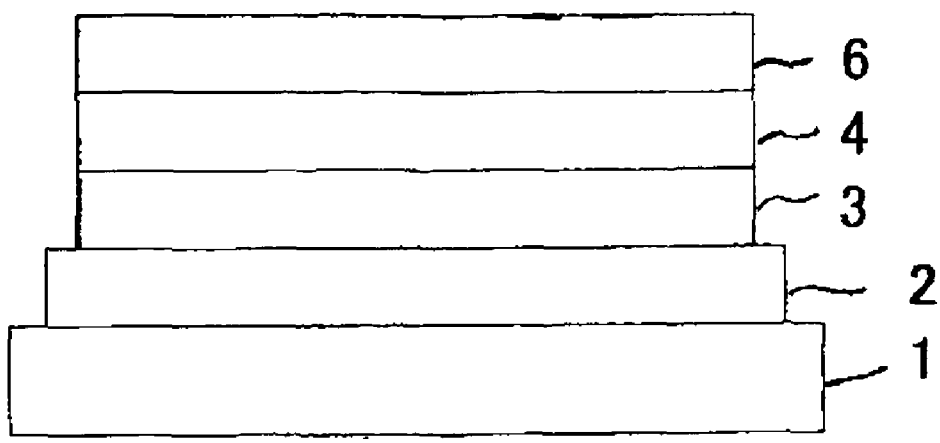
FIG. 5 is a schematic cross-sectional view of an organic electroluminescent device according to another embodiment of the present invention.

For the same purpose as the hole-inhibition layer 8, as shown in FIG. 4, an electron-inhibition layer 9 is also effectively provided between the hole-injection layer 3 and the light-emitting layer 4. The electron-inhibition layer 9 has a role to inhibit electrons transferred from the light-emitting layer 4 from reaching the hole-injection layer 3 to increase recombination probability, trapping excitons formed in the light-emitting layer 4. The electron-inhibition layer 9 also has a role to efficiently transport holes, which are injected from the hole-injection layer 3, toward the light-emitting layer 4.

The electron-inhibition layer 9 needs to have properties, such as high hole mobility, a large energy gap (large difference in energy between HOMO and LUMO), and a high excited triplet level (T1). In the case where the light-emitting layer 4 is formed by a wet film-forming method, the formation of the electron-inhibition layer 9 by the wet film-forming method facilitates the production of the device, which is preferred.

Therefore, preferably, the electron-inhibition layer 9 can be formed by the wet film-forming method. Examples of a material for the electron-inhibition layer 9 include copolymers of dioctylfluorene and triphenylamine, e.g., F8-TFB, (described in WO 2004/084260).

The inverse structure of that shown in FIG. 1, i.e., the cathode 6, the electron-injection layer 5, the light-emitting layer 4, the hole-injection layer 3, and the anode 2 stacked in that order on the substrate 1, may be used. As described above, the organic electroluminescent device of the present invention may be provided between two substrates, at least one of the two substrates having high transparency. Similarly, inverse structures of the above-described layer structures shown in FIGS. 2 to 8 may be used.

Furthermore, a structure in which a plurality of layer structures shown in FIG. 1 are stacked (a plurality of luminescent units are stacked) may be used. In this case, for example, when $V_2O_5$ is used as a charge-generating layer (CGL) in place of interface layers (when the anode is composed of ITO and the cathode is composed of Al, the two layers are the interface layers) between the layer structures (between the luminescent units), the barrier between the layer structures is reduced, which is more preferred in view of the light-emission efficiency and driving voltage.

The present invention is applied to an organic electroluminescent device composed of a single device. Alternatively, the present invention is also applied to a device having a structure in which organic electroluminescent devices are arrayed. Furthermore, the present invention is applied to a structure in which an anode and a cathode are arrayed in an X-Y matrix.

EXAMPLES

While the present invention will be described in detail below by examples, the present invention is not limited to the description of the examples without departing from the scope of the invention.

[Synthesis Example of Organic Compound of the Invention]

Examples of the synthesis of the organic compounds of the present invention will be described below.

In each of the following examples, the glass transition temperature was determined by DSC measurement. The vaporization temperature was determined by TG-DTA measurement. The melting point was determined by the DSC measurement or TG-DTA measurement.

Example 1

Target Compounds 1 and 2

[Chem. 51]

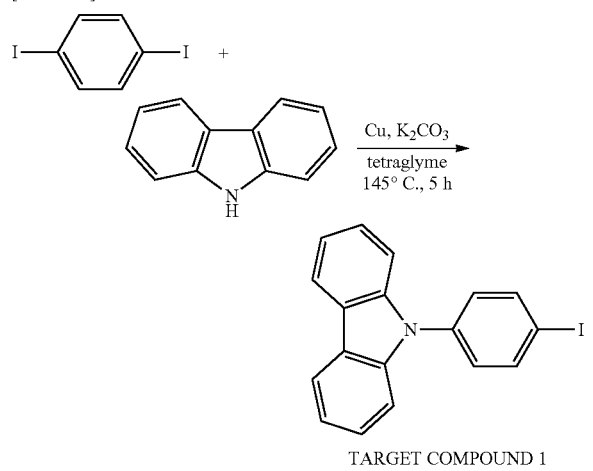

TARGET COMPOUND 1

Under a nitrogen stream, carbazole (12.7 g), p-diiodobenzene (25.0 g), a copper powder (4.82 g), potassium carbonate (21.0 g), and tetraglyme (45 mL) were stirred at 145° C. for 5 hours and then left standing to cool to room temperature. Chloroform was added to the reaction mixture. The insoluble matter was filtered off. Chloroform contained in the filtrate was evaporated under reduced pressure. Purification was performed by silica-gel column chromatography (n-hexane/toluene: 4/1) to yield Target Compound 1 (11.2 g).

[Chem. 52]

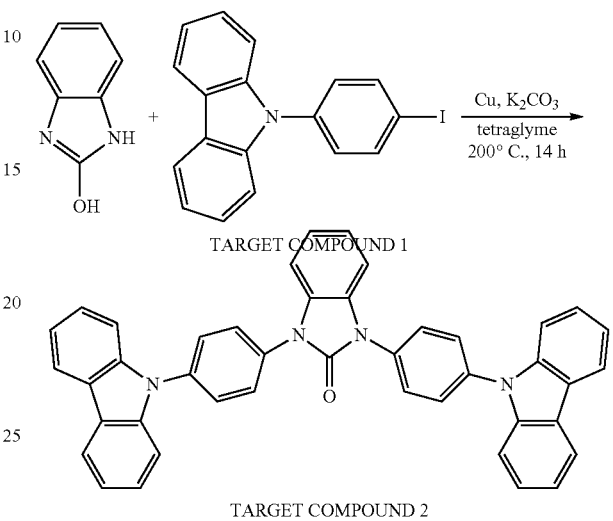

TARGET COMPOUND 2

Under a nitrogen stream, Target Compound 1 (8.01 g), 2-hydroxybenzimidazole (1.04 g), a copper powder (1.38 g), potassium carbonate (6.44 g), and tetraglyme (20 mL) were stirred at 200° C. for 8 hours and then left standing to cool. A copper powder (1.39 g) was added thereto. The resulting mixture was stirred at 200° C. for 6 hours. After the mixture was left standing to cool, chloroform and activated clay were added to the reaction mixture. The mixture was stirred. The insoluble matter was filtered off. Methanol (200 mL) was added thereto. The mixture was stirred. The precipitate was filtered. The resulting solid was purified by silica-gel column chromatography (toluene) and washed with ethyl acetate and a chloroform/methanol mixture to yield Target Compound 2 (1.33 g).

DEI-MS: m/z=616 (M$^+$)

This compound had a glass transition temperature of 146° C., a melting point of 355° C., and a vaporization temperature of 507° C.

The difference in energy between the excited triplet state and the ground state of this compound was 3.04 eV.

Example 2

Target Compounds 3 and 4

[Chem. 53]

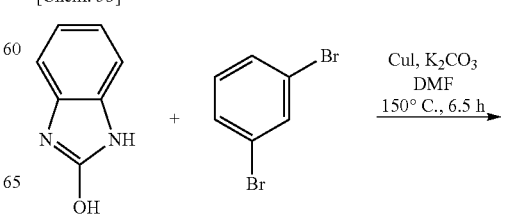

-continued

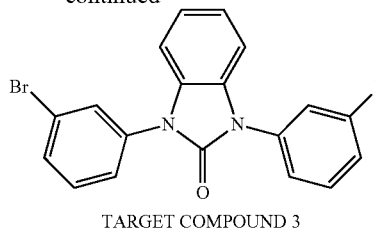

TARGET COMPOUND 3

Under a nitrogen stream, 2-hydroxybenzimidazole (5.41 g), m-dibromobenzene (28.6 g), copper(I) iodide (15.3 g), potassium carbonate (22.3 g), and N,N-dimethylformamide (130 mL) were stirred at 150° C. for 6.5 hours and then left standing to cool to room temperature. Water was added to the reaction mixture. After the mixture was extracted with ethyl acetate, the organic layer was dried over magnesium sulfate and then concentrated to yield a residue. Toluene and activated clay were added to the residue. The resulting mixture was stirred. The insoluble matter was filtered off. Chloroform contained in the filtrate was evaporated under reduced pressure. Methanol was added thereto. The mixture was stirred. The resulting precipitate was recrystallized in methanol to yield Target Compound 3 (4.36 g).

[Chem. 54]

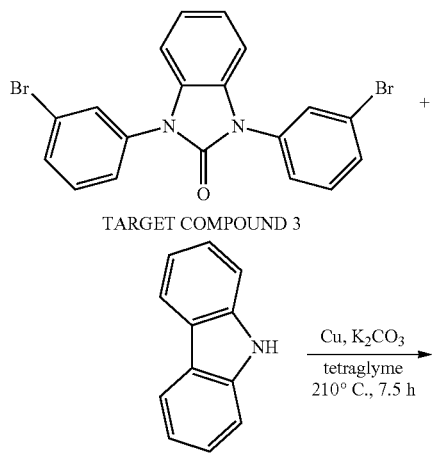

-continued

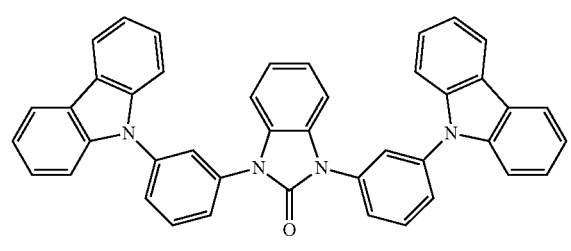

TARGET COMPOUND 4

Under a nitrogen stream, Target Compound 3 (4.36 g), carbazole (5.76 g), a copper powder (1.88 g), potassium carbonate (8.15 g), and tetraglyme (20 mL) were stirred at 210° C. for 7.5 hours and then left standing to cool. Chloroform was added to the reaction mixture. The resulting mixture was stirred. The insoluble matter was filtered off. Methanol (200 mL) was added thereto. After the mixture was stirred, the resulting precipitate was filtered. The solid was purified by silica-gel column chromatography (toluene) and washed with a dichloromethane/methanol mixture to yield Target Compound 4 (2.29 g).

DEI-MS: m/z=616 (M$^+$)

This compound had a glass transition temperature of 125° C., a melting point of 227° C., and a vaporization temperature of 489° C.

This compound was dissolved in toluene in an amount of 3 percent by weight or more.

The difference in energy between the excited triplet state and the ground state of this compound was 2.99 eV.

Example 3

Target Compound 5

[Chem. 55]

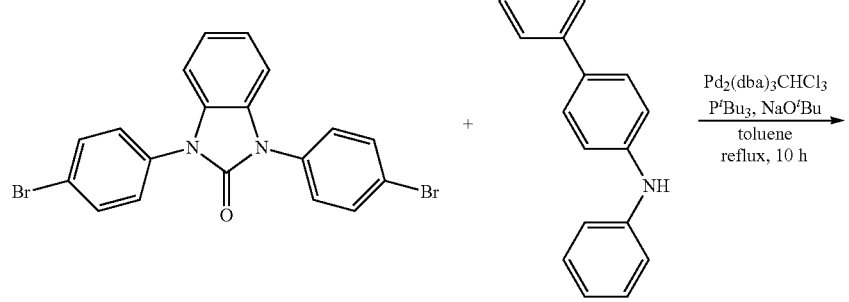

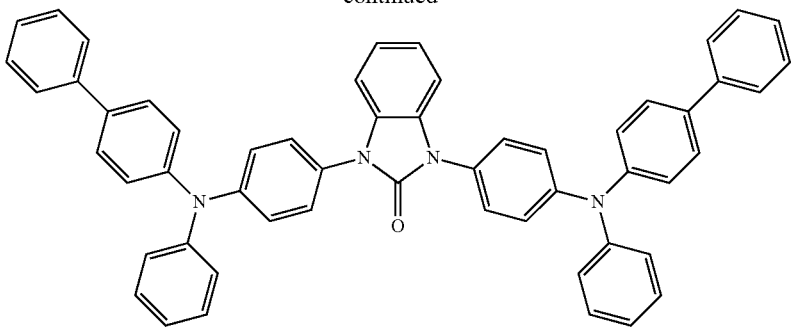

TARGET COMPOUND 5

A tris(dibenzylideneacetone)dipalladium(0)-chloroform complex (0.12 g), tri-tert-butylphosphine (0.209 g), and toluene (5 mL) were stirred at 60° C. for 5 minutes in a nitrogen atmosphere to prepare a solution. Under a nitrogen stream, the resulting solution was added to a solution containing 1,3-bis(4-bromophenyl)-1,3-dihydrobenzimidazol-2-one (2.60 g), N-(4-biphenyl)aniline (4.31 g), sodium tert-butoxide (2.25 g), and toluene (35 mL). The mixture was heated to reflux for 9.5 hours with stirring. After the reaction mixture was left standing to cool, activated clay and chloroform were added thereto. The mixture was stirred. The insoluble matter was filtered off. Methanol (200 mL) was added thereto. After the mixture was stirred, the resulting precipitate was filtered. The solid was purified by silica-gel column chromatography (toluene) and washed with a dichloromethane/methanol mixture to yield Target Compound 5 (2.55 g).

DEI-MS: m/z=772 (M$^+$)

This compound had a glass transition temperature of 124° C. and a vaporization temperature of 527° C. The melting point thereof was not observed. This compound was dissolved in toluene in an amount of 5.0 percent by weight or more.

Example 4

Target Compound 6

[Chem. 56]

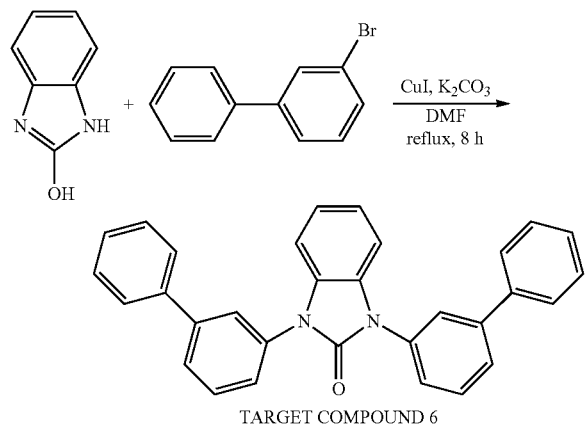

TARGET COMPOUND 6

Under a nitrogen stream, 2-hydroxybenzimidazole (1.03 g), 3-bromobiphenyl (5.00 g), copper(I) iodide (2.92 g), potassium carbonate (4.23 g), and N,N-dimethylformamide (10 mL) were heated to reflux for 8 hours with stirring and then left to standing to cool. Chloroform was added to the reaction mixture. The resulting mixture was stirred. The insoluble matter was filtered off. The filtrate was concentrated. The concentrate was purified by silica-gel column chromatography and subjected to suspension washing with methanol to yield Target Compound 6 (2.68 g).

EI-MS: m/z=438 (M$^+$)

This compound had a glass transition temperature of 56° C., a melting point of 150° C., and a vaporization temperature of 391° C. This compound was dissolved in toluene in an amount of 5.0 percent by weight or more.

Example 5

Target Compounds 7 to 9

[Chem. 57]

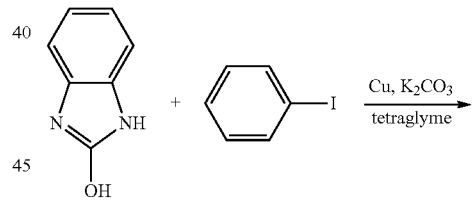

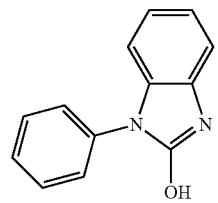

TARGET COMPOUND 7

Under a nitrogen stream, 2-hydroxybenzimidazole (6.53 g), iodobenzene (9.93 g), a copper powder (3.11 g), potassium carbonate (13.5 g), and tetraglyme (15 mL) were stirred at 170° C. for 4 hours and then left standing to cool. Ethyl acetate and water were added to the reaction mixture. The resulting mixture was stirred. The organic layer was dried over magnesium sulfate and then concentrated. The concentrate was purified by silica-gel column chromatography (a n-hexane/ethyl acetate mixture to ethyl acetate) and subjected to suspension washing with n-hexane to yield Target Compound 7 (3.87 g).

[Chem. 58]

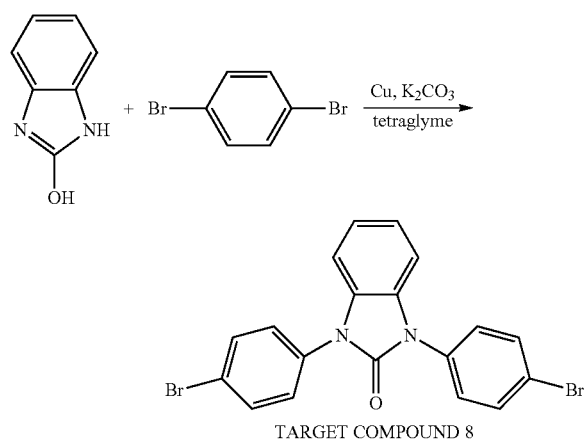

Under a nitrogen stream, 2-hydroxybenzimidazole (7.58 g), p-dibromobenzene (40.0 g), a copper powder (10.8 g), potassium carbonate (46.9 g), and tetraglyme (40 mL) were stirred at 200° C. for 12 hours and then left standing to cool. Ethyl acetate was added to the reaction mixture. The resulting mixture was heated to reflux for 30 minutes with stirring and then left standing to cool. The insoluble matter was filtered off. The filtrate was concentrated. The precipitate was subjected to suspension washing with ethanol, purified by silica-gel column chromatography (a n-hexane/toluene mixture to toluene), and subjected to suspension washing with methanol to yield Target Compound 8 g).

[Chem. 59]

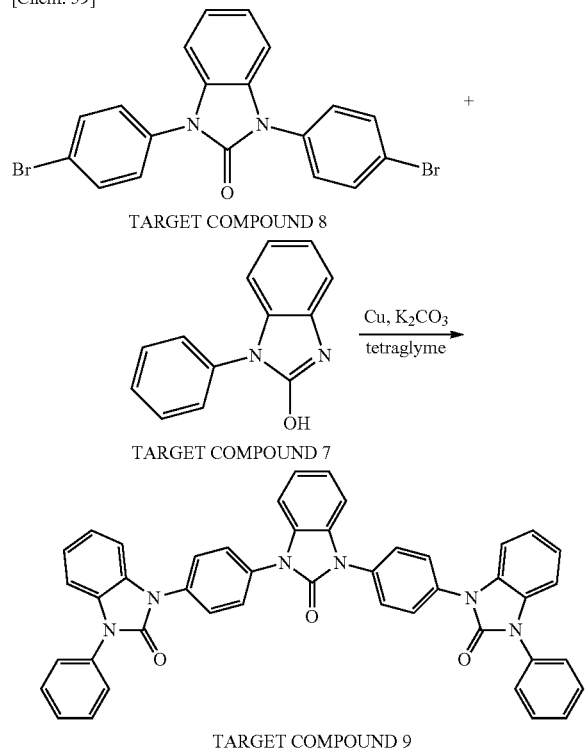

Under a nitrogen stream, Target Compound 8 (0.860 g), Target Compound 7 (1.22 g), a copper powder (0.492 g), potassium carbonate (2.14 g), and tetraglyme (6 mL) were stirred at 200° C. for 14 hours and then left standing to cool. Chloroform was added to the reaction mixture. The mixture was stirred for 30 minutes. The insoluble matter was filtered off. The filtrate was concentrated. The resulting precipitate was subjected to suspension washing with ethanol, purified by silica-gel column chromatography (a n-hexane/ethyl acetate mixture), and subjected to suspension washing with an ethyl acetate/ethanol mixture to yield Target Compound 9 (0.465 g).

DEI-MS: m/z=702 (M$^+$)

This compound had a glass transition temperature of 150° C., a melting point of 328° C., and a vaporization temperature of 527° C.

The difference in energy between the excited triplet state and the ground state of this compound was 3.2 eV or more.

Example 6

Target Compounds 10 and 11

[Chem. 60]

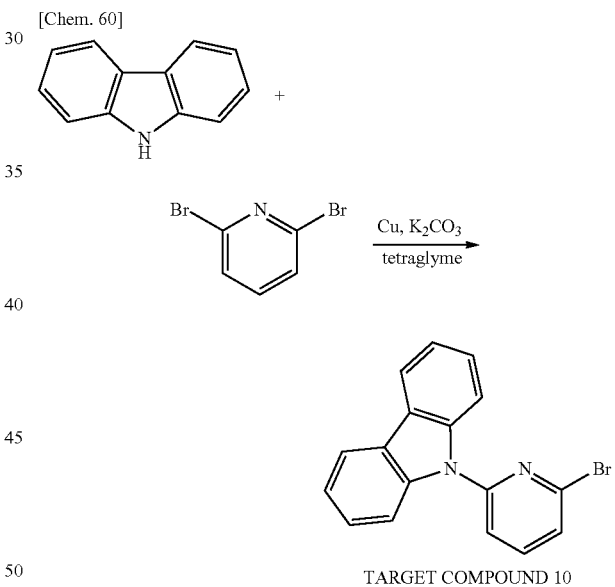

Under a nitrogen stream, carbazole (18.8 g), 2,6-dibromopyridine (80.0 g), a copper powder (14.4 g), potassium carbonate (31.2 g), and tetraglyme (80 mL) were stirred at 170° C. for 7 hours and then left standing to cool to room temperature. Chloroform was added to the reaction mixture. The insoluble matter was filtered off. Chloroform contained in the filtrate was evaporated under reduced pressure. An ethanol/water (40/1) mixture was added thereto. The resulting precipitate was filtered off. Water was added to the filtrate. The precipitate was filtered, washed with ethanol, and then purified by silica-gel column chromatography (a n-hexane/methylene chloride mixture) to yield Target Compound 10 (17.7 g).

[Chem. 61]

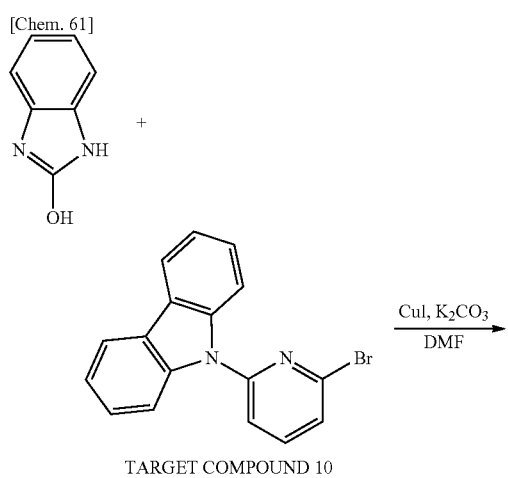

TARGET COMPOUND 10

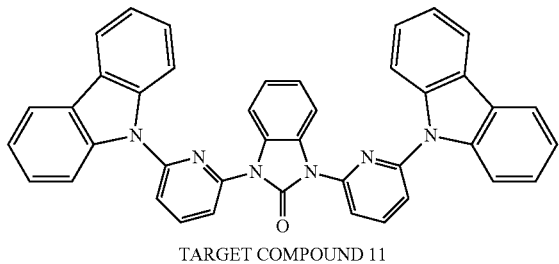

TARGET COMPOUND 11

Under a nitrogen stream, 2-hydroxybenzimidazole (0.724 g), Target Compound 10 (7.50 g), copper(I) iodide (2.06 g), potassium carbonate (2.99 g), and N,N-dimethylformamide (17 mL) were heated to reflux for 10 hours with stirring and then left standing to cool. Methylene chloride and activated clay were added to the reaction mixture. The resulting mixture was stirred. The insoluble matter was filtered off. After the filtrate was concentrated, the resulting precipitate was subjected to suspension washing with methanol, a chloroform/methanol mixture, and chloroform to yield Target Compound 11 (2.27 g).

DEI-MS: m/z=618 (M$^+$)

This compound had a glass transition temperature of 123° C., a melting point of 317° C., and a vaporization temperature of 500° C.

The difference in energy between the excited triplet state and the ground state of this compound was 3.00 eV.

Example 7

Target Compound 12

[Chem. 62]

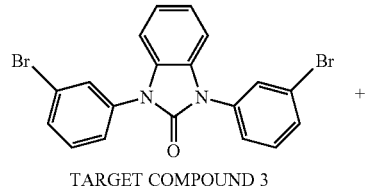

TARGET COMPOUND 3

-continued

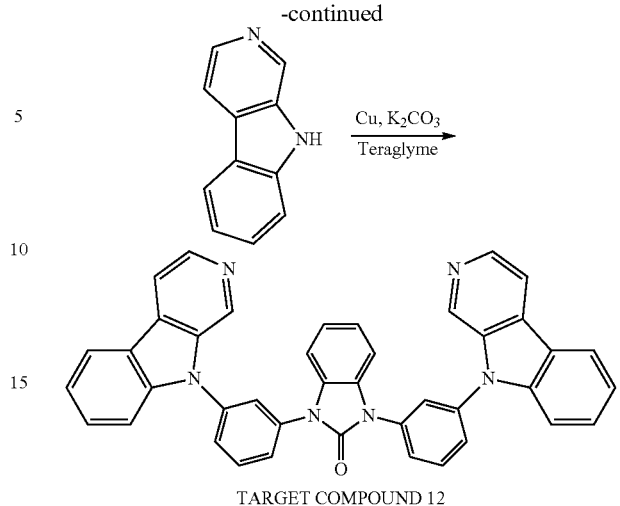

TARGET COMPOUND 12

Under a nitrogen stream, 9H-pyrido[3,4-b]indole (2.8 g), Target Compound 3 (2.47 g), a copper powder (1.06 g), potassium carbonate (4.6 g), and tetraglyme (8 mL) were allowed to react at 180° C. for 8 hours with stirring.

After the completion of the reaction, chloroform was added to the reaction mixture. The insoluble matter was filtered off. After the filtrate was concentrated, the resulting precipitate was subjected to suspension washing with methanol and purified by silica-gel column chromatography (an ethyl acetate/methylene chloride mixture→an ethanol/methylene chloride mixture) to yield Target Compound 12 (1.27 g).

DEI-MS: m/z=617 (M−H)$^+$

DCI-MS: m/z=619 (M+H)$^+$

This compound had a glass transition temperature of 135° C., a melting point of 221° C., and a vaporization temperature of 499° C.

This compound was dissolved in toluene in an amount of 3 percent by weight or more.

The difference in energy between the excited triplet state and the ground state of this compound was 2.96 eV.

Example 8

Target Compounds 13 and 14

[Chem. 63]

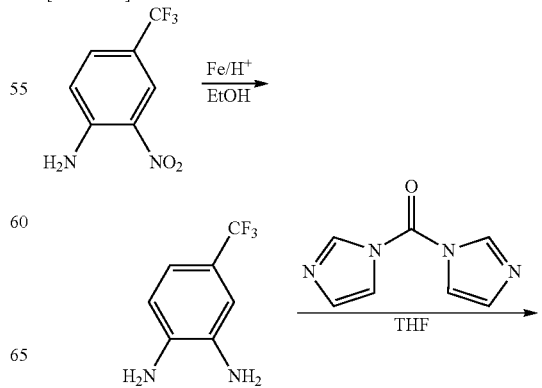

-continued

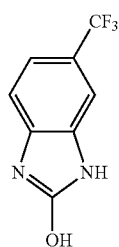

TARGET COMPOUND 13

A concentrated hydrochloric acid solution (120 mL) was added to a suspension of 4-amino-3-nitrobenzene trifluoride (20.06 g) and ethanol (400 mL) in air. The mixture was heated to 80° C. with stirring. After reduced iron (27.09 g) was gradually added thereto over a period of 15 minutes, the mixture was heated to reflux for 1 hour with stirring. After the mixture was cooled on ice, the resulting solution was neutralized with aqueous ammonium hydroxide and then extracted with dichloromethane. The extract was washed with water, concentrated, and purified by silica-gel column chromatography to yield 3,4-diaminobenzene trifluoride (12.495 g).

Under a nitrogen stream, 1,1'-carbonyldiimidazole (3.314 g) was added to a solution of 3,4-diaminobenzene trifluoride (3.0 g) and dry tetrahydrofuran (100 mL) on ice. The mixture was stirred at room temperature for 10.7 hours. After the resulting solution was concentrated, methanol was added thereto. The mixture was irradiated with ultrasound and then concentrated. The resulting precipitate was filtered and purified by suspension washing with an ethanol/hexane mixed solvent and recrystallization in ethyl acetate. Thereby, Target Compound 13 (1.203 g) was obtained.

DEI-MS: m/z=202 (M$^+$)

[Chem. 64]

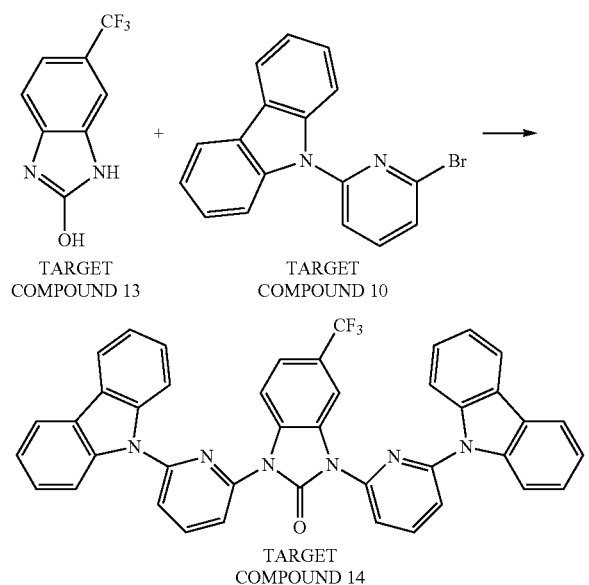

Under a nitrogen stream, a mixed solution of Target Compound 13 (1.188 g), Target Compound 10 (5.125 g), CuI g),
potassium carbonate (3.28 g), and anhydrous N,N-dimethylformamide (19 mL) was heated to reflux for 6.2 hours with stirring. Target Compound 10 (1.41 g), CuI (1.15 g), and potassium carbonate (1.8 g) were then added thereto. The resulting mixture was heated to reflux for 4.5 hours with stirring. After methanol (30 mL) and water (30 mL) were added to the resulting solution, filtration was performed. The residue was added to 150 mL of chloroform. The mixture was stirred. Activated clay was added to the resulting solution. The mixture was stirred and filtered. The filtrate was concentrated and purified by column chromatography with neutral spherical silica gel (eluent: hexane/methylene chloride), suspension washing with methanol, and hot suspension washing with a mixed solvent of ethyl acetate and ethanol. Thereby, Target Compound 14 (2.164 g) was obtained.

DEI-MS: m/z=686 (M$^+$)

This compound had a glass transition temperature of 126° C., a melting point of 282° C., and a vaporization temperature of 399° C.

The difference in energy between the excited triplet state and the ground state of this compound was 2.97 eV.

Example 9

Target Compound 15 and 16

[Chem. 65]

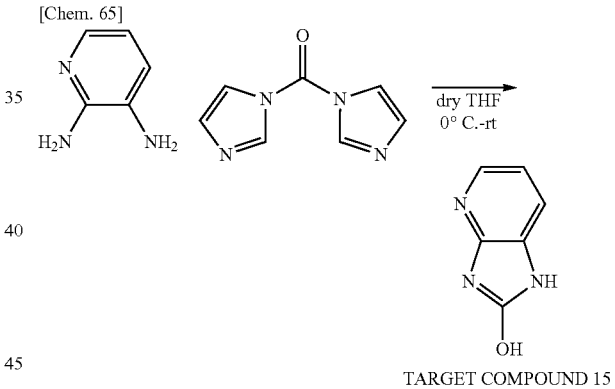

TARGET COMPOUND 15

Under a nitrogen stream, 1,1'-carbonyldiimidazole (15.5 g) was added to a solution of 2,3-diaminopyridine (8.7 g) and dry tetrahydrofuran (500 mL) on ice. The mixture was stirred at room temperature for 14 hours. After the resulting solution was concentrated, methanol was added thereto. The mixture was subjected to hot suspension washing. The resulting precipitate was filtered to obtain Target Compound 15 (4.9 g).

DEI-MS: m/z=135 (M$^+$)

[Chem. 66]

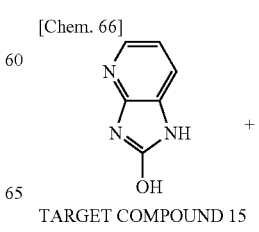

TARGET COMPOUND 15

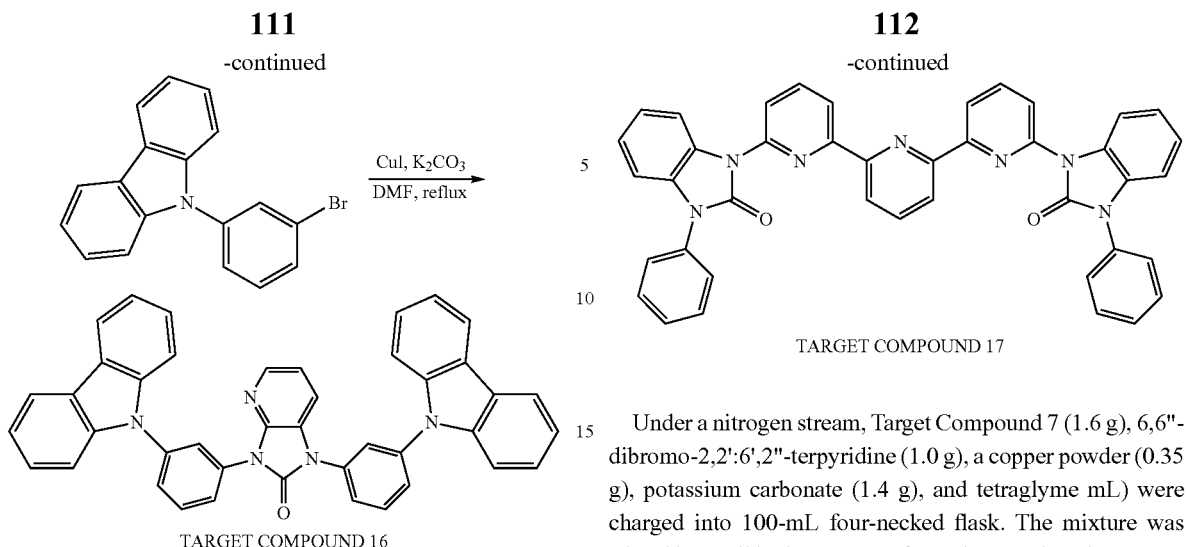

TARGET COMPOUND 16

Under a nitrogen stream, a mixed solution of Target Compound 15 (1.0 g), N-(3-bromophenyl)carbazole (6.8 g), CuI g), potassium carbonate (4.2 g), and anhydrous N,N-dimethylformamide (10 mL) was heated to reflux for 6.2 hours with stirring. Target Compound 10 (1.4 g), CuI (1.15 g), and potassium carbonate (1.8 g) were then added thereto. The resulting mixture was heated to reflux for 15 hours with stirring. The reaction mixture was diluted with dichloromethane, filtered, washed with brain and 1 N hydrochloric acid, and dried over sodium sulfate. Brown oil obtained by vacuum concentration was purified by silica-gel column chromatography (eluent: toluene) and then suspension washing with methanol to yield Target Compound 16 (1.1 g).

DEI-MS: m/z=617 (M+)

This compound had a glass transition temperature of 125° C., a melting point of 226° C., and a vaporization temperature of 490° C.

This compound was dissolved in toluene in an amount of 3 percent by weight or more.

The difference in energy between the excited triplet state and the ground state of this compound was 2.99 eV.

Example 10

Target Compound 17

[Chem. 67]

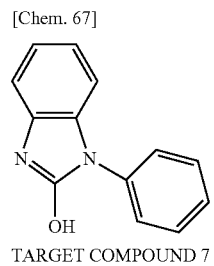

TARGET COMPOUND 7

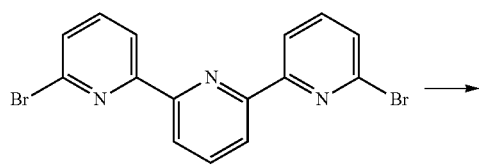

TARGET COMPOUND 17

Under a nitrogen stream, Target Compound 7 (1.6 g), 6,6"-dibromo-2,2':6',2"-terpyridine (1.0 g), a copper powder (0.35 g), potassium carbonate (1.4 g), and tetraglyme mL) were charged into 100-mL four-necked flask. The mixture was stirred in an oil bath at 170° C. for 13 hours. The mixture was diluted with dichloromethane and filtered. The solvent was evaporated under reduced pressure to provide a yellowish-white solid. The solid was subjected to hot suspension washing with tetrahydrofuran to yield a white powder of Target Compound 17 (0.9 g).

DEI-MS: m/z=649 (M+)

This compound had a glass transition temperature of 118° C., a melting point of 276° C., and a vaporization temperature of 451° C.

The difference in energy between the excited triplet state and the ground state of this compound was 2.98 eV.

[Production Example of Organic Electroluminescent Device of the Invention]

Examples of the production of an organic electroluminescent device of the present invention will be described below.

Example 11

An organic electroluminescent device having a structure shown in FIG. 7 was produced by the following procedure.

A 150-nm-thick transparent conductive film 2 composed of indium-tin oxide (ITO) formed on the glass substrate 1 (the film being formed by sputtering, sheet resistance: 15Ω) was patterned into a strip having a width of 2 mm by common photolithography techniques and etching with hydrochloric acid, forming the anode 2. The ITO substrate having the pattern was subjected to ultrasonic cleaning with acetone, washing with deionized water, and ultrasonic cleaning with isopropyl alcohol. The substrate was dried by nitrogen blowing. Finally, ultraviolet-ozone cleaning was performed.

A non-conjugated aromatic amino group-containing polymer compound (PB-2) of a structural formula shown below, together with an electron-accepting compound (A-2) of a structural formula shown below, as materials for the hole-injection layer 3 was spin-coated under conditions described below.

[Chem. 68]

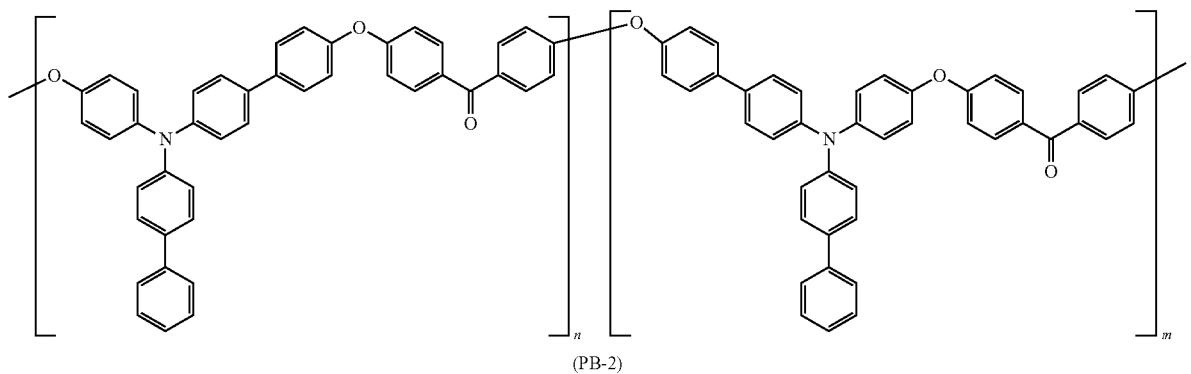

(PB-2)

WEIGHT-AVERAGE MOLECULAR WEIGHT: 48,900
NUMBER-AVERAGE MOLECULAR WEIGHT: 11,000

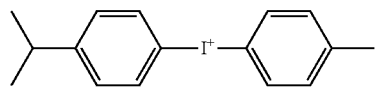

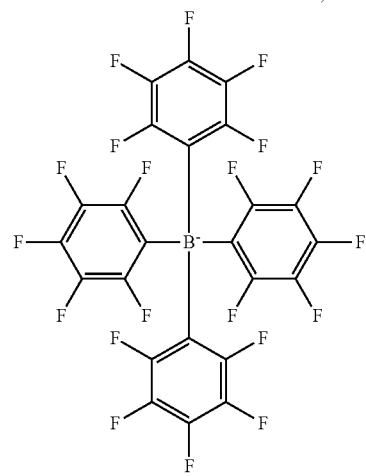

(A-2)

Spin-Coating Conditions

Solvent: anisole

Concentration of PB-2: 2 [wt %]

PB-2:A-2:10:2 (weight ratio)

Number of Revolutions of Spinner: 2,000 [rpm]

Period of Revolutions of Spinner: 30 [s]

Drying Conditions: 230 [° C.], 15 [min]

A uniform thin film having a thickness of 30 nm was formed by spin coating described above.

The substrate having the hole-injection layer 3 was placed in a vacuum evaporation apparatus. Rough evacuation of the apparatus was performed with an oil-sealed rotary pump. Then the apparatus was evacuated with a cryopump until the degree of vacuum in the apparatus reached $9.8 \times 10^{-5}$ Pa (about $7.5 \times 10^{-7}$ Torr) or less. An arylamine compound (H-1) of a structural formula shown below in a ceramic crucible placed in the apparatus was evaporated by heating with a tantalum wire heater arranged around the crucible. The temperature of the crucible was controlled in the range of 300° C. to 314° C. The hole-transport layer 10 having a thickness of 40 nm was formed at a degree of vacuum of $9.0 \times 10^{-5}$ Pa (about $6.9 \times 10^{-7}$ Torr) and an evaporation rate of 0.1 nm/s during evaporation.

[Chem. 69]

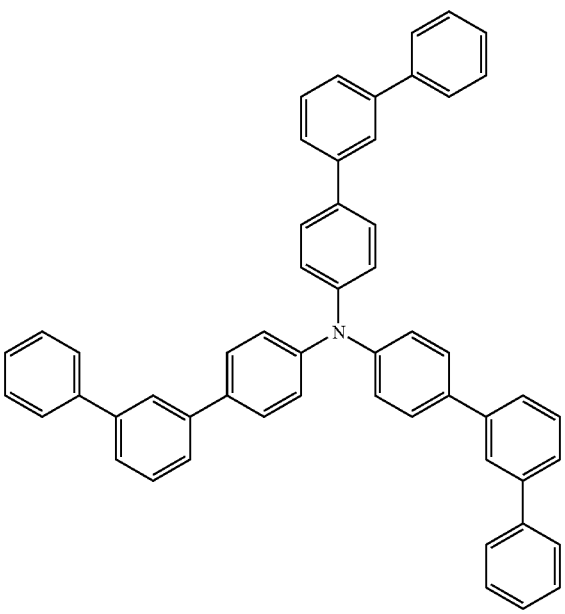

(H-1)

Subsequently, Target Compound 4 prepared in EXAMPLE 2, i.e., an organic compound (EM-1) of the present invention, as a main component (host material) of the light-emitting layer 4 and an organic iridium complex (D-1) of a structural formula shown below as an auxiliary component (dopant) were charged into separate ceramic crucibles. Film formation was performed by simultaneous co-evaporation.

[Chem. 70]

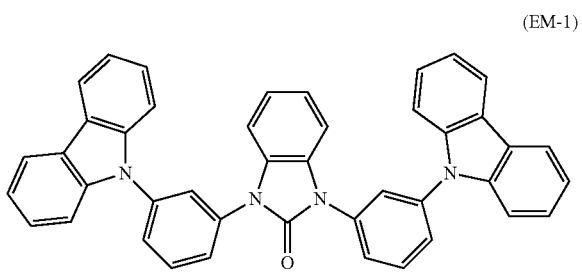

(EM-1)

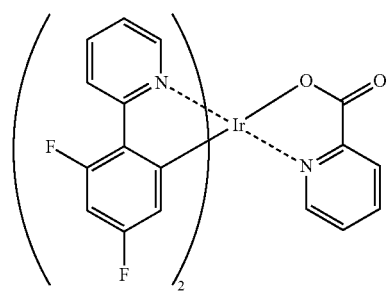

(D-1)

For the organic compound (EM-1) of the present invention, the temperature of the crucible was controlled in the range of 270° C. to 284° C., and the evaporation rate was controlled to 0.1 nm/s. The temperature of the crucible containing the organic iridium complex (D-1) was controlled to 230° C. to 237° C. Thereby, the light-emitting layer 4 having a thickness of 30 nm and containing about 12.5 percent by weight of the organic iridium complex (D-1) was stacked on the hole-transport layer 10. The degree of vacuum was $7.4 \times 10^{-5}$ Pa (about $5.7 \times 10^{-7}$ Torr) during evaporation.

A triarylbenzene derivative (HB-2) of a structural formula shown below was evaporated at a crucible temperature in the range of 343° C. to 350° C. and an evaporation rate of 0.09 nm/s. Thereby, the hole-inhibition layer 8 having a thickness of 10 nm was stacked. The degree of vacuum was $7.1 \times 10^{-5}$ Pa (about $5.5 \times 10^{-7}$ Torr) during evaporation.

[Chem. 71]

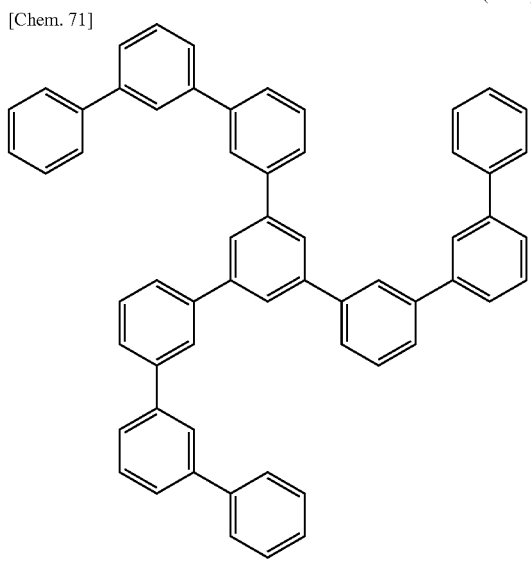

(HB-2)

Next, bathocuproin (ET-2), functioning as the electron-transport layer 7, of a structural formula shown below was similarly evaporated on the hole-inhibition layer 8. In this case, the temperature of the crucible containing bathocuproin (ET-2) was controlled in the range of 160° C. to 172° C. The degree of vacuum was set to $6.6 \times 10^{-5}$ Pa (about $5.1 \times 10^{-7}$ Torr), and the evaporation rate was set to 0.1 nm/s during evaporation. The thickness was set to 30 nm.

[Chem. 72]

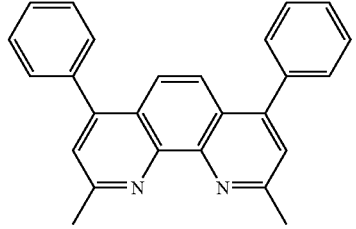

(ET-2)

The substrate temperature was maintained at room temperature when the hole-transport layer 10, the light-emitting layer 4, the hole-inhibition layer 8, and the electron-transport layer 7 were formed by vacuum evaporation.

The device in which evaporation up to the electron-transport layer 7 was finished was removed from the vacuum evaporation apparatus to the atmosphere. A stripe shadow mask, functioning as a mask used for forming a cathode by evaporation, having a width of 2 mm was brought into close contact with the device so as to be orthogonal to the ITO stripe of the anode 2. The device was placed in another vacuum evaporation apparatus. The apparatus was evacuated as in the organic layers until the degree of vacuum in the apparatus reached $2.8 \times 10^{-6}$ Torr (about $3.6 \times 10^{-4}$ Pa) or less. As the cathode 6, first, a lithium fluoride (LiF) film having a thickness of 0.5 nm was formed on the electron-transport layer 7 by evaporation with a molybdenum boat at an evaporation rate of 0.03 nm/s and a degree of vacuum of $2.8 \times 10^{-6}$ Torr (about $3.7 \times 10^{-4}$ Pa). Next, aluminum was similarly heated with a molybdenum boat at an evaporation rate of 0.2 nm/s and a degree of vacuum of $9.8 \times 10^{-6}$ Torr (about $1.3 \times 10^{-3}$ Pa), forming an aluminum film having a thickness of 80 nm. Thereby, the cathode 6 was completed. The substrate temperature was maintained at room temperature during the evaporation of the two-layer cathode 6.

Thereby, an organic electroluminescent device having a 2 mm×2 mm luminescent portion was obtained. Tables 1 and 2 show luminescence properties of the device.

The device emitted blue-green light having a maximum wavelength of 473 nm and a half-width of 67 nm. The luminescence of the device was determined to be attributed to the organic iridium complex (D-1). The CIE chromaticity (x, y) was (0.18, 0.38).

TABLE 1

|  | Voltage (@100 cd/m$^2$) [V] | Luminance/ current (@100 cd/m$^2$) [cd/A] | Luminous efficiency (@100 cd/m$^2$) [lm/W] | Voltage (@1000 cd/m$^2$) [V] | Luminance/ current (@1000 cd/m$^2$) [cd/A] |
| --- | --- | --- | --- | --- | --- |
| EXAMPLE 11 | 4.9 | 30.8 | 20 | 6.1 | 28.7 |
| COMPARATIVE EXAMPLE 1 | 5.4 | 11.5 | 6.7 | 7 | 14.2 |

Example 12

An organic electroluminescent device having the structure shown in FIG. 7 was produced as in EXAMPLE 11, except that the light-emitting layer 4 was formed by a procedure described below.

Target Compound 16 prepared in EXAMPLE 9 as a main component (host material) of the light-emitting layer 4, i.e., an organic compound (EM-3) of the present invention and the organic iridium complex (D-1) used in EXAMPLE 11 as an auxiliary component (dopant) were charged into separate ceramic crucibles. Film formation was performed by simultaneous co-evaporation.

[Chem. 73]

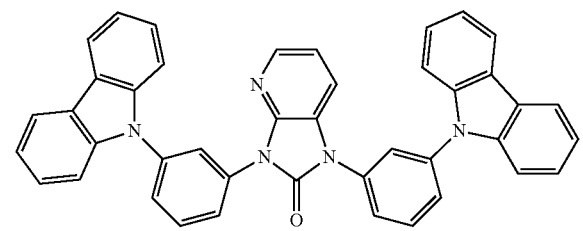

(EM-3)

For the organic compound (EM-3) of the present invention, the temperature of the crucible was controlled in the range of 400° C. to 407° C., and the evaporation rate was controlled to 0.1 nm/s. The temperature of the crucible containing the organic iridium complex (D-1) was controlled to 201° C. to 207° C. Thereby, the light-emitting layer 4 having a thickness of 30 nm and containing about 10.4 percent by weight of the organic iridium complex (D-1) was stacked on the hole-transport layer 10. The degree of vacuum was 4.6×10$^{-5}$ Pa (about 3.5×10$^{-7}$ Torr) during evaporation.

Table 2 shows luminescence properties of the device.

The device emitted blue-green light having a maximum wavelength of 471 nm and a half-width of 53 nm. The luminescence of the device was determined to be attributed to the organic iridium complex (D-1). The CIE chromaticity (x, y) was (0.14, 0.31).

Example 13

An organic electroluminescent device having the structure shown in FIG. 7 was produced as in EXAMPLE 11, except that the light-emitting layer 4 was formed by a procedure described below.

Target Compound 12 prepared in EXAMPLE 7 as a main component (host material) of the light-emitting layer 4, i.e., an organic compound (EM-4) of the present invention and the organic iridium complex (D-1) used in EXAMPLE 11 as an auxiliary component (dopant) were charged into separate ceramic crucibles. Film formation was performed by simultaneous co-evaporation.

[Chem. 74]

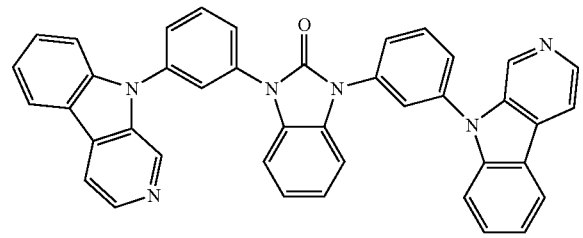

(EM-4)

For the organic compound (EM-4) of the present invention, the temperature of the crucible was controlled in the range of 217° C. to 242° C., and the evaporation rate was controlled to 0.09 nm/s. The temperature of the crucible containing the organic iridium complex (D-1) was controlled to 213° C. to 216° C. Thereby, the light-emitting layer 4 having a thickness of 30 nm and containing about 13.1 percent by weight of the organic iridium complex (D-1) was stacked on the hole-transport layer 10. The degree of vacuum was 5.0×10$^{-5}$ Pa (about 4.0×10$^{-7}$ Torr) during evaporation.

Table 2 shows luminescence properties of the device.

The device emitted blue-green light having a maximum wavelength of 472 nm and a half-width of 53 nm. The luminescence of the device was determined to be attributed to the organic iridium complex (D-1). The CIE chromaticity (x, y) was (0.15, 0.32).

Comparative Example 1

An organic electroluminescent device having the structure shown in FIG. 7 was produced as in EXAMPLE 11, except that the light-emitting layer 4 was formed by a procedure described below.

A carbazole derivative (CBP) of a structural formula shown below as a main component (host material) of the light-emitting layer 4 and the organic iridium complex (D-1) used in EXAMPLE 11 as an auxiliary component (dopant) were charged into separate ceramic crucibles. Film formation was performed by simultaneous co-evaporation.

[Chem. 75]

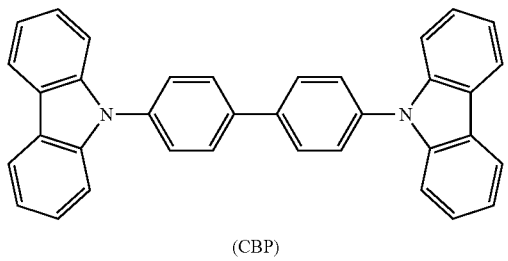

(CBP)

For the carbazole derivative (CBP), the temperature of the crucible was controlled in the range of 411° C. to 406° C., and the evaporation rate was controlled to 0.08 nm/s. The temperature of the crucible containing the organic iridium complex (D-1) was controlled to 204° C. to 209° C. Thereby, the light-emitting layer 4 having a thickness of 30 nm and containing about 13.1 percent by weight of the organic iridium complex (D-1) was stacked on the hole-transport layer 10. The degree of vacuum was $3.8 \times 10^{-5}$ Pa (about $2.9 \times 10^{-7}$ Torr) during evaporation.

Tables 1 and 2 show luminescence properties of the device.

The device emitted blue-green light having a maximum wavelength of 490 nm and a half-width of 59 nm. In addition to the luminescence attributed to the organic iridium complex (D-1), luminescence attributed to another material was also observed. The CIE chromaticity (x, y) was (0.19, 0.54).

TABLE 2

|  | Luminance/ current (@100 cd/m$^2$) [cd/A] | Luminous efficiency (@100 cd/m$^2$) [lm/W] | Luminance/ current (@2500 cd/m$^2$) [cd/A] |
| --- | --- | --- | --- |
| EXAMPLE 11 | 30.8 | 20 | 26.1 |
| EXAMPLE 12 | 0.8 | 0.2 | 2.3 |
| EXAMPLE 13 | 18.3 | 9.6 | 16.8 |
| EXAMPLE 14 | 22.8 | 11.7 | 20.8 |
| COMPARATIVE EXAMPLE 1 | 11.5 | 6.7 | 13.8 |

Example 14

An organic electroluminescent device having the structure shown in FIG. 7 was produced by the following procedure.

A 150-nm-thick transparent conductive film 2 composed of indium-tin oxide (ITO) formed on the glass substrate 1 (the film being formed by sputtering, sheet resistance: 15Ω) was patterned into a strip having a width of 2 mm by common photolithography techniques and etching with hydrochloric acid, forming the anode 2. The ITO substrate having the pattern was subjected to ultrasonic cleaning with acetone, washing with deionized water, and ultrasonic cleaning with isopropyl alcohol. The substrate was dried by nitrogen blowing. Finally, ultraviolet-ozone cleaning was performed.

A non-conjugated aromatic amino group-containing polymer compound (PB-1) (weight-average molecular weight: 29,400, number-average molecular weight: 12,600) of a structural formula shown below, together with the electron-accepting compound (A-2) used in EXAMPLE 11, as materials for the hole-injection layer 3 was spin-coated under conditions described below.

[Chem. 76]

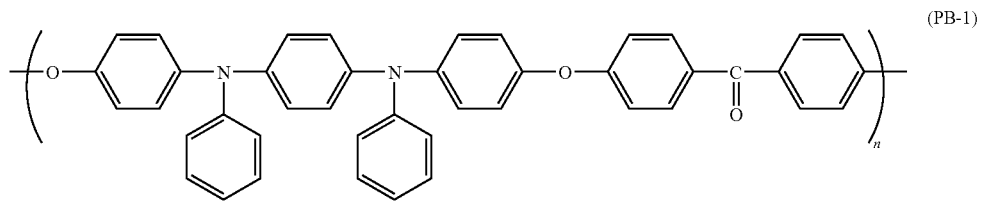

(PB-1)

Spin-Coating Conditions

Solvent: Ethyl benzoate

Concentration of PB-1: 2 [wt %]

PB-1:A-2: 10:2 (weight ratio)

Number of Revolutions of Spinner: 1,500 [rpm]

Period of Revolutions of Spinner: 30 [s]

Drying Conditions: 230 [° C.], 15 [min]

A uniform thin film having a thickness of 30 nm was formed by spin coating described above.

The substrate having the hole-injection layer 3 was placed in a vacuum evaporation apparatus. Rough evacuation of the apparatus was performed with an oil-sealed rotary pump. Then the apparatus was evacuated with a cryopump until the degree of vacuum in the apparatus reached $9.0 \times 10^{-5}$ Pa (about $6.8 \times 10^{-7}$ Torr) or less. The arylamine compound (H-1) used in EXAMPLE 11 in a ceramic crucible placed in the apparatus was evaporated by heating with a tantalum wire heater arranged around the crucible. The temperature of the crucible was controlled in the range of 300° C. to 314° C. The hole-transport layer 10 having a thickness of 40 nm was formed at a degree of vacuum of 9.3×Pa (about $7.0 \times 10^{-7}$ Torr) and an evaporation rate of 0.1 nm/s during evaporation.

Subsequently, Target Compound 4 prepared in EXAMPLE 2, i.e., an organic compound (EM-1) of the present invention, as a main component (host material) of the light-emitting layer 4 and an organic iridium complex (D-2) of a structural formula shown below as an auxiliary component (dopant) were charged into separate ceramic crucibles. Film formation was performed by simultaneous co-evaporation.

[Chem. 77]

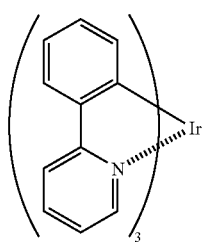
(D-2)

For the organic compound (EM-1) of the present invention, the temperature of the crucible was controlled in the range of 270° C. to 284° C., and the evaporation rate was controlled to 0.1 nm/s. The temperature of the crucible containing the organic iridium complex (D-2) was controlled to 245° C. to 246° C. Thereby, the light-emitting layer 4 having a thickness of 30 nm and containing about 5.9 percent by weight of the organic iridium complex (D-2) was stacked on the hole-transport layer 10. The degree of vacuum was $7.8 \times 10^{-5}$ Pa (about $5.9 \times 10^{-7}$ Torr) during evaporation.

A phenylpyridine derivative (HB-1) of a structural formula shown below was evaporated at a crucible temperature in the range of 343° C. to 350° C. and an evaporation rate of nm/s. Thereby, the hole-inhibition layer 8 having a thickness of 10 nm was stacked. The degree of vacuum was $7.1 \times 10^{-5}$ Pa (about $5.5 \times 10^{-7}$ Torr) during evaporation.

[Chem. 78]

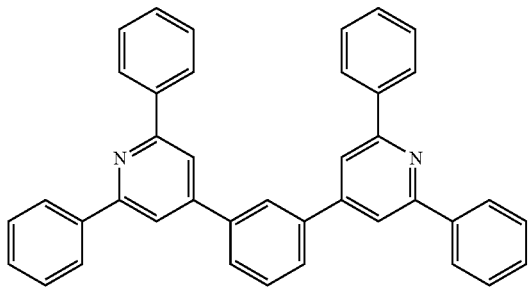
(HB-1)

Next, tris(8-hydroxyquinolinato)aluminum (Alq3), functioning as the electron-transport layer 7, of a structural formula shown below was similarly evaporated on the hole-inhibition layer 8. The temperature of the crucible containing tris(8-hydroxyquinolinato)aluminum (Alq3) was controlled in the range of 296° C. to 300° C. The degree of vacuum was set to $6.6 \times 10^{-5}$ Pa (about $5.1 \times 10^{-7}$ Torr), and the evaporation rate was set to 0.15 m/s during evaporation. The thickness was set to 30 nm.

[Chem. 79]

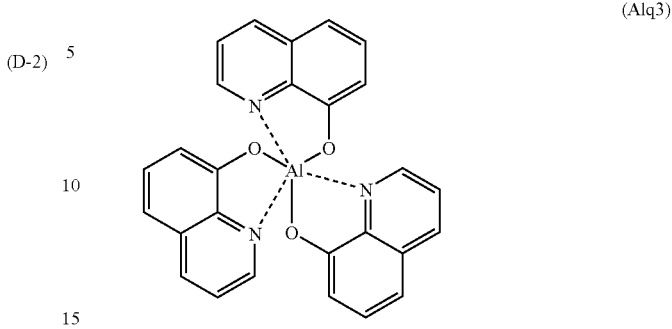
(Alq3)

The substrate temperature was maintained at room temperature when the hole-transport layer 10, the light-emitting layer 4, the hole-inhibition layer 8, and the electron-transport layer 7 were formed by vacuum evaporation.

Then the two-layer cathode 6 was formed by evaporation as in EXAMPLE 11.

Table 3 shows luminescence properties of the device.

The device emitted green light having a maximum wavelength of 514 nm and a half-width of 70 nm. The luminescence of the device was determined to be attributed to the organic iridium complex (D-2). The CIE chromaticity (x, y) was (0.31, 0.62).

Example 15

An organic electroluminescent device having the structure shown in FIG. 7 was produced as in EXAMPLE 14, except that the light-emitting layer 4 was formed by a procedure described below.

Target Compound 11 prepared in EXAMPLE 6 as a main component (host material) of the light-emitting layer 4, i.e., an organic compound (EM-5) of the present invention, and the organic iridium complex (D-2) used in EXAMPLE 14 as an auxiliary component (dopant) were charged into separate ceramic crucibles. Film formation was performed by simultaneous co-evaporation.

[Chem. 80]

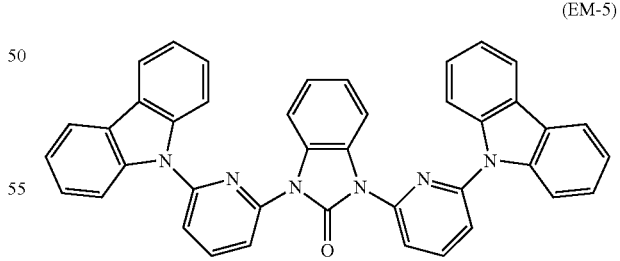
(EM-5)

The evaporation rate of the organic compound (EM-5) of the present invention was controlled to 0.1 nm/s. The temperature of the crucible containing the organic iridium complex (D-2) was controlled to 257° C. to 255° C. Thereby, the light-emitting layer 4 having a thickness of 32 nm and containing about 6.2 percent by weight of the organic iridium complex (D-2) was stacked on the hole-transport layer 10. The degree of vacuum was $1.5 \times 10^{-4}$ Pa during evaporation.

Table 3 shows luminescence properties of the device.

The device emitted green light having a maximum wavelength of 513 nm and a half-width of 68 nm. The luminescence of the device was determined to be attributed to the organic iridium complex (D-2). The CIE chromaticity (x, y) was (0.30, 0.62).

Example 16

An organic electroluminescent device having the structure shown in FIG. 7 was produced as in EXAMPLE 14, except that the hole-transport layer 10 and the light-emitting layer 4 were formed by a procedure described below.

The substrate having the hole-injection layer 3 was placed in a vacuum evaporation apparatus. Rough evacuation of the apparatus was performed with an oil-sealed rotary pump. Then the apparatus was evacuated with a cryopump until the degree of vacuum in the apparatus reached $5.3 \times 10^{-5}$ Pa (about $4.0 \times 10^{-7}$ Torr) or less. An arylamine compound (PPD) of a structural formula shown below in a ceramic crucible placed in the apparatus was evaporated by heating with a tantalum wire heater arranged around the crucible. The temperature of the crucible was controlled in the range of 260° C. to 272° C. The hole-transport layer 10 having a thickness of 40 nm was formed at a degree of vacuum of $6.0 \times 10^{-5}$ Pa (about $4.9 \times 10^{-7}$ Torr) and an evaporation rate of 0.1 nm/s during evaporation.

[Chem. 81]

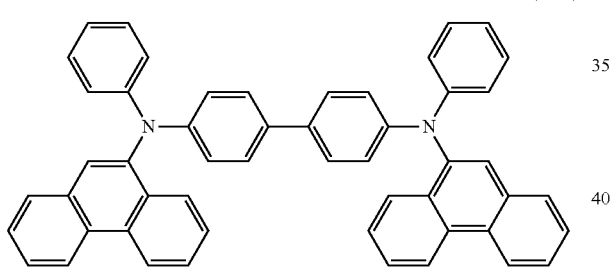

(PPD)

Subsequently, Target Compound 2 prepared in EXAMPLE 1, i.e., an organic compound (EM-6) of the present invention, as a main component (host material) of the light-emitting layer 4 and the organic iridium complex (D-2) used in EXAMPLE 14 as an auxiliary component (dopant) were charged into separate ceramic crucibles. Film formation was performed by simultaneous co-evaporation.

[Chem. 82]

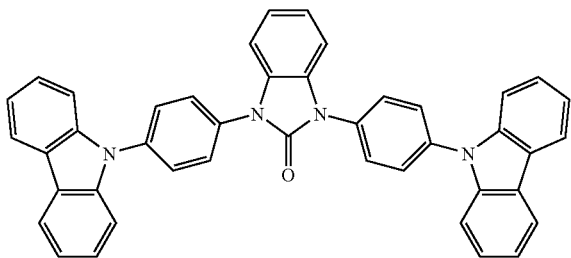

(EM-6)

The evaporation rate of the organic compound (EM-6) of the present invention was controlled to 0.1 nm/s. The temperature of the crucible containing the organic iridium complex (D-2) was controlled to 268° C. to 270° C. Thereby, the light-emitting layer 4 having a thickness of 30 nm and containing about 6.1 percent by weight of the organic iridium complex (D-2) was stacked on the hole-transport layer 10. The degree of vacuum was $6.3 \times 10^{-5}$ Pa (about $4.7 \times 10^{-7}$ Torr) during evaporation.

Table 3 shows luminescence properties of the device.

The device emitted green light having a maximum wavelength of 513 nm and a half-width of 69 nm. The luminescence of the device was determined to be attributed to the organic iridium complex (D-2). The CIE chromaticity (x, y) was (0.30, 0.58).

Comparative Example 2

An organic electroluminescent device having the structure shown in FIG. 7 was produced as in EXAMPLE 14, except that the light-emitting layer 4 was formed by a procedure described below.

A carbazole derivative (SiMCP) of a structural formula shown below as a main component (host material) of the light-emitting layer 4 and the organic iridium complex (D-2) used in EXAMPLE 14 as an auxiliary component (dopant) were charged into separate ceramic crucibles. Film formation was performed by simultaneous co-evaporation.

[Chem. 83]

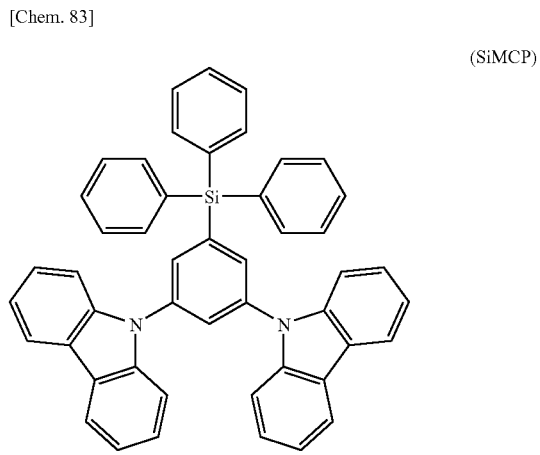

(SiMCP)

The evaporation rate of the carbazole derivative (SiMCP) was controlled to 0.1 nm/s. The temperature of the crucible containing the organic iridium complex (D-2) was controlled to 268° C. to 270° C. Thereby, the light-emitting layer 4 having a thickness of 30 nm and containing about 5.9 percent by weight of the organic iridium complex (D-2) was stacked on the hole-transport layer 10. The degree of vacuum was $6.3 \times 10^{-5}$ Pa (about $4.7 \times 10^{-7}$ Torr) during evaporation.

Table 3 shows luminescence properties of the device.

The device emitted green light having a maximum wavelength of 513 nm and a half-width of 70 nm. The luminescence of the device was determined to be attributed to the organic iridium complex (D-2). The CIE chromaticity (x, y) was (0.30, 0.68).

TABLE 3

| | Luminance/ current (@100 cd/m$^2$) [cd/A] | Luminous efficiency (@100 cd/m$^2$) [lm/W] | Luminance/ current (@2500 cd/m$^2$) [cd/A] |
|---|---|---|---|
| EXAMPLE 14 | 37.4 | 22.2 | 30.1 |
| EXAMPLE 15 | 33.2 | 14.7 | 27.5 |
| EXAMPLE 16 | 21.5 | 13.8 | 15 |
| COMPARATIVE EXAMPLE 2 | 30.1 | 20.9 | 18.5 |

Example 17 and Comparative Example 3

In each of the devices produced in EXAMPLES 14 to 16 and COMPARATIVE EXAMPLE 2, a change in luminance when a direct current equivalent to a current density of 250 mA/cm$^2$ passed therethrough was observed. Table 4 shows luminance seconds after the energization, luminance immediately after the energization, and a value obtained by dividing the luminance value 40 seconds after the energization by the luminance value immediately after the energization.

TABLE 4

| | Luminance immediately after energization [cd/m$^2$] | Luminance 40 seconds after energization [cd/m$^2$] | Value obtained by dividing luminance value 40 seconds after energization by luminance value immediately after energization |
|---|---|---|---|
| Element in EXAMPLE 14 | 46300 | 44840 | 0.97 |
| Element in EXAMPLE 15 | 51716 | 52009 | 1.01 |
| Element in EXAMPLE 16 | 24020 | 22390 | 0.93 |
| Element in COMPARATIVE EXAMPLE 2 | 23010 | 19980 | 0.87 |

The results demonstrated that each of the devices including the compounds (EM-1), (EM-5), and (EM-6) of the present invention as the main components of the light-emitting layers exhibited a low reduction in luminance upon energization compared with the device including the carbazole derivative (SiMCP) as the main component of the light-emitting layer.

Example 18

An organic electroluminescent device having the structure shown in FIG. 7 was produced as in EXAMPLE 14, except that the hole-transport layer 10 and the light-emitting layer 4 were formed by a procedure described below.

The substrate having the hole-injection layer 3 was placed in a vacuum evaporation apparatus. Rough evacuation of the apparatus was performed with an oil-sealed rotary pump. Then the apparatus was evacuated with a cryopump until the degree of vacuum in the apparatus reached 7.5×10$^{-5}$ Pa (about 5.6×10$^{-7}$ Torr) or less. Target Compound 5 prepared in EXAMPLE 3, i.e., an organic compound (EM-7) of the present invention, in a ceramic crucible placed in the apparatus was evaporated by heating with a tantalum wire heater arranged around the crucible. The hole-transport layer 10 having a thickness of 40 nm was formed at a degree of vacuum of 7.0×10$^{-5}$ Pa and an evaporation rate of 0.1 nm/s during evaporation.

[Chem. 84]

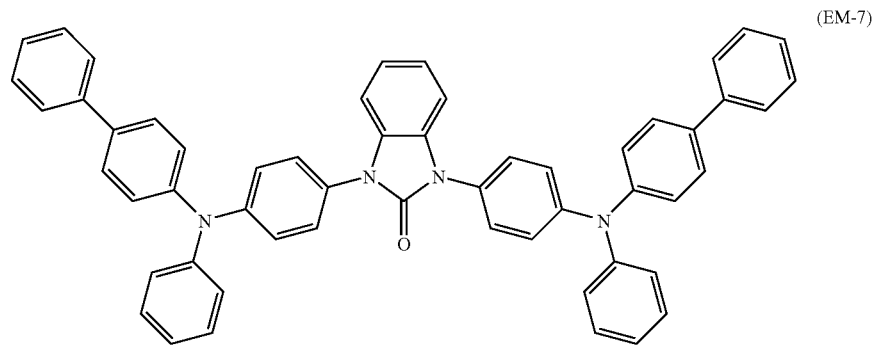

(EM-7)

Subsequently, a carbazole derivative (E-1) shown below as a main component (host material) of the light-emitting layer 4 and the organic iridium complex (D-2) used in EXAMPLE 14 as an auxiliary component (dopant) were charged into separate ceramic crucibles. Film formation was performed by simultaneous co-evaporation.

[Chem. 85]

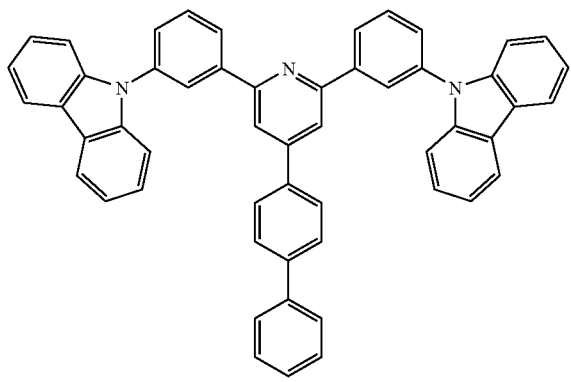

(E-1)

For the carbazole derivative (E-1), the temperature of the crucible was controlled to 300° C. to 304° C., and the evaporation rate was controlled to 0.08 nm/s. The temperature of the crucible containing the organic iridium complex (D-2) was controlled to 239° C. to 242° C. Thereby, the light-emitting layer 4 having a thickness of 30 nm and containing 6.4 percent by weight of the organic iridium complex (D-2) was stacked on the hole-transport layer 10. The degree of vacuum was $6.6 \times 10^{-5}$ Pa during evaporation.

Table 5 shows luminescence properties of the device.

The device emitted green light having a maximum wavelength of 513 nm and a half-width of 69 nm. The luminescence of the device was determined to be attributed to the organic iridium complex (D-2). The CIE chromaticity (x, y) was (0.31, 0.62).

Comparative Example 4

An organic electroluminescent device having the structure shown in FIG. 7 was produced as in EXAMPLE 18, except that the hole-transport layer 10 was formed by a procedure described below.

An arylamine compound (PPD) of a structural formula shown below was charged into a ceramic crucible and evaporated by heating with a tantalum wire heater arranged around the crucible. The degree of vacuum was controlled to $6.0 \times 10^{-5}$ Pa, and the evaporation rate was controlled to 0.08 to 0.13 nm/s during evaporation. Thereby, the hole-transport layer 10 having a thickness of 40 nm was obtained.

[Chem. 86]

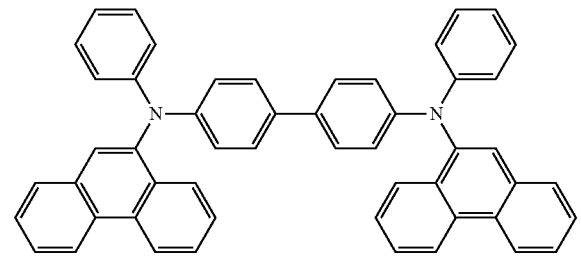

(PPD)

Table 5 shows luminescence properties of the device.

The device emitted green light having a maximum wavelength of 513 nm and a half-width of 67 nm. The luminescence of the device was determined to be attributed to the organic iridium complex (D-2). The CIE chromaticity (x, y) was (0.30, 0.61).

TABLE 5

| | Luminance/ current (@100 cd/m²) [cd/A] | Luminous efficiency (@100 cd/m²) [lm/W] | Luminance/ current (@2500 cd/m²) [cd/A] |
|---|---|---|---|
| EXAMPLE 18 | 50.6 | 28.1 | 48.7 |
| COMPARATIVE EXAMPLE 4 | 36.3 | 23 | 26.7 |

Example 19

An organic electroluminescent device having a structure shown in FIG. 7 was produced by the following procedure.

The hole-injection layer 3 and the hole-transport layer 10 were formed as in EXAMPLE 14. Target Compound 4 prepared in EXAMPLE 2, i.e., the organic compound (EM-1) of the present invention, as a main component (host material) of the light-emitting layer 4 and an organic iridium complex (facial configuration, D-3, wherein Me represents a methyl group) as an auxiliary component (dopant) were charged into separate ceramic crucibles. Film formation was performed by simultaneous co-evaporation.

[Chem. 87]

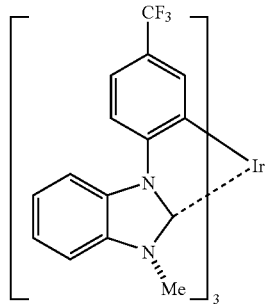

(D-3)

For the organic compound (EM-1) of the present invention, the temperature of the crucible was controlled in the range of 277° C. to 283° C., and the evaporation rate was controlled to 0.07 nm/s. The temperature of the crucible containing the organic iridium complex (D-3) was controlled to 279° C. to 281° C. Thereby, the light-emitting layer 4 having a thickness of 30 nm and containing about 5.8 percent by weight of the organic iridium complex (D-3) was stacked on the hole-transport layer 10. The degree of vacuum was $5.0 \times 10^{-5}$ Pa (about $3.8 \times 10^{-7}$ Torr) during evaporation.

Only the organic compound (EM-1) was evaporated at a crucible temperature in the range of 283° C. to 297° C. and an evaporation rate of 0.09 nm/s. Thereby, the hole-inhibition layer 8 having a thickness of 10 nm was stacked. The degree of vacuum was $4.5 \times 10^{-5}$ Pa (about $3.4 \times 10^{-7}$ Torr) during evaporation.

Next, bathocuproin (ET-2) used in EXAMPLE 11, functioning as the electron-transport layer 7, was similarly evaporated on the hole-inhibition layer 8. In this case, the temperature of the crucible containing bathocuproin (ET-2) was controlled in the range of 162° C. to 183° C. The degree of vacuum was set to $4.4 \times 10^{-5}$ Pa (about $3.3 \times 10^{-7}$ Torr), and the evaporation rate was set to 0.09 nm/s during evaporation. The thickness was set to 30 nm.

The substrate temperature was maintained at room temperature when the hole-transport layer 10, the light-emitting layer 4, the hole-inhibition layer 8, and the electron-transport layer 7 were formed by vacuum evaporation.

Then the two-layer cathode 6 was formed by evaporation as in EXAMPLE 11.

Table 6 shows luminescence properties of the device.

The device emitted blue light having a maximum wavelength of 403 nm. The luminescence of the device was determined to be attributed to the organic iridium complex (D-3). The CIE chromaticity (x, y) was (0.18, 0.10).

TABLE 6

|  | Voltage (@100 cd/m$^2$) [V] | Luminance/ current (@100 cd/m$^2$) [cd/A] |
|---|---|---|
| EXAMPLE 19 | 11.3 | 0.1 |

Example 20

An organic electroluminescent device having a structure shown in FIG. 7 was produced by the following procedure.

The hole-injection layer 3 and the hole-transport layer 10 were formed as in EXAMPLE 14. Target Compound 11 prepared in EXAMPLE 6, i.e., the organic compound (EM-5) of the present invention, as a main component (host material) of the light-emitting layer 4 and the organic iridium complex (D-1) used in EXAMPLE 11 as an auxiliary component (dopant) were charged into separate ceramic crucibles. Film formation was performed by simultaneous co-evaporation.

The evaporation rate of the organic compound (EM-5) of the present invention was controlled to 0.1 nm/s. The temperature of the crucible containing the organic iridium complex (D-1) was controlled to 252° C. to 260° C. Thereby, the light-emitting layer 4 having a thickness of 33 nm and containing about 7.6 percent by weight of the organic iridium complex (D-1) was stacked on the hole-transport layer 10. The degree of vacuum was $4.2 \times 10^{-5}$ Pa during evaporation.

The phenylpyridine derivative (HB-1) used in EXAMPLE 14 was evaporated at a crucible temperature in the range of 340° C. to 341° C. and an evaporation rate of 0.08 to 0.09 nm/s. Thereby, the hole-inhibition layer 8 having a thickness of 5 nm was stacked. The degree of vacuum was $4.6 \times 10^{-5}$ Pa during evaporation.

Next, bis(2-methyl-8-hydroxyquinolinato)(p-phenylphenolato)aluminum (BAlq) of a structural formula shown below, functioning as the electron-transport layer 7, was similarly evaporated on the hole-inhibition layer 8. In this case, the temperature of the crucible containing bis(2-methyl-8-hydroxyquinolinato)(p-phenylphenolato)aluminum (BAlq) was controlled in the range of 190° C. to 191° C. The degree of vacuum was set to $5.1 \times 10^{-5}$ Pa, and the evaporation rate was set to 0.08 to 0.24 m/s during evaporation. The thickness was set to 30 nm.

[Chem. 88]

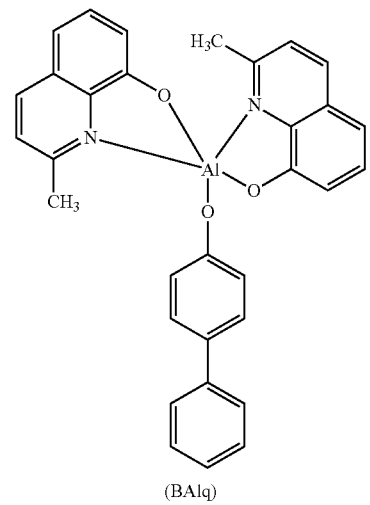

(BAlq)

The substrate temperature was maintained at room temperature when the hole-transport layer 10, the light-emitting layer 4, the hole-inhibition layer 8, and the electron-transport layer 7 were formed by vacuum evaporation.

Then the two-layer cathode 6 was formed by evaporation as in EXAMPLE 11.

Table 7 shows luminescence properties of the device.

The device emitted blue-green light having a maximum wavelength of 471 nm and a half-width of 66 nm. The luminescence of the device was determined to be attributed to the organic iridium complex (D-1). The CIE chromaticity (x, y) was (0.17, 0.36).

TABLE 7

|  | Voltage (@100 cd/m$^2$) [V] | Luminance/ current (@100 cd/m$^2$) [cd/A] | Luminous efficiency (@100 cd/m$^2$) [lm/W] | Voltage (@2500 cd/m$^2$) [V] | Luminance/ current (@2500 cd/m$^2$) [cd/A] |
|---|---|---|---|---|---|
| EXAMPLE 20 | 10.4 | 15.1 | 4.6 | 14.1 | 13.1 |

Example 21

An organic electroluminescent device having a structure shown in FIG. 3 (not including the electron-injection layer) was produced by the following procedure.

A 150-nm-thick transparent conductive film 2 composed of indium-tin oxide (ITO) formed on the glass substrate 1 (the film being formed by sputtering, sheet resistance: 15Ω) was patterned into a strip having a width of 2 mm by common photolithography techniques and etching with hydrochloric acid, forming the anode 2. The ITO substrate having the pattern was subjected to ultrasonic cleaning with acetone, washing with deionized water, and ultrasonic cleaning with isopropyl alcohol. The substrate was dried by nitrogen blowing. Finally, ultraviolet-ozone cleaning was performed.

The hole-injection layer 3 was formed as in EXAMPLE 11, except that the drying conditions in spin coating were set to 230° C. for 180 minutes.

Subsequently, the light-emitting layer 4 was formed on the hole-injection layer 3 by a wet film-forming method described below. As materials for forming the light-emitting layer 4, Target Compound 4 prepared in EXAMPLE 2, i.e., the organic compound (EM-1) of the present invention, and the organic iridium complex (D-1) used in EXAMPLE 11 were used. These were dissolved in toluene as a solvent to prepare an organic-electroluminescent-device composition. The organic-electroluminescent-device composition was spin-coated under conditions described below.

Spin-Coating Conditions

Solvent: toluene

Concentration of EM-1: 2 [wt %]

EM-1:D-1: 10:1 (weight ratio)

Number of Revolutions of Spinner: 1,500 [rpm]

Period of Revolutions of Spinner: 60 [s]

Drying Conditions: 100 [° C.], 60 [min] (under reduced pressure)

A uniform thin film having a thickness of 65 nm was formed by spin coating described above.

The hole-inhibition layer 8, the electron-transport layer 7, and the cathode 6 were formed as in EXAMPLE 11.

Thereby, an organic electroluminescent device having a 2 mm×2 mm luminescent portion was obtained. Table 8 shows luminescence properties of the device.

The device emitted blue-green light having a maximum wavelength of 471 nm and a half-width of 67 nm. The luminescence of the device was determined to be attributed to the organic iridium complex (D-1). The CIE chromaticity (x, y) was (0.18, 0.36).

TABLE 8

| | Voltage (@100 cd/m$^2$) [V] | Luminance/ current (@100 cd/m$^2$) [cd/A] | Luminous efficiency (@100 cd/m$^2$) [lm/W] | Voltage (@1000 cd/m$^2$) [V] | Luminance/ current (@1000 cd/m$^2$) [cd/A] |
|---|---|---|---|---|---|
| EXAMPLE 21 | 8.4 | 29.3 | 11 | 11.3 | 27.7 |

While the present invention has been described in detail by specific embodiments, it will be obvious to those skilled in the art that various changes may be made without departing from the contemplation and the scope of the invention.

The present invention contains subject matter related to Japanese Patent Application (JP 2005-346164) filed in the Japanese Patent Office on Nov. 30, 2005, the entire contents of which are incorporated herein by reference.

The invention claimed is:

1. An organic compound represented by Formula (I):

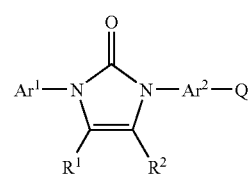

(I)

wherein $Ar^1$ represents an optionally-substituted aromatic hydrocarbon group, an optionally-substituted aromatic heterocyclic group, or an optionally-substituted alkyl group, $Ar^2$ represents an optionally-substituted aromatic hydrocarbon group or an optionally-substituted aromatic heterocyclic group, $R^1$ and $R^2$ each independently represent a substituent that is not hydrogen, or $R^1$ and $R^2$ may be bonded to each other to form a ring, and Q is represented by Formula (I-1):

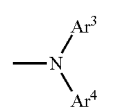

(I-1)

wherein $Ar^3$ to and $Ar^4$ each independently represent an optionally-substituted aromatic hydrocarbon group or an optionally-substituted aromatic heterocyclic group, $Ar^3$ and $Ar^4$ may be bonded to each other to form a ring, wherein one of the following conditions apply:

the organic compound comprises an N-carbazolyl group represented by Formula (I-3) as a partial structure:

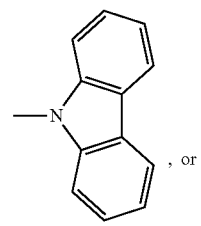

(I-3)

, or $R^1$ and $R^2$ are independently an optionally-substituted alkyl group, or $R^1$ and $R^2$ are bonded to each other to form a ring.

2. An organic compound represented by Formula (II):

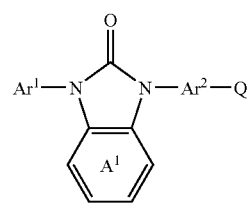

(II)

wherein Ar¹, Ar², and Q are as follows:

Ar¹ represents an optionally-substituted aromatic hydrocarbon group, an optionally-substituted aromatic heterocyclic group, or an optionally-substituted alkyl group, Ar² represents an optionally-substituted aromatic hydrocarbon group or an optionally-substituted aromatic heterocyclic group, and Q is represented by Formula (I-1):

(I-1)

wherein Ar³ and Ar⁴ each independently represent an optionally-substituted aromatic hydrocarbon group or an optionally-substituted aromatic heterocyclic group, Ar³ and Ar⁴ may be bonded to each other to form a ring, and ring A¹ represents an optionally-substituted benzene ring or an optionally-substituted six-membered nitrogen-comprising aromatic ring.

3. An organic compound represented by Formula (III):

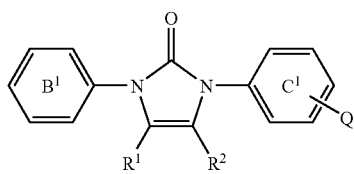

(III)

wherein R¹, R², and Q are as follows:

R¹ and R² each independently represent a substituent that is not hydrogen, or R¹ and R² may be bonded to each other to form a ring, and Q is represented by Formula (I-1):

(I-1)

wherein Ar³ and Ar⁴ each independently represent an optionally-substituted aromatic hydrocarbon group or an optionally-substituted aromatic heterocyclic group, Ar³ and Ar⁴ may be bonded to each other to form a ring, and ring B¹ represents an optionally-substituted benzene ring, and ring C¹ represents a benzene ring that optionally has a substituent in addition to Q.

4. An organic compound represented by Formula (III-2):

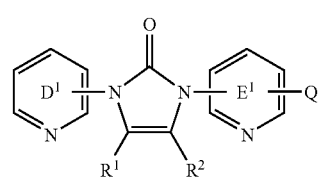

(III-2)

wherein R¹, R², and Q are as follows:

R¹ and R² each independently represent a substituent that is not hydrogen, or R¹ and R² may be bonded to each other to form a ring, and Q is represented by Formula (I-1):

(I-1)

wherein Ar³ and Ar⁴ each independently represent an optionally-substituted aromatic hydrocarbon group or an optionally-substituted aromatic heterocyclic group, Ar³ and Ar⁴ may be bonded to each other to form a ring, and ring D¹ represents an optionally-substituted pyridine ring, and ring E¹ represents a pyridine ring that optionally has a substituent in addition to Q.

5. An organic compound represented by Formula (IV):

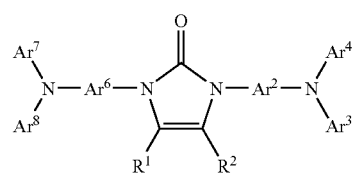

(IV)

wherein Ar² to Ar⁴, R¹, and R² are as follows:

Ar² represents an optionally-substituted aromatic hydrocarbon group or an optionally-substituted aromatic heterocyclic group, R¹ and R² each independently represent a substituent that is not hydrogen, or R¹ and R² may be bonded to each other to form a ring, Ar³ and Ar⁴ each independently represent an optionally-substituted aromatic hydrocarbon group or an optionally-substituted aromatic heterocyclic group, Ar³ and Ar⁴ may be bonded to each other to form a ring, and Ar⁶ to Ar⁸ each independently represent an optionally-substituted aromatic hydrocarbon group or an optionally-substituted aromatic heterocyclic group, and Ar⁷ and Ar⁸ are optionally bonded to each other to form a ring.

6. The organic compound according to claim 1, wherein the organic compound comprises an N-carbazolyl group represented by Formula (I-3) as a partial structure:

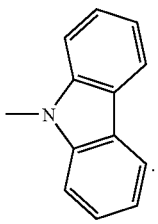

(I-3)

7. A charge-transporting material comprising an organic compound represented by Formula (I):

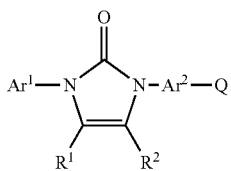

(I)

wherein Ar$^1$ represents an optionally-substituted aromatic hydrocarbon group, an optionally-substituted aromatic heterocyclic group, or an optionally-substituted alkyl group, Ar$^2$ represents an optionally-substituted aromatic hydrocarbon group or an optionally-substituted aromatic heterocyclic group, R$^1$ and R$^2$ each independently represent a substituent that is not hydrogen, or R$^1$ and R$^2$ may be bonded to each other to form a ring, and Q is represented by Formula (I-1):

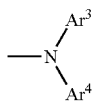

(I-1)

wherein Ar$^3$ and Ar$^4$ each independently represent an optionally-substituted aromatic hydrocarbon group or an optionally-substituted aromatic heterocyclic group, Ar$^3$ and Ar$^4$ may be bonded to each other to form a ring.

8. The charge-transporting material according to claim 7, wherein the charge-transporting material is soluble in toluene in an amount of 2.0 percent by weight or more.

9. A composition for charge-transporting material comprising the charge-transporting material according to claim 7.

10. The composition for charge-transporting material according to claim 9, further comprising a phosphorescent emitting material.

11. An organic electroluminescent device comprising an anode, a cathode, and a light-emitting layer provided between the electrodes, on a substrate, the organic electroluminescent device comprising a layer comprising the charge-transporting material according to claim 7.

12. The organic electroluminescent device according to claim 11, wherein the layer comprising the charge-transporting material is a layer formed by using a composition comprising the charge-transporting material.

13. The organic compound of claim 3, wherein R$^1$ and R$^2$ are independently selected from the group consisting of an optionally-substituted alkyl group, an optionally-substituted alkenyl group, an optionally-substituted alkynyl group, an optionally-substituted aralkyl group, an optionally-substituted amino group, an optionally-substituted arylamino group, an optionally-substituted heteroarylamino group, an optionally-substituted acylamino group, an optionally-substituted alkoxy group, an optionally-substituted aryloxy group, an optionally-substituted heteroaryloxy group, an optionally-substituted acyl group, an optionally-substituted alkoxycarbonyl group, an optionally-substituted aryloxycarbonyl group, an optionally-substituted alkylcarbonyloxy group, a halogen atom, a carboxyl group, a cyano group, a hydroxyl group, a mercapto group, an optionally-substituted alkylthio group, an optionally-substituted arylthio group, an optionally-substituted sulfonyl group, an optionally-substituted silyl group, an optionally-substituted boryl group, an optionally-substituted phosphino group, an optionally-substituted heterocyclic group, and an optionally-substituted aromatic hydrocarbon group.

14. The organic compound of formula (I) of claim 1, wherein R$^1$ and R$^2$ are independently an optionally-substituted alkyl group.

15. The organic compound of formula (I) of claim 14, wherein R$^1$ and R$^2$ are independently selected from the group consisting of a methyl group, an ethyl group, an n-propyl group, a 2-propyl group, an n-butyl group, an isobutyl group, and a tert-butyl group.

16. The organic compound of formula (I) of claim 14, wherein R$^1$ and R$^2$ are individually selected from the group consisting of a methyl group, an ethyl group, or an n-propyl group.

17. The organic compound of formula (I) of claim 1, wherein R$^1$ and R$^2$ are bonded to each other to form a ring.

18. The organic compound of claim 4, wherein R$^1$ and R$^2$ are independently selected from the group consisting of an optionally-substituted alkyl group, an optionally-substituted alkenyl group, an optionally-substituted alkynyl group, an optionally-substituted aralkyl group, an optionally-substituted amino group, an optionally-substituted arylamino group, an optionally-substituted heteroarylamino group, an optionally-substituted acylamino group, an optionally-substituted alkoxy group, an optionally-substituted aryloxy group, an optionally-substituted heteroaryloxy group, an optionally-substituted acyl group, an optionally-substituted alkoxycarbonyl group, an optionally-substituted aryloxycarbonyl group, an optionally-substituted alkylcarbonyloxy group, a halogen atom, a carboxyl group, a cyano group, a hydroxyl group, a mercapto group, an optionally-substituted alkylthio group, an optionally-substituted arylthio group, an optionally-substituted sulfonyl group, an optionally-substituted silyl group, an optionally-substituted boryl group, an optionally-substituted phosphino group, an optionally-substituted heterocyclic group, and an optionally-substituted aromatic hydrocarbon group.

19. The organic compound of claim 5, wherein R$^1$ and R$^2$ are independently selected from the group consisting of an optionally-substituted alkyl group, an optionally-substituted alkenyl group, an optionally-substituted alkynyl group, an optionally-substituted aralkyl group, an optionally-substituted amino group, an optionally-substituted arylamino group, an optionally-substituted heteroarylamino group, an optionally-substituted acylamino group, an optionally-substituted alkoxy group, an optionally-substituted aryloxy group, an optionally-substituted heteroaryloxy group, an optionally-substituted acyl group, an optionally-substituted alkoxycarbonyl group, an optionally-substituted aryloxycarbonyl group, an optionally-substituted alkylcarbonyloxy group, a halogen atom, a carboxyl group, a cyano group, a hydroxyl group, a mercapto group, an optionally-substituted alkylthio group, an optionally-substituted arylthio group, an optionally-substituted sulfonyl group, an optionally-substituted silyl group, an optionally-substituted boryl group, an optionally-substituted phosphino group, an optionally-substituted heterocyclic group, and an optionally-substituted aromatic hydrocarbon group.

* * * * *